US007879876B2

(12) United States Patent
Gerber et al.

(10) Patent No.: US 7,879,876 B2
(45) Date of Patent: Feb. 1, 2011

(54) SULFONAMIDE DERIVATIVES AND USE THEREOF FOR THE MODULATION OF METALLOPROTEINASES

(75) Inventors: Patrick Gerber, Etoy (CH); Dominique Swinnen, Beaumont (FR); Agnes Bombrun, Chambesy (CH)

(73) Assignee: Merck Serono SA, Vaud (CH)

( * ) Notice: Subject to any disclaimer, the term of this patent is extended or adjusted under 35 U.S.C. 154(b) by 27 days.

(21) Appl. No.: 12/091,582

(22) PCT Filed: Oct. 24, 2006

(86) PCT No.: PCT/EP2006/067713

§ 371 (c)(1),
(2), (4) Date: Jul. 11, 2008

(87) PCT Pub. No.: WO2007/048788

PCT Pub. Date: May 3, 2007

(65) Prior Publication Data

US 2009/0221575 A1   Sep. 3, 2009

Related U.S. Application Data

(60) Provisional application No. 60/730,404, filed on Oct. 26, 2005.

(30) Foreign Application Priority Data

Oct. 26, 2005 (EP) ................... 05110035

(51) Int. Cl.
*A01N 43/42* (2006.01)
*A61K 31/47* (2006.01)
*C07D 215/36* (2006.01)
*C07D 209/44* (2006.01)

(52) U.S. Cl. ................ 514/309; 514/312; 546/172; 548/470

(58) Field of Classification Search ............... 514/299, 514/309, 284, 359, 290, 312; 546/61, 79, 546/112, 141, 172; 548/482, 470
See application file for complete search history.

(56) References Cited

FOREIGN PATENT DOCUMENTS

| WO | 01/87844 A | 11/2001 |
| WO | 2004/006926 A | 1/2004 |

OTHER PUBLICATIONS

Chong et. al., Brain Res. Brain Res. Rev., 2005, National Institutes of Health, vol. 49, pp. 1-21.*
D'Hooghe, Current Opinion Obstetrics & Gyn., 2003, Lippincott & Williams, vol. 15, pp. 243-249.*
Hong et. al., Science, 1997, Science Press, vol. 278, pp. 1073-1077.*

* cited by examiner

*Primary Examiner*—Sreeni Padmanabhan
*Assistant Examiner*—Sarah Pihonak
(74) *Attorney, Agent, or Firm*—Perkins Coie LLP

(57) ABSTRACT

The present invention is related to sulfonamide derivatives of Formula (Ia)

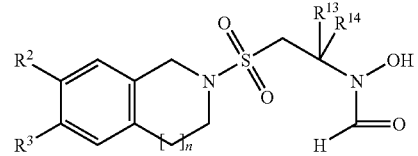

where the groups are as defined in the description, and use thereof in particular for the treatment and/or prophylaxis of autoimmune disorders, inflammatory diseases, cardiovascular diseases, neurodegenerative diseases, cancer, respiratory diseases and fibrosis, including multiple sclerosis, arthritis, emphysema, chronic obstructive pulmonary disease, liver and pulmonary fibrosis.

17 Claims, No Drawings

SULFONAMIDE DERIVATIVES AND USE THEREOF FOR THE MODULATION OF METALLOPROTEINASES

The present application is a National Phase of International Application No. PCT/EP2006/067713 filed Oct. 24, 2006 and claims priority to U.S. Provisional Patent Application No. 60/730,404, filed Oct. 26, 2005 and European Patent Application No. 05110035.2, filed Oct. 26, 2005. The contents of all these applications are expressly incorporated herein by reference in their entireties.

FIELD OF THE INVENTION

The present invention is related to sulfonamide derivatives of Formula (I), pharmaceutical composition thereof, methods of preparation thereof and to their use for the treatment and/or prophylaxis of autoimmune disorders and/or inflammatory diseases, cardiovascular diseases, neurodegenerative diseases, cancer, respiratory diseases and fibrosis. Specifically, the present invention is related to sulfonamide derivatives for the modulation, notably the inhibition of the activity or function of matrix metalloproteinases.

BACKGROUND OF THE INVENTION

Metalloproteinases are a superfamily of proteinases (enzymes) named for their dependence on a metal ion (zinc) in the active site.

The matrix metalloproteinases (MMPs) form a metalloproteinase sub-family having as one of major biological function to catalyse the breakdown of connective tissue or extracellular matrix through their ability to hydrolyse various components of the tissue or matrix, such as collagens, gelatins, proteoglycans, fibronectins and elastin.

The matrix metalloproteinase family is further divided according to their function and substrates (Visse al., 2003, *Circ. Res.*, 92: 827-839) and comprises collagenases (MMP-1, MMP-8, MMP-13 and MMP-18), gelatinases (MMP-2 and MMP-9), stromelysins (MMP-3, MMP-10 and MMP-11), membrane-type MMPs (MT-MMP-1 to MT-MMP-6 and MMP-14, MMP-15, MMP-16, MMP-17, MMP-24 and MMP-25), matrilysins (MMP-7 and MMP-26) and other unclassified MMPs such as metalloelastase (MMP-12), enamelysin (MMP-20), epilysin (MMP-28), MMP-19, MMP-22 and MMP-23.

Apart from their role in degrading connective tissue, MMPs are involved in the biosynthesis of TNF-alpha and in the post-translational proteolysis processing, or shedding of biologically important membrane proteins (Hooper et al., 1997, *Biochem J.*, 321: 265-279). MMPs for example contribute to the local growth and spread of malignant lesions and therefore have been a target for anti-tumor drug development (Fingleton et al., 2003, *Expert Opin. Ther. Targets*, 7(3):385-397. Disorders such as inflammatory disorders like arthritis (Clark et al., 2003, *Expert. Opin. Ther Targets*, 7(1):19-34), respiratory disorders such as emphysema, arteriosclerosis (Galis et al., 2002, *Circ. Res.*, 90:251-262), neurological disorders such as degenerative nervous system diseases, multiple sclerosis (Leppert et al., 2001, *Brain Res. Rev.*, 36:249-257), periodontitis (Ingman et al., 1996, *J. Clin. Periodontal.*, 23:127-1132), pre-term labor (Makratis et al., 2003, *J. Matern Fetal & Neonatal Medicine*, 14(3): 170-6) and wound healing have been demonstrated to be associated with MMPs expression and/or activity.

A recently defined subset of the metalloproteases, the cell-associated A Desintegrin And zinc Metalloprotease (ADAM) family has emerged as an attractive therapeutic target, notably for cancer. At least twenty-three distinct ADAMs have been identified thus far. ADAM-17, also known as tumor necrosis factor-alpha converting enzyme (hereinafter "TACE"), is the most well known ADAM.

TACE is responsible for cleavage of cell bound tumor necrosis factor-alpha ("TNF-α). TNF-α is implicated in many infectious and autoimmune diseases. Moreover, TNF-α is the prime mediator in the inflammatory response seen in sepsis and septic shock. Several TACE inhibitors have been developed and reported in Watson, 2002, *IDrugs*, 5(12):1151-1161.

A wide variety of matrix metalloproteinase inhibitors (MMPIs) has been developed (Skiles et al., 2001, *Current Medicinal Chemistry*, 8, 425-474; Henrotin et al, 2002, *Expert Opin. Ther. Patents*, 12(1):29-43). However, many MMPIs exhibit a muscoskeletal syndrome (tendonitis, fibroplasias, mylasia, arthralasia) as a dose-limiting side effect. It has been proposed that inhibition of MMP-1 or MMP-14 may be responsible for these effects.

WO 01/87844 discloses hydroxamic acid and carboxylic acid derivatives with MMP and TNF inhibitory action for use in the treatment of cancer, inflammation, or an autoimmune, infectious or ocular disease.

WO 2004/006926 discloses sulphonylpiperidine derivatives containing an aryl or heteroaryl group for use as matrix metalloproteinase (MMP) inhibitors, in particular TACE.

Therefore, there is an increasing need to develop matrix metalloproteinase inhibitors with a well-defined specificity profile.

Specific inhibitors, especially towards MMP-1, have been reported, including MMP-13 inhibitors (Stotnicki et al., 2003, *Current Opinion in Drug Discovery and Development*, 6(5):742-759), MMP-12 inhibitors (*Expert. Opin. Ther. Patents*, 2004, 14(11):1637-1640), MMP-2 and MMP-9 inhibitors (Wada et al., 2002, *J. Biol. Chem.* 45: 219-232). The high relevance of the metalloproteinase pathway in some widely spread diseases stresses the need to develop inhibitors, including selective inhibitors of MMPs, especially of MMP-12.

Since excessive TNF-α production has been noted in several disease conditions also characterized by MMP-mediated tissue degradation, compounds which inhibit MMPs and/or TNF-α production may also have a particular advantage in diseases where both mechanisms are involved.

SUMMARY OF THE INVENTION

It is an object of the invention to provide substances which are suitable for the treatment and/or prevention of disorders related to autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

It is further an object of the present invention to provide substances which are suitable for the treatment and/or prevention of multiple sclerosis, arthritis such as osteoarthritis and rheumatoid arthritis, emphysema, psoriasis, obstructive pulmonary disease and fibrosis.

It is notably an object of the present invention to provide chemical compounds which are able to modulate, especially inhibit the activity or function of matrix metalloproteinases, especially gelatinases and elastase in mammals, especially in humans.

It is notably an object of the present invention to provide chemical compounds which are able to modulate, especially inhibit the activity or function of TACE, especially in mammals, especially in humans.

It is furthermore an object of the present invention to provide a new category of pharmaceutical formulations for the treatment of and/or diseases mediated selected from autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

It is furthermore an object of the present invention to provide processes for making chemical compounds according to the invention.

It is finally an object of the present invention to provide a method for the treatment and/or prevention of disorders selected from autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

In a first aspect, the invention provides sulfonamide derivatives of Formula (I):

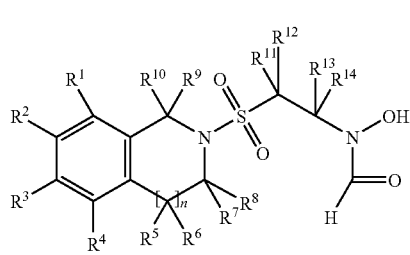

(I)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and n are defined in the detailed description.

In a second aspect, the invention provides a compound according to Formula (I) for use as a medicament, in particular for the prophylaxis and/or treatment of the diseases listed below.

In a third aspect, the invention provides a use of a compound according to Formula (I) for the preparation of a pharmaceutical composition for the treatment of a disorder selected from autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

In a fourth aspect, the invention provides a pharmaceutical composition comprising at least one a compound according to Formula (I) and a pharmaceutically acceptable carrier, diluent or excipient thereof.

In a fifth aspect, the invention provides a method of treatment comprising the administration of a compound according to Formula (I) in a patient in need thereof.

In a sixth aspect, the invention provides methods of synthesis of a compound according to Formula (I).

In a seventh aspect, the invention provides compounds according to Formula (II):

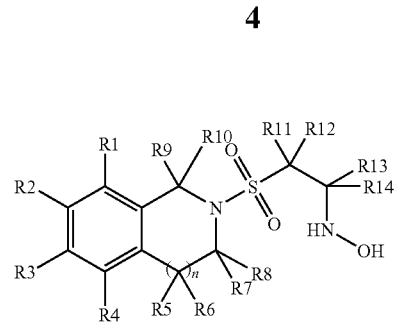

(II)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and n are defined in the detailed description.

In an eight aspect, the invention provides compounds according to Formula (III):

(III)

wherein $R^1$, $R^2$, $R^3$, $R^4$, $R^5$, $R^6$, $R^7$, $R^8$, $R^9$, $R^{10}$, $R^{11}$, $R^{13}$, $R^{14}$ and n are defined in the detailed description.

In a ninth aspect, the invention provides compounds according to Formula (VI):

(VI)

wherein $R^1$, $R^2$, $R^3$, $R^5$, $R^6$, $R^7$, $R^8$, $R^9$, $R^{10}$, $R^{11}$, $R^{12}$, $R^{13}$, $R^{14}$ and n are defined in the detailed description.

In a tenth aspect, the invention provides compounds according to Formula (VIII):

(VIII)

wherein $R^1$, $R^2$, $R^3$, $R^4$, $R^5$, $R^6$, $R^7$, $R^8$, $R^9$, $R^{10}$$R^{11}$, $R^{12}$, $R^{14}$ and n are defined in the detailed description.

In an eleventh aspect, the invention provides compounds according to Formula (IX):

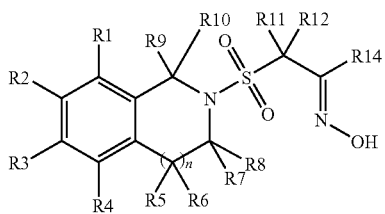

wherein $R^1, R^2, R^3, R^4, R^5, R^6, R^7, R^8, R^9, R^{10}, R^{11}, R^{12}, R^{14}$ and n are defined in the detailed description.

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

The term "MMPs" refers to "matrix metalloproteinases". For recent reviews of MMPs, see Visse et al., 2003 above; Fingleton et al, 2003, above; Clark et al., 2003, above and Doherty et al, 2002, *Expert Opinion Therapeutic Patents* 12(5):665-707.

Illustrative but not limiting examples of such MMPs are:

Collagenases: usually associated with diseases linked to breakdown of collagen-based tissue e.g. rheumatoid arthritis and osteoarthritis:

MMP-1 (also known as collagenase 1, or fibroblast collagenase), substrates collagen I, collagen II, collagen III, gelatin, proteoglycans. Over-expression of this enzyme is believed to be associated with emphysema, with hyperkeratosis and atherosclerosis, overexpressed alone in papillary carcinoma.

MMP-8 (also known as collagenase 2, or neutrophil collagenase), substrates collagen I, collagen II, collagen III, collagen V, collagen VII, collagen IX, gelatin over-expression of which can lead to non-healing chronic ulcers.

MMP-13 (also known as collagenase 3), substrates collagen I, collagen II, collagen III, collagen IV, collagen IX, collagen X, collagen XIV, fibronectin, gelatin, recently identified as being over-expressed alone in breast carcinoma and involved in rheumatoid arthritis.

Stromelysins:

MMP-3 (also known as stromelysin 1), substrates collagen III, collagen IV, collagen V, collagen IX, collagen X, laminin, nidogen, over-expression believed to be involved in atherosclerosis, aneurysm and restenosis.

Gelatinases—inhibition believed to exert a favorable effect on cancer, in particular invasion and metastasis.

MMP-2 (also known as gelatinase A, 72 kDa gelatinase, basement membrane collagenase, or proteoglycanase), substrates Collagen I, Collagen II, Collagen IV, Collagen V, Collagen VII, Collagen X, Collagen XI, collagen XIV, elastin, fibronectin, gelatin, nidogen, believed to be associated with tumor progression through specificity for type IV Collagen (high expression observed in solid tumors and believed to be associated with their ability to grow, invade, develop new blood vessels and metastasize) and to be involved in acute lung inflammation and in respiratory distress syndrome (Krishna et al., 2004, *Expert Opin. Invest. Drugs,* 13(3): 255-267).

MMP-9 (also known as gelatinase B, or 92 kDa gelatinase), substrates Collagen I, Collagen III, Collagen IV, Collagen V, Collagen VII, collagen X, Collagen XIV, elastin, fibronectin, gelatin, nidogen. The above enzyme is believed to be associated with tumor progression through specificity for type IV Collagen, to be released by eosinophils in response to exogenous factors such as air pollutants, allergens and viruses, to be involved in the inflammatory response in multiple sclerosis (Opdenakker et al., 2003, *The Lancet Neurology,* 2, 747-756) and asthma and to be involved in acute lung inflammation, respiratory distress syndrome, chronic obstructive pulmonary disorder (COPD) and/or asthma (Krishna et al., 2004, above). MMP-9 is also thought to be involved in stroke (Horstmann et al., 2003, *Stroke,* 34(9): 2165-70).

Unclassified MMPs:

MMP-12 (also known as metalloelastase, human macrophage elastase, or HME), substrates fibronectin, laminin, believed to play a role in tumour growth inhibition and regulation of inflammation such as multiple sclerosis (Vos et al, 2003, *Journal of Neuroimmunology,* 138, 106-114) and to play a pathological role in emphysema, COPD (Belvisi et al., 2003, *Inflam. Res.* 52: 95-100) and in atherosclerosis, aneurysm and restenosis.

The expression "MMP-associated disorder" refers to a disorder which is treatable according to the invention and that encompasses all disorders in which the expression and/or activity of at least one MMP needs to be decreased irrespective of the cause of such disorders. Such disorders include, for example, those caused by inappropriate extracellular matrix (ECM) degradation.

Illustrative but not limiting examples of such MMP-associated disorders are:

Cancer such as breast cancer and solid tumors; inflammatory disorders such as for example inflammatory bowel diseases and neuroinflammation such as multiple sclerosis; lung diseases such as chronic obstructive pulmonary disorder (COPD), emphysema, asthma, acute lung injury, and acute respiratory distress syndrome; dental diseases such as periodontal disease and gingivitis; joint and bone diseases such as osteoarthritis and rheumatoid arthritis; liver diseases such as liver fibrosis, cirrhosis and chronic liver disease; fibrotic diseases such as pulmonary fibrosis, pancreatitis, lupus, glomerulosclerosis, systemic sclerosis skin fibrosis, post-radiation fibrosis and cystic fibrosis; vascular pathologies such as aortic aneurysm, atherosclerosis, hypertension, cardiomyopathy and myocardial infarction; restenosis; opthalmological disorders such as diabetic retinopathy, dry eye syndrome, macula degeneration and corneal ulceration and degenerative diseases of the central nervous system such as amyotrophic lateral sclerosis.

TACE inhibitors according to the invention are useful for the treatment of several disorders such as inflammatory/autoimmune diseases, including but not limited to rheumatoid arthritis, osteoarthritis, Crohn's disease and other inflammatory bowel diseases and inflammatory gastrointestinal diseases, and systemic lupus erythematosis; reperfusion injuries; systemic inflammatory response syndromes, including but not limited to sepsis, burn injury, pancreatitis, and adult respiratory distress syndrome; allergic and dermatologic diseases, including but not limited to delayed type hypersensitivity, psoriasis, asthma, eczema, allergic rhinitis, and allergic conjunctivitis; cardiovascular diseases, including but not limited to hyperlipidemia, myocardial infarction, atherosclerosis, arteriosclerosis and restenosis; metabolic diseases; neurologic diseases, including but not limited to Alzheimer's disease, Parkinson's disease, multiple sclerosis, aneurism, and stroke; transplant rejection; diseases of cancer and malignancy, including but not limited to colorectal cancer and leukemias; renal diseases, including but not limited to nephrotic syndromes and glomerulonephritis; infectious diseases, including but not limited to HIV infection and neuropathy. Examples of diseases for which TACE inhibitors are useful in the treatment thereof are disclosed in Watson, 2002, above.

In the context of the present invention, the terms "substance" or "substances", "compound" or "compounds" and "sulphonamide derivative" or "sulphonamide derivatives" are used as substantially having the same meaning.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl(allyl, —$CH_2$CH=$CH_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having an carboxy substituent, including 2-carboxyethyl and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "hetero-aryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having a $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethyl-acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R, together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl and the like.

"Ammonium" refers to a positively charged group —N$^+$RR'R", where each R, R', R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Aminosulfonyl $C_1$-$C_6$-alkyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "aryl $C_1$-$C_6$-alkyl", "heteroaryl $C_1$-$C_6$-alkyl", "cycloalkyl $C_1$-$C_6$-alkyl", "heterocycloalkyl $C_1$-$C_6$-alkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, methane sulfonic acid, naphthalene disulfonic acid, and poly-galacturonic acid, as well as salts formed with basic amino acids such as Lysine or Arginine.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. For example, a chemical masking group for alcohol derivatives could be selected from carboxylic acid ester (e.g. acetate, lysine ester) or phosphoric acid esters (e.g. phosphoric acid monoester).

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex® (Biogen) or Betaferon® (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant interferon-β) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in *E. coli*, commercially available under the trademark Betaseron®, it may preferably be administered sub-cutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intramuscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 μg or 6 MIU to 12 MIU per person.

Compounds according to the present invention also comprise pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

It has been found that compounds of the present invention are modulators of the matrix metalloproteinases, including MMP-12. When the matrix metalloproteinase enzyme is inhibited by the compounds of the present invention, the inhibited MMP(s) is (are) unable to exert its enzymatic, biological and/or pharmacological effects.

It has now been found that compounds of the present invention are modulators of the activity or function of TACE.

The compounds of the present invention are therefore useful in the treatment and prevention of autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis. In one embodiment, the invention provides derivatives of Formula (I)

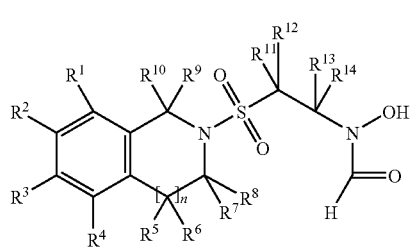

(I)

wherein:

$R^1$, $R^2$, $R^3$ and $R^4$ are independently selected from H, halogen, optionally substituted $C_1$-$C_6$ alkyl, optionally substituted $C_2$-$C_6$ alkenyl, optionally substituted $C_2$-$C_6$ alkynyl, optionally substituted alkoxy, including methoxy, optionally substituted aryl, optionally substituted heteroaryl, optionally substituted $C_3$-$C_8$ cycloalkyl, optionally substituted heterocycloalkyl, optionally substituted sulfonyl, optionally substituted amino sulfonyl, optionally substituted sulfonyl amino, optionally substituted aminocarbonyl, optionally substituted acylamino, optionally substituted amino and optionally substituted hydroxy;

$R^5$, $R^6$, $R^7$, $R^8$, $R^9$ and $R^{10}$ are independently selected from H, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted heterocycloalkyl, optionally substituted aryl and optionally substituted heteroaryl;

$R^{11}$ and $R^{12}$ are independently selected from H, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted heterocycloalkyl, optionally substituted aryl and optionally substituted heteroaryl; or $R^{11}$ and $R^{12}$ taken together form an optionally substituted $C_3$-$C_8$ cycloalkyl or an optionally substituted heterocycloalkyl;

$R^{13}$ is selected from H, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted heterocycloalkyl, optionally substituted aryl and optionally substituted heteroaryl; or $R^{11}$ (or $R^{12}$) and $R^{13}$ taken together form an optionally substituted $C_3$-$C_8$ cycloalkyl or an optionally substituted heterocycloalkyl;

$R^{14}$ is selected from H; optionally substituted $C_1$-$C_6$ alkyl, including pentyl; optionally substituted $C_2$-$C_6$ alkenyl; optionally substituted $C_2$-$C_6$ alkynyl; optionally substituted $C_3$-$C_6$ cycloalkyl, including cyclopropyl (e.g. 1-cyclopropyl); optionally substituted heterocycloalkyl, including optionally substituted dioxolane (e.g. 2,2-dimethyl-1,3-dioxolan-4-yl); optionally substituted aryl; optionally substituted heteroaryl, including optionally substituted thienyl (e.g. 2-thienyl, 3-thienyl), optionally substituted pyrimidinyl (e.g. pyrimidin-5-yl), optionally substituted pyridinyl (e.g. pyridine-3-yl, 6-methoxy pyridin-3-yl); optionally substituted aryl $C_1$-$C_6$ alkyl, including optionally substituted phenyl $C_1$-$C_6$ alkyl such as phenyl ethyl (e.g. 2-phenyl ethyl); optionally substituted heteroaryl $C_1$-$C_6$ alkyl; optionally substituted $C_3$-$C_6$ cycloalkyl $C_1$-$C_6$ alkyl and optionally substituted heterocycloalkyl $C_1$-$C_6$ alkyl, including optionally substituted morpholin $C_1$-$C_6$ alkyl such as morpholin propyl (e.g. 2-morpholino-2-propyl); or $R^{13}$ and $R^{14}$ taken together form an optionally substituted $C_3$-$C_8$ cycloalkyl or an optionally substituted heterocycloalkyl;

n is an integer selected from 0 and 1;

as well as its geometrical isomers, its optically active forms as enantiomers, diastereomers, tautomers, racemate forms, as well as pharmaceutically acceptable salts thereof.

In a first preferred embodiment, the invention provides derivatives of Formula (I), wherein $R^1$, $R^4$, $R^5$, $R^6$, $R^7$, $R^8$, $R^9$, $R^{10}$, $R^{11}$ and $R^{12}$ are hydrogen, $R^{13}$ and $R^{14}$ have the meanings given below. In this preferred embodiment, the compounds are defined by the following Formula (Ia)

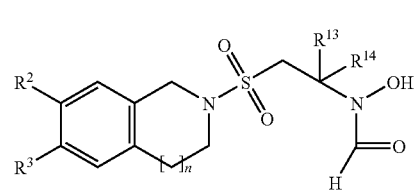

(Ia)

wherein:

$R^2$ and $R^3$ are independently selected from:
hydrogen,
halogen,
linear or branched $C_1$-$C_6$ alkyl, optionally substituted with one or more substituents selected from the group consisting of halogen, hydroxy, linear or branched $C_1$-$C_6$ alkoxy, phenoxy,
linear or branched $C_1$-$C_6$ alkoxy,
phenyl, optionally substituted with one or more substituents selected from the group consisting of halogen, hydroxy, linear or branched $C_1$-$C_6$ alkyl,
phenyl-linear or branched $C_1$-$C_6$ alkyl, said phenyl optionally substituted with one or more substituents selected from the group consisting of halogen, hydroxy, linear or branched $C_1$-$C_6$ alkyl,
a three to six member heterocyclic group having at least a heteroatom selected from the group consisting of oxygen, nitrogen and sulfur;

$R^{13}$ is selected from H, linear or branched $C_1$-$C_6$ alkyl;

$R^{14}$ is selected from
linear or branched $C_1$-$C_8$ alkyl, optionally substituted with one or more halogen atoms and/or hydroxy groups, said $C_1$-$C_8$ alkyl optionally containing one or more unsaturated C—C bonds or containing one or more oxygen or sulfur atoms in the alkyl chain,
$C_3$-$C_8$ cycloalkyl, optionally substituted with a carboxy or a linear or branched $C_1$-$C_4$ alkoxycarbonyl group,
phenyl,
phenyl-linear or branched $C_1$-$C_6$ alkyl, said $C_1$-$C_6$ alkyl optionally containing one oxygen atom, a heterocyclic or heterocycloalkyl group selected from the group consisting of: 1,3-dioxolane, 2,2-dimethyl-1,3-dioxolane, thiophene, 1-methyl-1-morpholino-4-yl-ethyl, pyrimidine, pyridine, said pyridine optionally substituted with a hydroxy or $C_1$-$C_6$ alkoxy group; pyridinyl-linear or branched $C_1$-$C_4$ alkyl; piperidine, said piperidine optionally substituted with phenyl-$C_1$-$C_4$ alkyl; furane, tetrahydrofurane; 2-tetrahydrofuran-2-ylethyl, pyrrolidine N-carboxylic acid, $C_1$-$C_4$ linear or branched N-alkoxycarbonylpyrrolidin-2-yl; tetrahydropyrane; or $R^{13}$ and $R^{14}$ taken together form a $C_3$-$C_8$ cycloalkyl;

n is an integer selected from 0 and 1;

as well as its geometrical isomers, its optically active forms as enantiomers, diastereomers, tautomers, racemate forms, as well as pharmaceutically acceptable salts thereof.

In another preferred embodiment, the invention provides derivatives of Formula (I) wherein $R^1$, $R^2$, $R^3$ and $R^4$ are independently selected from H and optionally substituted alkoxy, including methoxy.

In another further preferred embodiment, the invention provides derivatives of Formula (I) wherein $R^1$ and $R^4$ are H; $R^2$ and $R^3$ are independently selected from H and optionally substituted alkoxy, including methoxy.

In another preferred embodiment, the invention provides derivatives of Formula (I) wherein $R^5$, $R^6$, $R^7$, $R^8$, $R^9$ and $R^{10}$ are H.

In another preferred embodiment, the invention provides derivatives of Formula (I) wherein $R^{11}$ and $R^{12}$ are H.

In another preferred embodiment, the invention provides derivatives of Formula (I) wherein $R^{13}$ is H.

In another preferred embodiment, the invention provides derivatives of Formula (I) wherein $R^1$, $R^4$, $R^5$, $R^6$, $R^7$, $R^8$, $R^9$, $R^{10}$, $R^{11}$, $R^{12}$ and $R^{13}$ are H; $R^2$ and $R^4$ are independently selected from H and optionally substituted alkoxy, including methoxy; $R^{14}$ and n are as defined in the description.

In another preferred embodiment, the invention provides derivatives of Formula (I) wherein $R^{14}$ is selected from optionally substituted $C_1$-$C_6$ alkyl; optionally substituted $C_2$-$C_6$ alkenyl; optionally substituted $C_2$-$C_6$ alkynyl; optionally substituted $C_3$-$C_6$ cycloalkyl; optionally substituted heterocycloalkyl; optionally substituted aryl $C_1$-$C_6$ alkyl; optionally substituted heteroaryl $C_1$-$C_6$ alkyl; optionally substituted $C_3$-$C_6$ cycloalkyl $C_1$-$C_6$ alkyl and optionally substituted heterocycloalkyl $C_1$-$C_6$ alkyl.

In another preferred embodiment, the invention provides derivatives of Formula (I) wherein $R^{14}$ is selected from optionally substituted aryl and optionally substituted heteroaryl.

In another preferred embodiment, the invention provides derivatives of Formula (I) wherein n is 0.

In another preferred embodiment, the invention provides derivatives of Formula (I) wherein n is 1.

In another preferred embodiment, the invention provides derivatives of Formula (Ia) wherein $R^2$ and $R^3$ are independently selected from H and alkoxy.

In another preferred embodiment, the invention provides derivatives of Formula (Ia) wherein $R^{13}$ is H.

In another preferred embodiment, the invention provides derivatives of Formula (Ia) wherein $R^{13}$ is H; $R^2$ is selected from H and alkoxy; $R^{14}$ and n are as defined in the first preferred embodiment.

In another preferred embodiment, the invention provides derivatives of Formula (Ia) wherein $R^{14}$ is selected from phenyl and a heterocyclic or heterocycloalkyl group selected from the group consisting of: 1,3-dioxolane, 2,2-dimethyl-1,3-dioxolane, thiophene, 1-methyl-1-morpholino-4-ylethyl, pyrimidine, pyridine, said pyridine optionally substituted with a hydroxy or $C_1$-$C_6$ alkoxy group; pyridinyl-linear or branched $C_1$-$C_4$ alkyl; piperidine, said piperidine optionally substituted with phenyl-$C_1$-$C_4$ alkyl; furane, tetrahydrofurane; 2-tetrahydrofuran-2-ylethyl, pyrrolidine N-carboxylic acid, $C_1$-$C_4$ linear or branched N-alkoxycarbonylpyrrolidin-2-yl; tetrahydropyrane.

In another preferred embodiment, the invention provides derivatives of Formula (Ia) wherein $R^{13}$ is selected from H, linear or branched $C_1$-$C_6$ alkyl and $R_{14}$ is linear or branched $C_1$-$C_8$ alkyl, optionally substituted with one or more halogen atoms and/or hydroxy groups, said $C_1$-$C_8$ alkyl optionally containing one or more unsaturated C—C bonds or containing one or more oxygen or sulfur atoms in the alkyl chain.

In another preferred embodiment, the invention provides derivatives of Formula (Ia) wherein $R^{13}$ is selected from H, linear or branched $C_1$-$C_6$ alkyl and $R_{14}$ is $C_3$-$C_8$ cycloalkyl, optionally substituted with a carboxy or a linear or branched $C_1$-$C_4$ alkoxycarbonyl group.

In another preferred embodiment, the invention provides derivatives of Formula (Ia) wherein $R^{13}$ is selected from H, linear or branched $C_1$-$C_6$ alkyl and $R_{14}$ is phenyl or phenyl-linear or branched $C_1$-$C_6$ alkyl, said $C_1$-$C_6$ alkyl optionally containing one oxygen atom.

In another preferred embodiment, the invention provides derivatives of Formula (Ia) wherein $R^{13}$ is selected from H, linear or branched $C_1$-$C_6$ alkyl and $R_{14}$ is a heterocyclic or heterocycloalkyl group selected from the group consisting of: 1,3-dioxolane, 2,2-dimethyl-1,3-dioxolane, thiophene, 1-methyl-1-morpholino-4-ylethyl, pyrimidine, pyridine, said pyridine optionally substituted with a hydroxy or $C_1$-$C_6$ alkoxy group; pyridinyl-linear or branched $C_1$-$C_4$ alkyl; piperidine, said piperidine optionally substituted with phenyl-$C_1$-$C_4$ alkyl; furane, tetrahydrofurane; 2-tetrahydrofuran-2-ylethyl, pyrrolidine N-carboxylic acid, $C_1$-$C_4$ linear or branched N-alkoxycarbonylpyrrolidin-2-yl; tetrahydropyrane.

In another preferred embodiment, the invention provides derivatives of Formula (Ia) wherein $R^{13}$ and $R^{14}$ taken together form a cyclopentyl group.

In the above preferred embodiments:

halogen is preferably fluorine, chlorine or bromine;

linear or branched $C_1$-$C_8$ alkyl, preferably a $C_7$ alkyl, more preferably a $C_8$ alkyl, optionally substituted with one or more halogen atoms and/or hydroxy groups, linear or branched $C_1$-$C_6$ alkoxy, phenoxy, said $C_1$-$C_8$ alkyl optionally containing one or more unsaturated C—C bonds or containing one or more oxygen or sulfur atoms in the alkyl chain is preferably methyl, ethyl, isopropyl, sec-butyl, tert-butyl, sec-pentyl, trifluoromethyl, 3,3,3-trifluoropropyl, 2-methyl-hept-4-yn-2-yl, 1,1-dimethyl-hexyl, 2-hydroxyethyl;

linear or branched $C_1$-$C_6$ alkoxy, is preferably methoxy, propoxy, isopropoxy phenyl, optionally substituted with one or more substituents selected from the group consisting of halogen, hydroxy, linear or branched $C_1$-$C_6$ alkyl, is preferably 4-fluorophenyl, 3-hydroxyphenyl;

phenyl-linear or branched $C_1$-$C_6$ alkyl, said phenyl optionally substituted with one or more substituents selected from the group consisting of halogen, hydroxy, linear or branched $C_1$-$C_6$ alkyl, said $C_1$-$C_6$ alkyl optionally containing one oxygen atom, is preferably 2-phenylethyl, 2-phenyl-1,1-dimethyl-ethyl, benzyloxymethyl;

a three to six member heterocyclic group having at least a heteroatom selected from the group consisting of oxygen, nitrogen and sulfur is preferably 1,3-dioxolane, 2,2-dimethyl-1,3-dioxolane, thiophene-2-yl, thiophene-3-yl, 1-methyl-1-morpholino-4-ylethyl, pyrimi-din-5-yl, 3-pyridyl, 4-pyridyl, 2-methoxy-5-pyridyl, 2-pyridin-3-yl-ethyl, N-benzyl-pipe-ridin-4-yl, 3-furyl, tetrahydrofuran-2-yl, 2-tetrahydrofuran-2-ylethyl, 1,3-dioxolane, N-tert-butoxycarbonylpyrrolidin-2-yl, 4-tetrahydropyran-yl;

$C_3$-$C_8$ cycloalkyl, optionally substituted with a carboxy or a linear or branched $C_1$-$C_4$ alkoxycarbonyl group is preferably cyclopentyl, cyclopropyl, methoxycarbonylcyclopro-pyl;

In a most preferred embodiment, the present invention provides compounds of formula (Ia) wherein $R^{14}$ is 2,2-dimethyl-1,3-dioxolane, even more preferably $R^{13}$ is hydrogen, still more preferably $R_2$ and $R_3$ are methoxy. A representative compound is N-{2-[(6,7-di-methoxy-3,4-dihydroisoquinolin-2(1H)-yl) sulfonyl]-1-[(4S)-2,2-dimethyl-1,3-dioxolan-4-yl]ethyl}-N-hydroxyformamide.

Compounds of the present invention include in particular those selected from the following group:

N-{1-[(3,4-dihydroisoquinolin-2(1H)-ylsulfonyl)methyl]-3-phenylpropyl}-N-hydroxy formamide;
N-{2-(3,4-dihydroisoquinolin-2(1H)-ylsulfonyl)-1-[(4S)-2,2-dimethyl-1,3-dioxolan-4-yl]ethyl}-N-hydroxyformamide;
N-{1-[(3,4-dihydroisoquinolin-2(1H)-ylsulfonyl)methyl]hexyl}-N-hydroxyformamide;
N-[1-cyclopropyl-2-(3,4-dihydroisoquinolin-2(1H)-ylsulfonyl)ethyl]-N-hydroxy formamide;
N-[2-(3,4-dihydroisoquinolin-2(1H)-ylsulfonyl)-1-(2-thienyl)ethyl]-N-hydroxyformamide;
N-{1-[(1,3-dihydro-2H-isoindol-2-ylsulfonyl)methyl]-3-phenylpropyl}-N-hydroxy formamide;
N-[2-(3,4-dihydroisoquinolin-2(1H)-ylsulfonyl)-1-(3-thienyl)ethyl]-N-hydroxyformamide;
N-{1-[(3,4-dihydroisoquinolin-2(1H)-ylsulfonyl)methyl]-2-methyl-2-morpholin-4-yl propyl}-N-hydroxyformamide;
N-[2-(3,4-dihydroisoquinolin-2(1H)-ylsulfonyl)-1-pyrimidin-5-ylethyl]-N-hydroxy formamide;
N-[2-(3,4-dihydroisoquinolin-2(1H)-ylsulfonyl)-1-pyridin-3-ylethyl]-N-hydroxy formamide;
N-[2-(3,4-dihydroisoquinolin-2(1H)-ylsulfonyl)-1-pyridin-3-ylethyl]-N-hydroxy formamide, hydrochloride salt;
N-(1-{[(6,7-dimethoxy-3,4-dihydroisoquinolin-2(1H)-yl)sulfonyl]methyl}-3-phenyl propyl)-N-hydroxyformamide;
N-[2-(3,4-dihydroisoquinolin-2(1H)-ylsulfonyl)-1-(6-methoxypyridin-3-yl)ethyl]-N-hydroxyformamide;
N-{2-[(6,7-dimethoxy-3,4-dihydroisoquinolin-2(1H)-yl)sulfonyl]-1-[(4S)-2,2-dimethyl-1,3-dioxolan-4-yl]ethyl}-N-hydroxyformamide;
N-{1-cyclopentyl-2-[(6,7-dimethoxy-3,4-dihydroisoquinolin-2(1H)-yl)sulfonyl]ethyl}-N-hydroxyformamide;
N-{2-(1,3-dihydro-2H-isoindol-2-ylsulfonyl)-1-[(4S)-2,2-dimethyl-1,3-dioxolan-4-yl]ethyl}-N-hydroxyformamide;
N-(1-{[(6,7-dimethoxy-3,4-dihydroisoquinolin-2(1H)-yl)sulfonyl]methyl}-2-ethylbutyl)-N-hydroxyformamide;
N-{1-[(4S)-2,2-dimethyl-1,3-dioxolan-4-yl]-2-[(6-isopropyl-3,4-dihydroisoquinolin-2(1H)-yl)sulfonyl]ethyl}-N-hydroxyformamide;
N-{2-[(7-chloro-3,4-dihydroisoquinolin-2(1H)-yl)sulfonyl]-1-[(4S)-2,2-dimethyl-1,3-dioxolan-4-yl]ethyl}-N-hydroxyformamide;
N-(1-{[(6,7-dimethoxy-3,4-dihydroisoquinolin-2(1H)-yl)sulfonyl]methyl}-2,2-dimethylpropyl)-N-hydroxyformamide;
N-{2-[(7-chloro-3,4-dihydroisoquinolin-2(1H)-yl)sulfonyl]-1-cyclopentylethyl}-N-hydroxyformamide;
N-{(1R)-2-[(7-chloro-3,4-dihydroisoquinolin-2(1H)-yl)sulfonyl]-1-[(2R)-tetrahydrofuran-2-yl]ethyl}-N-hydroxyformamide;
N-{(1S)-2-[(7-chloro-3,4-dihydroisoquinolin-2(1H)-yl)sulfonyl]-1-[(2R)-tetrahydrofuran-2-yl]ethyl}-N-hydroxyformamide;
N-((1S,2S)-1-{[(6,7-dimethoxy-3,4-dihydroisoquinolin-2(1H)-yl)sulfonyl]methyl}-2,3-dihydroxypropyl)-N-hydroxyformamide;
N-(1-cyclopentyl-2-{[6-(trifluoromethyl)-3,4-dihydroisoquinolin-2(1H)-yl]sulfonyl}ethyl)-N-hydroxyformamide;
N-(1-{[(5-fluoro-1,3-dihydro-2H-isoindol-2-yl)sulfonyl]methyl}-3,3-dimethylbutyl)-N-hydroxyformamide;
N-hydroxy-N-((1S)-1-[(2R)-tetrahydrofuran-2-yl]-2-{[7-(trifluoromethyl)-3,4-dihydroisoquinolin-2(1H)-yl]sulfonyl}ethyl)formamide;
N-(1-[(4S)-2,2-dimethyl-1,3-dioxolan-4-yl]-2-{[7-(trifluoromethyl)-3,4-dihydroisoquinolin-2(1H)-yl]sulfonyl}ethyl)-N-hydroxyformamide;
N-{(1S)-2-[(5-fluoro-1,3-dihydro-2H-isoindol-2-yl)sulfonyl]-1-[(2R)-tetrahydrofuran-2-yl]ethyl}-N-hydroxyformamide;
N-[2,2-dimethyl-1-({[6-(trifluoromethyl)-3,4-dihydroisoquinolin-2(1H)-yl]sulfonyl}methyl)hept-4-yn-1-yl]-N-hydroxyformamide;
N-[2,2-dimethyl-3-phenyl-1-({[6-(trifluoromethyl)-3,4-dihydroisoquinolin-2(1H)-yl]sulfonyl}methyl)propyl]-N-hydroxyformamide;
N-hydroxy-N-((1R)-1-[(2R)-tetrahydrofuran-2-yl]-2-{[7-(trifluoromethyl)-3,4-dihydroisoquinolin-2(1H)-yl]sulfonyl}ethyl)formamide;
N-hydroxy-N-[1-{[(7-methoxy-3,4-dihydroisoquinolin-2(1H)-yl)sulfonyl]methyl}-3-(tetrahydrofuran-2-yl)propyl]formamide;
N-(1-{[(6,7-dichloro-3,4-dihydroisoquinolin-2(1H)-yl)sulfonyl]methyl}-2-ethylbutyl)-N-hydroxyformamide;
N-(2-ethyl-1-{[(6-isopropyl-3,4-dihydroisoquinolin-2(1H)-yl)sulfonyl]methyl}butyl)-N-hydroxyformamide;
N-(1-{[(7-bromo-3,4-dihydroisoquinolin-2(1H)-yl)sulfonyl]methyl}-2-ethylbutyl)-N-hydroxyformamide;
N-[2-ethyl-1-({[6-(trifluoromethyl)-3,4-dihydroisoquinolin-2(1H)-yl]sulfonyl}methyl)butyl]-N-hydroxyformamide;
N-(2-ethyl-1-{[(7-methoxy-3,4-dihydroisoquinolin-2(1H)-yl)sulfonyl]methyl}butyl)-N-hydroxyformamide;
N-(1-{[(6,7-dichloro-3,4-dihydroisoquinolin-2(1H)-yl)sulfonyl]methyl}-2-methylpropyl)-N-hydroxyformamide;
N-(3,3-dimethyl-1-{[(7-propoxy-3,4-dihydroisoquinolin-2(1H)-yl)sulfonyl]methyl}butyl)-N-hydroxyformamide;
N-(1-{[(7-chloro-3,4-dihydroisoquinolin-2(1H)-yl)sulfonyl]methyl}-3,3-dimethylbutyl)-N-hydroxyformamide;
N-(1-{[(6,7-dichloro-3,4-dihydroisoquinolin-2(1H)-yl)sulfonyl]methyl}-3,3-dimethylbutyl)-N-hydroxyformamide;
N-[3,3-dimethyl-1-({[6-(trifluoromethyl)-3,4-dihydroisoquinolin-2(1H)-yl]sulfonyl}methyl)butyl]-N-hydroxyformamide;
tert-butyl (2RS)-2-{(1SR)-2-[(6,7-dichloro-3,4-dihydroisoquinolin-2(1H)-yl)sulfonyl]-1-[formyl(hydroxy)amino]ethyl}pyrrolidine-1-carboxylate
N-hydroxy-N-{(1S)-2-[(6-isopropyl-3,4-dihydroisoquinolin-2(1H)-yl)sulfonyl]-1-[(2R)-tetrahydrofuran-2-yl]ethyl}formamide;

tert-butyl (2RS)-2-{(1RS)-2-[(6,7-dichloro-3,4-dihydroiso-
quinolin-2(1H)-yl)sulfonyl]-1-[formyl(hydroxy)amino]
ethyl}pyrrolidine-1-carboxylate
N-hydroxy-N-(1-[(2R)-tetrahydrofuran-2-yl]-2-{[6-(trifluo-
romethyl)-3,4-dihydroisoquinolin-2(1H)-yl]
sulfonyl}ethyl)formamide;
N-(1-{[(7-chloro-3,4-dihydroisoquinolin-2(1H)-yl)sulfo-
nyl]methyl}-3-hydroxypropyl)-N-hydroxyformamide;
N-[2-[(6,7-dichloro-3,4-dihydroisoquinolin-2(1H)-yl)sulfo-
nyl]-1-(hydroxymethyl)ethyl]-N-hydroxyformamide;
N-[1-({[7-(4-fluorophenyl)-3,4-dihydroisoquinolin-2(1H)-
yl]sulfonyl}methyl)-2-methylpropyl]-N-hydroxyforma-
mide;
N-hydroxy-N-(1-{[(7-isopropoxy-3,4-dihydroisoquinolin-2
(1H)-yl)sulfonyl]methyl}-3-methylbutyl)formamide;
N-[2-[(7-fluoro-3,4-dihydroisoquinolin-2(1H)-yl)sulfonyl]-
1-(3-furyl)ethyl]-N-hydroxyformamide;
N-{1-(1-benzylpiperidin-4-yl)-2-[(7-fluoro-3,4-dihydroiso-
quinolin-2(1H)-yl)sulfonyl]ethyl}-N-hydroxyformamide;
N-[1-{[(7-tert-butyl-3,4-dihydroisoquinolin-2(1H)-yl)sulfo-
nyl]methyl}-3-(methylthio)propyl]-N-hydroxyforma-
mide;
N-(1-{[(7-bromo-3,4-dihydroisoquinolin-2(1H)-yl)sulfo-
nyl]methyl}-3-methylbutyl)-N-hydroxyformamide;
N-{2-[(7-bromo-3,4-dihydroisoquinolin-2(1H)-yl)sulfo-
nyl]-1,1-dimethylethyl}-N-hydroxyformamide;
N-(2-(benzyloxy)-1-{[(7-tert-butyl-3,4-dihydroisoquinolin-
2(1H)-yl)sulfonyl]methyl}ethyl)-N-hydroxyformamide;
N-(2-(benzyloxy)-1-{[(7-chloro-3,4-dihydroisoquinolin-2
(1H)-yl)sulfonyl]methyl}ethyl)-N-hydroxyformamide;
N-[2-(benzyloxy)-1-({[7-(trifluoromethyl)-3,4-dihydroiso-
quinolin-2(1H)-yl]sulfonyl}methyl)ethyl]-N-hydroxyfor-
mamide;
N-{1-cyclopentyl-2-[(7-fluoro-3,4-dihydroisoquinolin-2
(1H)-yl)sulfonyl]ethyl}-N-hydroxyformamide;
N-[2-[(7-chloro-3,4-dihydroisoquinolin-2(1H)-yl)sulfonyl]-
1-(phenoxymethyl)ethyl]-N-hydroxyformamide;
N-(1-{[(7-chloro-3,4-dihydroisoquinolin-2(1H)-yl)sulfo-
nyl]methyl}cyclopentyl)-N-hydroxyformamide;
N-[2,2-dimethyl-1-({[6-(trifluoromethyl)-3,4-dihydroiso-
quinolin-2(1H)-yl]sulfonyl}methyl)heptyl]-N-hydroxy-
formamide;
N-{2-[(7-bromo-3,4-dihydroisoquinolin-2(1H)-yl)sulfo-
nyl]-1-cyclopentylethyl}-N-hydroxyformamide;
N-(1-{[(7-chloro-3,4-dihydroisoquinolin-2(1H)-yl)sulfo-
nyl]methyl}-2,2-dimethylpropyl)-N-hydroxyformamide;
N-[2-[(7-tert-butyl-3,4-dihydroisoquinolin-2(1H)-yl)sulfo-
nyl]-1-(tetrahydro-2H-pyran-4-yl)ethyl]-N-hydroxyfor-
mamide;
ethyl 2-{2-[(6,7-dimethoxy-3,4-dihydroisoquinolin-2(1H)-
yl)sulfonyl]-1-[formyl(hydroxy)-amino]
ethyl}cyclopropanecarboxylate
N-(1-cyclopentyl-2-{[7-(3-thienyl)-3,4-dihydroisoquinolin-
2(1H)-yl]sulfonyl}ethyl)-N-hydroxyformamide;
N-{1-cyclopentyl-2-[(7-phenyl-3,4-dihydroisoquinolin-2
(1H)-yl)sulfonyl]ethyl}-N-hydroxyformamide;
N-(1-cyclopentyl-2-{[7-(3-hydroxyphenyl)-3,4-dihydroiso-
quinolin-2(1H)-yl]sulfonyl}ethyl)-N-hydroxyformamide;
2-{2-[(6,7-dimethoxy-3,4-dihydroisoquinolin-2(1H)-yl)sul-
fonyl]-1-[formyl(hydroxy)amino]
ethyl}cyclopropanecarboxylic acid
N-[1-cyclopropyl-2-(1,3-dihydro-2H-isoindol-2-ylsulfonyl)
ethyl]-N-hydroxyformamide;
N-{2-[(7-chloro-3,4-dihydroisoquinolin-2(1H)-yl)sulfo-
nyl]-1-cyclopropylethyl}-N-hydroxyformamide;
N-(1-cyclopropyl-2-{[6-(trifluoromethyl)-3,4-dihydroiso-
quinolin-2(1H)-yl]sulfonyl}ethyl)-N-hydroxyformamide;
N-(1-cyclopropyl-2-{[7-(4-fluorophenyl)-3,4-dihydroiso-
quinolin-2(1H)-yl]sulfonyl}ethyl)-N-hydroxyformamide;
N-(1-{[(7-chloro-3,4-dihydroisoquinolin-2(1H)-yl)sulfo-
nyl]methyl}-4,4,4-trifluorobutyl)-N-hydroxyformamide;
N-{1-cyclopentyl-2-[(6,7-dichloro-3,4-dihydroisoquinolin-
2(1H)-yl)sulfonyl]ethyl}-N-hydroxyformamide;
N-{1-cyclopentyl-2-[(7-isopropoxy-3,4-dihydroisoquino-
lin-2(1H)-yl)sulfonyl]ethyl}-N-hydroxyformamide;
N-{1-cyclopentyl-2-[(7-pyridin-4-yl-3,4-dihydroisoquino-
lin-2(1H)-yl)sulfonyl]ethyl}-N-hydroxyformamide;
N-{1-cyclopentyl-2-[(5-fluoro-1,3-dihydro-2H-isoindol-2-
yl)sulfonyl]ethyl}-N-hydroxyformamide;
N-{1-cyclopentyl-2-[(6-isopropyl-3,4-dihydroisoquinolin-2
(1H)-yl)sulfonyl]ethyl}-N-hydroxyformamide;
N-(1-cyclopentyl-2-{[7-(trifluoromethyl)-3,4-dihydroiso-
quinolin-2(1H)-yl]sulfonyl}ethyl)-N-hydroxyformamide;
N-(1-cyclopropyl-2-{[7-(trifluoromethyl)-3,4-dihydroiso-
quinolin-2(1H)-yl]sulfonyl}ethyl)-N-hydroxyformamide;
N-{1-cyclopropyl-2-[(6,7-dimethoxy-3,4-dihydroisoquino-
lin-2(1H)-yl)sulfonyl]ethyl}-N-hydroxyformamide;
N-{1-cyclopropyl-2-[(6-isopropyl-3,4-dihydroisoquinolin-2
(1H)-yl)sulfonyl]ethyl}-N-hydroxyformamide;
N-(1-{[(7-chloro-3,4-dihydroisoquinolin-2(1H)-yl)sulfo-
nyl]methyl}-3-pyridin-3-ylpropyl)-N-hydroxyforma-
mide.

In another embodiment of the invention, are provided sulfonamide derivatives according to Formula (I) for use as a medicament.

In another embodiment of the invention, is provided a pharmaceutical composition comprising at least one sulfonamide derivative according to the invention and a pharmaceutically acceptable carrier, diluent or excipient thereof.

In another embodiment of the invention, is provided a use of sulfonamide derivatives according to Formula (I) for the preparation of a medicament for the prophylaxis and/or treatment of a disorder selected from autoimmune disorders, inflammatory diseases, stroke, cardiovascular diseases, neurodegenerative diseases, cancer and malignancy, metabolic diseases, allergic and dermatologic diseases, respiratory diseases and fibrosis, including multiple sclerosis, inflammatory bowel disease, arthritis, psoriasis, asthma, emphysema, preterm labor, endometriosis, chronic obstructive pulmonary disease, liver and pulmonary, pancreatic fibrosis, skin fibrosis and liver fibrosis.

In a further embodiment of the invention, is provided a use of sulfonamide derivatives according to Formula (I) for the preparation of a medicament for the prophylaxis and/or treatment of a disorder selected from inflammatory bowel disease, multiple sclerosis, osteoarthritis and rheumatoid arthritis.

In another further embodiment of the invention, is provided a use of sulfonamide derivatives according to Formula (I) for the preparation of a medicament for the prophylaxis and/or treatment of a disorder selected from asthma, emphysema and chronic obstructive pulmonary disease.

In another further embodiment of the invention, is provided a use of sulfonamide derivatives according to Formula (I) for the preparation of a medicament for the prophylaxis and/or treatment of a disorder selected from pulmonary, pancreatic, skin and liver fibrosis.

In another further embodiment of the invention, is provided a use of sulfonamide derivatives according to Formula (I) for the preparation of a medicament for the prophylaxis and/or treatment of a disorder wherein the disorder is a cancer or malignancy.

In another embodiment of the invention, is provided a use of sulfonamide derivatives according to Formula (I) for the modulation, in particular for the inhibition, of the matrix metalloproteinase activity. Particularly, is provided a use according to the invention wherein said matrix metalloproteinase is MMP-12.

In another embodiment, compounds according to the invention are selective inhibitors of metalloproteineases selected from MMP-2, MMP-9 and/or MMP-12 over MMP-1.

In another embodiment of the invention, is provided a use of sulfonamide derivatives according to Formula (I) for the modulation, in particular for the inhibition, of the TACE activity. Preferably, compounds according to the invention are selective inhibitors of TACE over MMP-1.

In another embodiment of the invention, is provided a use of sulphonamide derivatives according to Formula (I) for the in vitro modulation of metalloproteinases or TACE.

In another embodiment, the invention provides a method of treatment and/or prophylaxis of a disease comprising the administration of a compound according to Formula (I), in a patient in need thereof and wherein the disease is selected from autoimmune disorders, inflammatory diseases, cardiovascular diseases, neurodegenerative diseases, stroke, allergic and dermatologic diseases, metabolic disorders, cancer and malignancy, respiratory diseases and fibrosis, including multiple sclerosis, arthritis, rheumatoid arthritis, osteoarthritis, asthma, emphysema, pre-term labor, endometriosis, chronic obstructive pulmonary disease (COPD), liver, psoriasis, skin and pulmonary fibrosis.

In another embodiment, the invention provides a process for the preparation of a sulfonamide derivative according to Formula (I), comprising the step of reacting a compound of Formula (II) with a formylating agent of formula (FA):

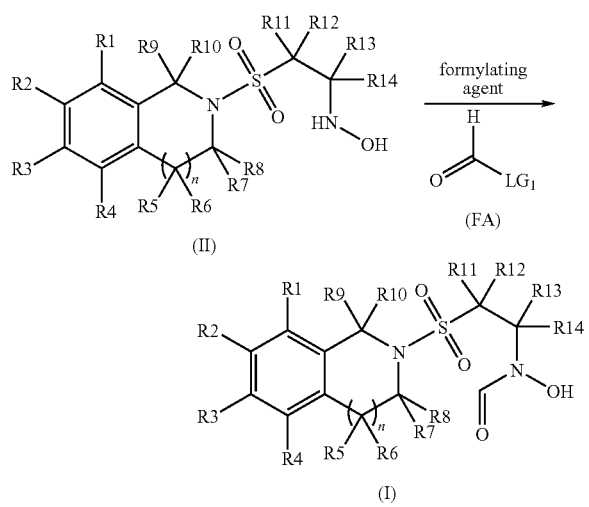

wherein $R^1, R^2, R^3, R^4, R^5, R^6, R^7, R^8, R^9, R^{10}, R^{11}, R^{12}, R^{13}, R^{14}$ and n are as defined in the description and LG1 is a leaving group such as —OH, —OAc, —OPiv, —OCH$_2$CN, —OCH$_2$CF$_3$, —OPh and —OPfp.

In another embodiment, the invention provides a process for the preparation of a sulfonamide derivative according to Formula (I), comprising the step of forming a compound of Formula (II). Examples of preferred route for formation of a compound of Formula (II) are described in the examples below.

In a further embodiment, the invention provides a process for the preparation of a sulfonamide derivative according to Formula (I), comprising the step of forming a compound of Formula (II) wherein the compound of Formula (II) is obtained through the reaction of a compound of Formula (III) with a hydroxylamine:

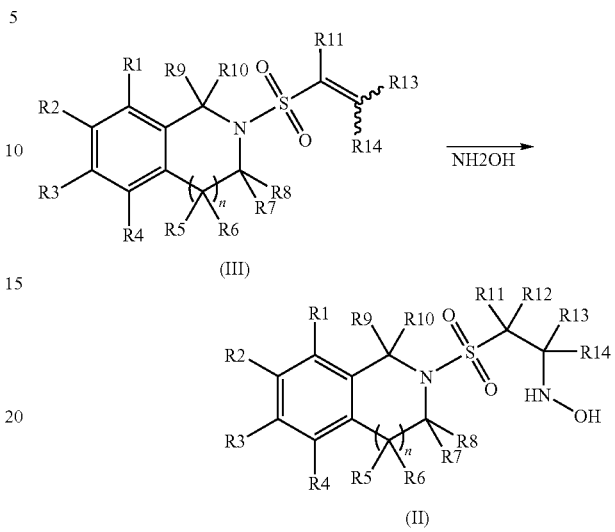

wherein $R^1, R^2, R^3, R^4, R^5, R^6, R^7, R^8, R^9, R^{10}, R^{11}, R^{12}, R^{13}, R^{14}$ and n are as defined in the description.

In another embodiment, the invention provides a compound according to Formula (II):

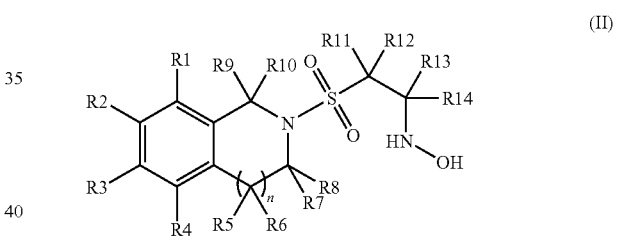

wherein $R^1, R^2, R^3, R^4, R^6, R^7, R^8, R^9, R^{10}, R^{11}, R^{12}, R^{13}, R^{14}$ and n are defined in the detailed description.

In a further embodiment, the invention provides a compound according to Formula (II) selected from the following group:

1-(3,4-dihydroisoquinolin-2(1H)-ylsulfonyl)-N-hydroxy-4-phenylbutan-2-amine;
2-(3,4-dihydroisoquinolin-2(1H)-ylsulfonyl)-1-[(4S)-2,2-dimethyl-1,3-dioxolan-4-yl]-N-hydroxyethanamine;
1-(3,4-dihydroisoquinolin-2(1H)-ylsulfonyl)-N-hydroxyheptan-2-amine;
1-cyclopropyl-2-(3,4-dihydroisoquinolin-2(1H)-ylsulfonyl)-N-hydroxyethanamine;
2-(3,4-dihydroisoquinolin-2(1H)-ylsulfonyl)-N-hydroxy-1-(2-thienyl)ethanamine;
1-(1,3-dihydro-2H-isoindol-2-ylsulfonyl)-N-hydroxy-4-phenylbutan-2-amine;
2-(3,4-dihydroisoquinolin-2(1H)-ylsulfonyl)-N-hydroxy-1-(3-thienyl)ethanamine;
1-(3,4-dihydroisoquinolin-2(1H)-ylsulfonyl)-N-hydroxy-3-methyl-3-morpholin-4-ylbutan-2-amine;
2-(3,4-dihydroisoquinolin-2(1H)-ylsulfonyl)-N-hydroxy-1-pyrimidin-2-ylethanamine;

2-(3,4-dihydroisoquinolin-2(1H)-ylsulfonyl)-N-hydroxy-1-pyridin-3-ylethanamine;

1-[(6,7-dimethoxy-3,4-dihydroisoquinolin-2(1H)-yl)sulfonyl]-N-hydroxy-4-phenylbutan-2-amine;

2-(3,4-dihydroisoquinolin-2(1H)-ylsulfonyl)-N-hydroxy-1-(6-methoxypyridin-3-yl)ethanamine;

2-[(6,7-dimethoxy-3,4-dihydroisoquinolin-2(1H)-yl)sulfonyl]-1-[(4S)-2,2-dimethyl-1,3-dioxolan-4-yl]-N-hydroxyethanamine.

In another embodiment, the invention provides a compound according to Formula (III):

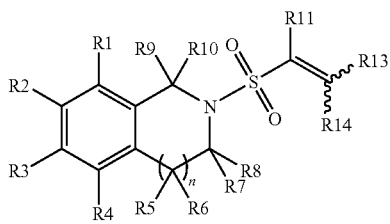

(III)

wherein $R^1$, $R^2$, $R^3$, $R^4$, $R^5$, $R^6$, $R^7$, $R^8$, $R^9$, $R^{10}$, $R^{11}$, $R^{13}$, $R^{14}$ and n are defined in the detailed description with the proviso that the compound according to Formula (III) is not 1,2,3,4-tetrahydro-2-[(2-phenylethenyl)sulfonyl]-isoquinoline.

In a further embodiment, the invention provides a compound according to Formula (III) selected from the following group:

2-{[4-phenylbut-1-en-1-yl]sulfonyl}-1,2,3,4-tetrahydroisoquinoline;

2-({2-[(4S)-2,2-dimethyl-1,3-dioxolan-4-yl]vinyl}sulfonyl)-1,2,3,4-tetrahydroisoquinoline;

2-[hept-1-en-1-ylsulfonyl]-1,2,3,4-tetrahydroisoquinoline;

2-{[2-cyclopropylvinyl]sulfonyl}-1,2,3,4-tetrahydroisoquinoline;

2-{[2-(2-thienyl)vinyl]sulfonyl}-1,2,3,4-tetrahydroisoquinoline;

2-{[4-phenylbut-1-en-1-yl]sulfonyl}isoindoline;

2-{[2-(3-thienyl)vinyl]sulfonyl}-1,2,3,4-tetrahydroisoquinoline;

2-{[3-methyl-3-morpholin-4-ylbut-1-en-1-yl]sulfonyl}-1,2,3,4-tetrahydroisoquinoline;

2-{[2-pyrimidin-2-ylvinyl]sulfonyl}-1,2,3,4-tetrahydroisoquinoline;

2-{[2-pyridin-3-ylvinyl]sulfonyl}-1,2,3,4-tetrahydroisoquinoline;

6,7-dimethoxy-2-{[4-phenylbut-1-en-1-yl]sulfonyl}-1,2,3,4-tetrahydroisoquinoline;

2-{[2-(6-methoxypyridin-3-yl)vinyl]sulfonyl}-1,2,3,4-tetrahydroisoquinoline;

2-({2-[(4S)-2,2-dimethyl-1,3-dioxolan-4-yl]vinyl}sulfonyl)-6,7-dimethoxy-1,2,3,4-tetrahydroisoquinoline.

In another embodiment, the invention provides a compound according to Formula (VI):

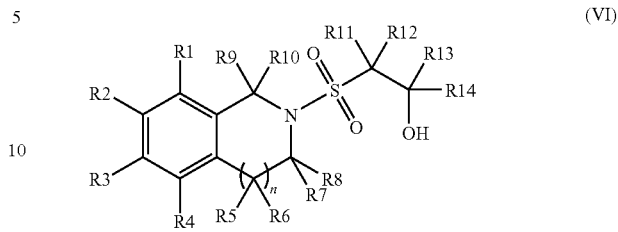

(VI)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and n are defined in the detailed description with the proviso that the compound according to Formula (VI) is not 2,3-dihydro-2-[(2-hydroxyethyl)sulfonyl]-1,1,3,3-tetramethyl-1H-Isoindole.

In a further embodiment, the invention provides a compound according to Formula (VI) selected from the following group:

1-(3,4-dihydroisoquinolin-2(1H)-ylsulfonyl)heptan-2-ol;

1-cyclopropyl-2-(3,4-dihydroisoquinolin-2(1H)-ylsulfonyl)ethanol;

1-(1,3-dihydro-2H-isoindol-2-ylsulfonyl)-4-phenylbutan-2-ol;

2-(3,4-dihydroisoquinolin-2(1H)-ylsulfonyl)-1-(6-methoxypyridin-3-yl)ethanol;

2-[(6,7-dimethoxy-3,4-dihydroisoquinolin-2(1H)-yl)sulfonyl]-1-[(4R)-2,2-dimethyl-1,3-dioxolan-4-yl]ethanol.

In another embodiment, the invention provides a compound according to Formula (VIII):

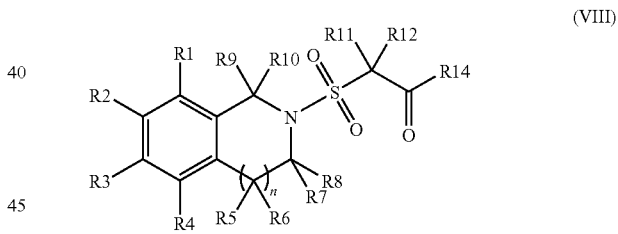

(VIII)

wherein $R^1$, $R^2$, $R^3$, $R^4$, $R^5$, $R^6$, $R^7$, $R^8$, $R^9$, $R^{10}$, $R^{11}$, $R^{12}$, $R^{14}$ and n are defined in the detailed description, with the proviso that the compound according to Formula (VIII) is not 2-[[2-(4-fluorophenyl)-2-oxoethyl]sulfonyl]-2,3-dihydro-1H-Isoindole, nor 1,2,3,4-tetrahydro-2-[(2-oxo-2-phenylethyl)sulfonyl]-isoquinoline.

In a further embodiment, the invention provides a compound according to Formula (VIII) selected from the following group:

1-(3,4-dihydroisoquinolin-2(1H)-ylsulfonyl)heptan-2-one;

1-cyclopropyl-2-(3,4-dihydroisoquinolin-2(1H)-ylsulfonyl)ethanone;

1-(1,3-dihydro-2H-isoindol-2-ylsulfonyl)-4-phenylbutan-2-one;

2-(3,4-dihydroisoquinolin-2(1H)-ylsulfonyl)-1-(6-methoxypyridin-3-yl)ethanone;

2-[(6,7-dimethoxy-3,4-dihydroisoquinolin-2(1H)-yl)sulfonyl]-1-[(4R)-2,2-dimethyl-1,3-dioxolan-4-yl]ethanone.

In another embodiment, the invention provides a compound according to Formula (IX):

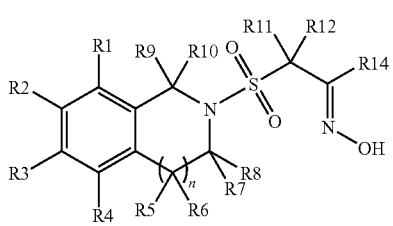

(IX)

wherein $R^1$, $R^2$, $R^3$, $R^4$, $R^5$, $R^6$, $R^7$, $R^8$, $R^9$, $R^{10}$ $R^{11}$, $R^{12}$, $R^{14}$ and n are defined in the detailed description.

In a further embodiment, the invention provides a compound according to Formula (IX) selected from the following group:
1-(3,4-dihydroisoquinolin-2(1H)-ylsulfonyl)heptan-2-one oxime;
1-cyclopropyl-2-(3,4-dihydroisoquinolin-2(1H)-ylsulfonyl)ethanone oxime;
1-(1,3-dihydro-2H-isoindol-2-ylsulfonyl)-4-phenylbutan-2-one oxime;
2-(3,4-dihydroisoquinolin-2(1H)-ylsulfonyl)-1-(6-methoxypyridin-3-yl)ethanone oxime;
2-[(6,7-dimethoxy-3,4-dihydroisoquinolin-2(1H)-yl)sulfonyl]-1-[(4S)-2,2-dimethyl-1,3-dioxolan-4-yl]ethanone oxime.

The compounds of invention have been named according the standards used in the program "ACD/Name" from Advanced Chemistry Development Inc., ACD/Labs (7.00 Release).

The compounds of Formula (I) are useful for the treatment and/or prophylaxis of autoimmune disorders, inflammatory diseases, cardiovascular diseases, neurodegenerative diseases, stroke, cancer and malignancy, allergic and dermatologic diseases, metabolic disorders, respiratory diseases, preterm labor, endometriosis and fibrosis, including multiple sclerosis, arthritis, rheumatoid arthritis, osteoarthritis, emphysema, chronic obstructive pulmonary disease, psoriasis, liver and pulmonary fibrosis.

In another embodiment, the compounds of the invention can be used in the treatment of autoimmune diseases, especially demyelinating diseases such as multiple sclerosis, alone or in combination with a co-agent useful in the treatment of autoimmune diseases, wherein the co-agent is for example selected from the following compounds:
(a) Interferons, e.g. pegylated or non-pegylated interferons, e.g. administered by sub-cutaneous, intramuscular or oral routes, preferably interferon beta;
(b) Glatiramer, e.g. in the acetate form;
(c) Immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH;
(d) Adenosine deaminase inhibitors, e.g. Cladribine;
(e) Inhibitors of VCAM-1 expression or antagonists of its ligand, e.g. antagonists of the α4/β1 integrin VLA-4 and/or alpha-4-beta-7 integrins, e.g. natalizumab (ANTEGRENO).

Further co-agents such as anti-inflammatory agents (in particular for demyelinating diseases such as multiple sclerosis) are described below:

A further anti-inflammatory agent is Teriflunomide which is described in WO-02080897

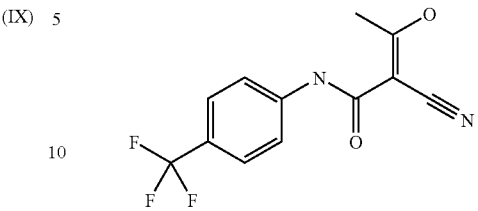

Still a further anti-inflammatory agent is Fingolimod which is described in EP-627406, WO 2004/028521 and WO 2004/089341.

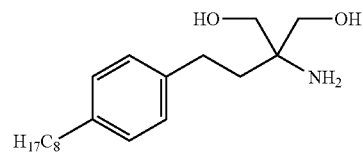

Still a further anti-inflammatory agent is Laquinimod which is described in WO 99/55678.

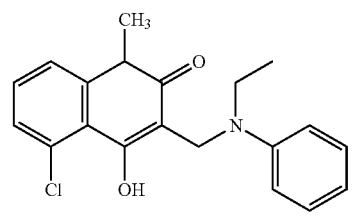

Still a further anti-inflammatory agent is Tensirolimus which is described in WO 0228866.

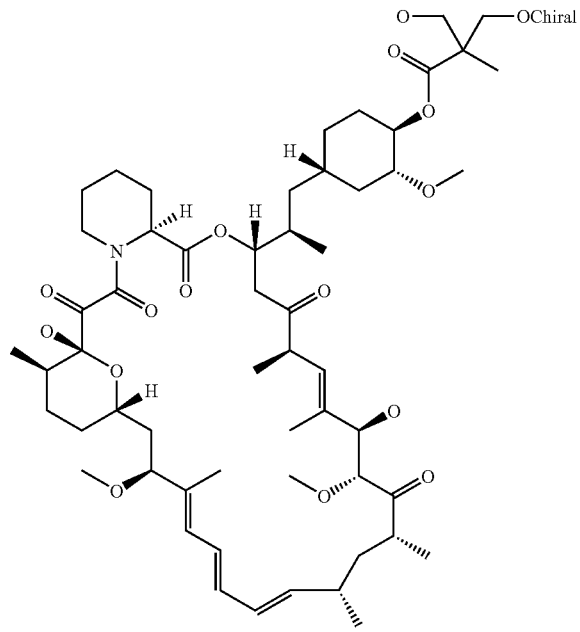

Still a further anti-inflammatory agent is Xaliprodene which is described in WO 9848802.

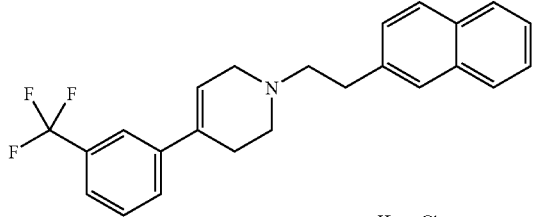

Still a further anti-inflammatory agent is Deskar Pirfenidone which is described in WO 03/068230.

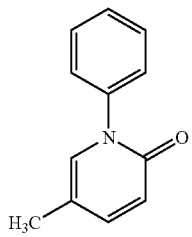

Still a further anti-inflammatory agent is the below benzothiazole derivative which is described in WO 01/47920.

Still a further anti-inflammatory agent is the below hydroxamic acid derivative which is described in WO 03070711.

Still a further anti-inflammatory agent is MLN3897 which is described in WO-2004043965.

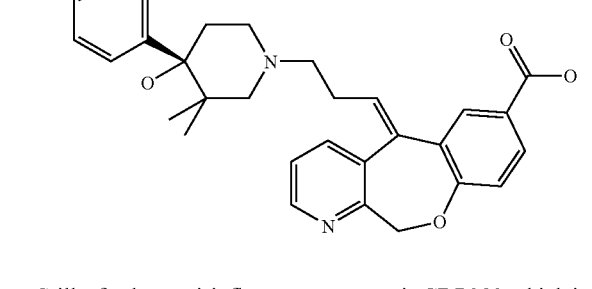

Still a further anti-inflammatory agent is CDP323 which is described in WO 9967230.

Still a further anti-inflammatory agent is Simvastatin which is described in WO 01/45698.

Still a further anti-inflammatory agent is Fampridine which is described in U.S. Pat. No. 5,540,938.

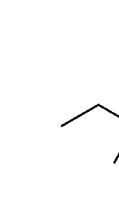

Compounds according to the present invention also comprise its tautomers, its geometrical isomers, its optically active forms as enantiomers, diastereomers and its racemate forms, as well as pharmaceutically acceptable salts thereof.

The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of the invention and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the derivative of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like.

Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the sulfonamide derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel derivatives according to Formula (I) can be prepared from readily available starting materials by several synthetic approaches, using both solution-phase and solid-phase chemistry protocols. Examples of synthetic pathways for the will be described.

aq (aqueous), hr (hour), g (gram), L (liter), mg (milligram), MHz (Megahertz), min. (minute), mm (millimeter), mmol (millimole), mM (millimolar), M (molar), m.p. (melting point), eq (equivalent), ml (milliliter), μl (microliter), pet. ether (petrol ether), Ac (acetyl), ACN (acetonitrile), Bu (butyl), chex (cyclohexane), DCM (dichloromethane), DIEA (diisopropylethylamine), DMF (dimethylformamide), DMSO (dimethylsulfoxide), ESI (electro-spray ionization), Et (ethyl), HPLC (high performance liquid chromatography), iPr (isopropyl), Kg (kilo), LC (liquid chromatography), LDA (lithium diisopropylamide), LiHMDS (lithium bis(trimethylsilyl)amide), Me (methyl), MS (mass spectrometry), MTBE (methyl tert-butyl ether), NMR (nuclear magnetic resonance), Piv (pivalyl), Pfp (pentafluorophenyl), RT (room temperature), Rt (retention time), TEA (triethylamine), THF (tetrahydrofuran), TLC (thin layer chromatography), UV (Ultraviolet).

Synthetic Approaches:

Generally, compounds of Formula (I) may be obtained by formylation of a compound of Formula (II) wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and n are defined as above (Scheme 1 below).

General protocols for such a formylation are given below in the examples. The use of formylating agents (FA) are well known from those skilled in the art, wherein LG1 is a leaving group such as —OH, —OAc, —OPiv, —OCH$_2$CN, —OCH$_2$CF$_3$, —OPh and —OPfp. For example, a formylating agent may be obtained by reaction between formic acid and acetic anhydride.

Scheme 1

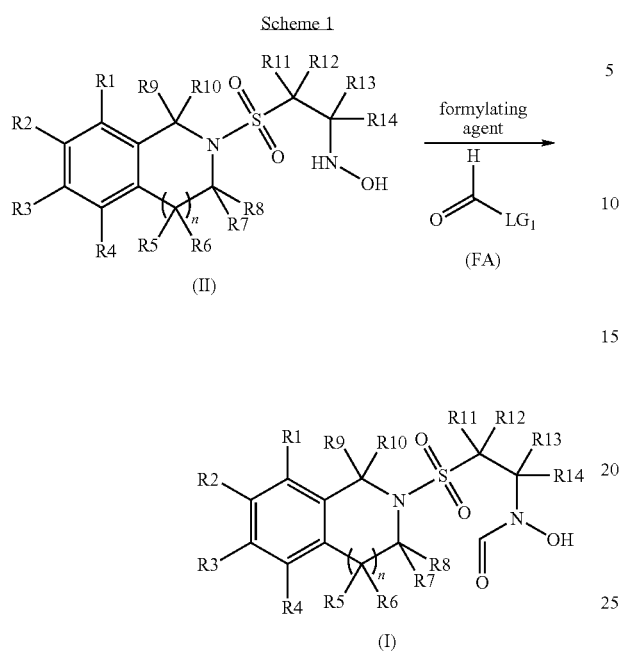

A preferred synthetic pathway for the preparation of a compound of Formula (II) consists in the reaction of hydroxylamine with a compound of Formula (III) wherein $R^1$, $R^2$, $R^3$, $R^4$, $R^5$, $R^6$, $R^7$, $R^8$, $R^9$, $R^{10}$, $R^{11}$, $R^{13}$, $R^{14}$ and n are as defined above, in a suitable solvent such as THF at a temperature between 0° C. and 100° C. (Scheme 2 below). When $R^{12}$ is an atom of hydrogen, a compound of Formula (III) may be obtained by reaction between a carbonyl derivative of Formula (V) and a sulfonamide of Formula (IV) wherein $R^1$, $R^2$, $R^3$, $R^4$, $R^5$, $R^6$, $R^7$, $R^8$, $R^9$, $R^{10}$, $R^{11}$, $R^{13}$, $R^{14}$ and n are as defined above.

Preferred conditions involve the deprotonation of a sulfonamide of Formula (IV) with a base, such as LiHMDS, LDA or BuLi, followed by the reaction with a chlorophosphate, such as diethylchlorophosphate, and a carbonyl derivative of Formula (V), such as 3-phenylpropionaldehyde, in a suitable solvent, such as THF.

Scheme 2

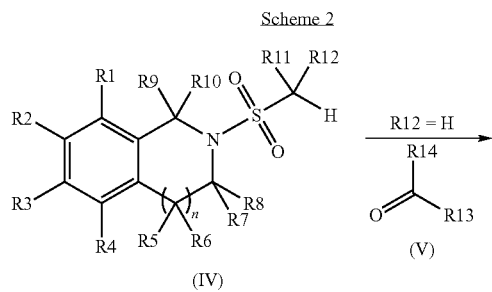

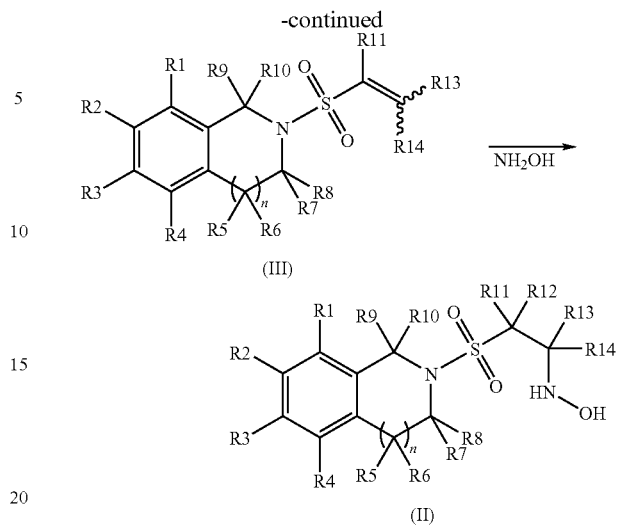

Alternative pathways for the preparation of compound of Formula (II) are described in Scheme 3 below.

A first alternative pathway consists in the formation of an alcohol of Formula (VI) by the reaction between a carbonyl derivative of Formula (V) and a sulfonamide of Formula (IV) wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and n are as defined above, under basic conditions, such as LiHMDS, in a suitable solvent such as THF. Then, the alcohol of Formula (VI) can be transformed into compound of Formula (III) wherein $R^1$, $R^2$, $R^3$, $R^4$, $R^5$, $R^6$, $R^7$, $R^8$, $R^9$, $R^{10}$, $R^{11}$, $R^{13}$, $R^{14}$, and n are as defined above and $R^{12}$ is an atom of hydrogen, by an elimination reaction in the presence or not of a reactive such as MsCl, TsCl or $Tf_2O$ with or without an additive such as a base ($Et_3N$, DIEA). Then, compound of Formula (III) can be transformed into a compound of Formula (II) as described above.

As an alternative pathway, the alcohol of Formula (VI) can be transformed into a compound of Formula (II) wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and n are as defined above by transformation of the hydroxyl moiety into a leaving group, such as a mesyl or a tosyl moiety, followed by displacement by hydroxylamine in a suitable solvent such as THF.

An alternative route for the preparation of compounds of Formula (II) may start with the reaction of a sulfonamide of Formula (IV), previously deprotonated as described above, with an ester of Formula (VII) wherein R is a $C_1$-$C_6$ alkyl or $C_3$-$C_8$ cycloalkyl or a benzyl and $R^{14}$ is defined as above to lead to a ketone of Formula (VIII) wherein $R^1$, $R^2$, $R^3$, $R^4$, $R^5$, $R^6$, $R^7$, $R^8$, $R^9$, $R^{10}$, $R^{11}$, $R^{12}$, $R^{14}$ and n are as defined above (Scheme 3 below) Then, a ketone of Formula (VIII) may be transformed in an oxime of Formula (IX) wherein $R^1$, $R^2$, $R^3$, $R^4$, $R^5$, $R^6$, $R^7$, $R^8$, $R^9$, $R^{10}$, $R^{11}$, $R^{12}$ and n are as defined above by reaction with hydroxylamine. Previous oxime of Formula (IX) may be transformed in a compound of Formula (II) by the use of a suitable reducing agent. Alternatively, a ketone of Formula (VIII) may be transformed in an alcohol of Formula (VI) wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and n are as defined above by the use of a suitable reducing agent, which may be transformed in a compound of Formula (II) as described above.

Scheme 3

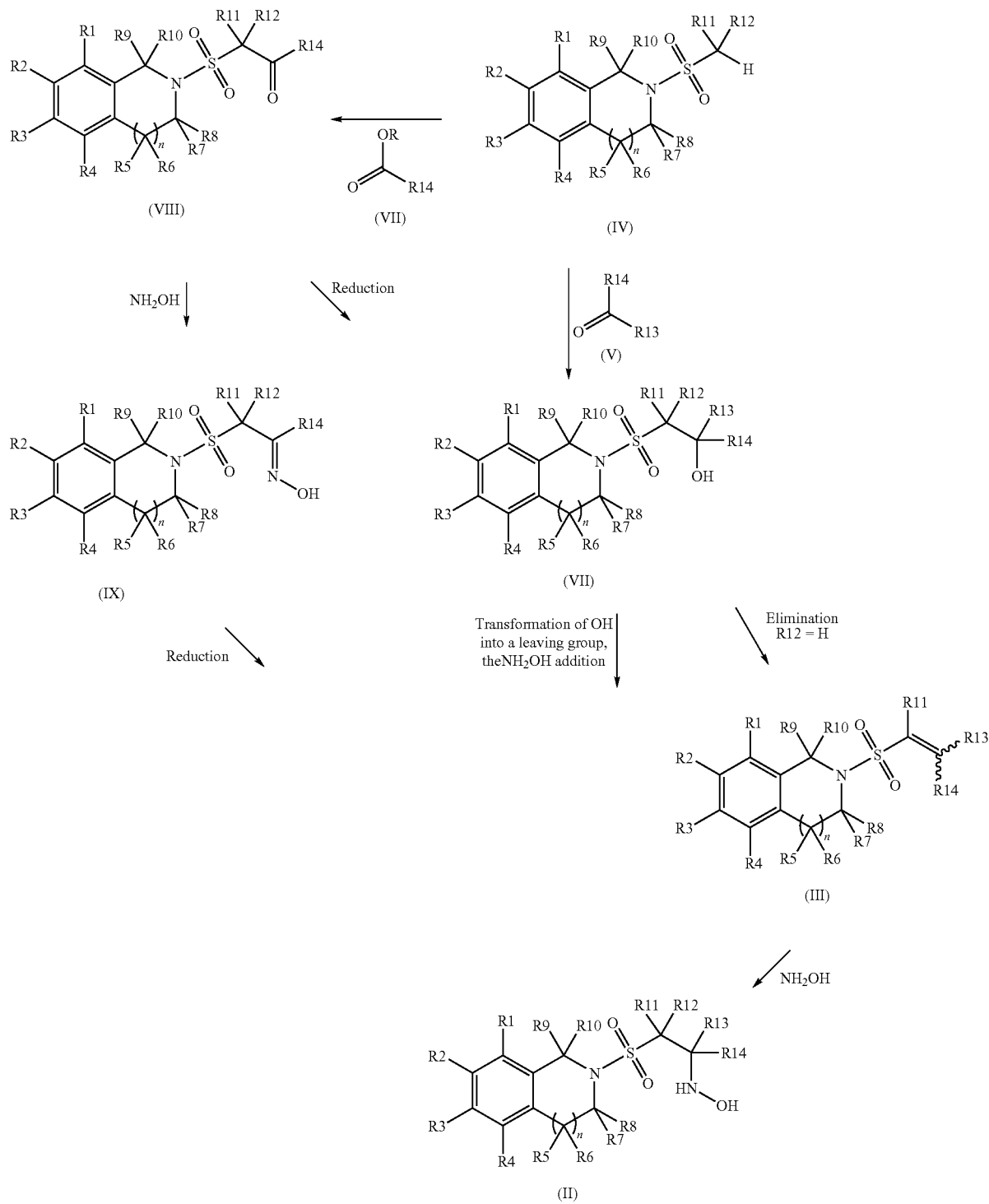

Intermediates of Formula (IV) are prepared by reaction of a compound of Formula (X) wherein $R^1$, $R^2$, $R^3$, $R^4$, $R^5$, $R^6$, $R^7$, $R^8$, $R^9$, $R^{10}$ and n are defined as above with a sulfonyl chloride of Formula (XI) wherein $R^{11}$ and $R^{12}$ are defined as above in conditions well known to those skilled in the art (Scheme 4 below). An alternative pathway for the preparation of compounds of Formula (IV) could start with the reaction between amines of Formula (XII) wherein $R^1$, $R^2$, $R^3$, $R^4$, $R^5$, $R^6$, $R^7$, $R^8$ and n are defined as above and sulfonyl chloride derivatives of Formula (XI) wherein $R^{11}$ and $R^{12}$ are defined as above to give sulfonamide derivatives of Formula (XIII) wherein $R^1$, $R^2$, $R^3$, $R^4$, $R^5$, $R^6$, $R^7$, $R^8$, $R^{11}$, $R^{12}$ and n are defined as above. Then, sulfonamide derivatives of Formula (XIII) could be cyclized in presence of carbonyl derivatives of Formula (XIV) (or precursors of carbonyl derivatives such as acetal) in acidic conditions, such as Lewis acids, to give compounds of Formula (IV) wherein $R^1$, $R^2$, $R^3$, $R^4$, $R^5$, $R^6$, $R^7$, $R^8$, $R^9$, $R^{10}$ $R^{11}$, $R^{12}$ and n are defined as above (Shin et al., *Tetrahedron Lett.* 2001, 42, 6251-6253).

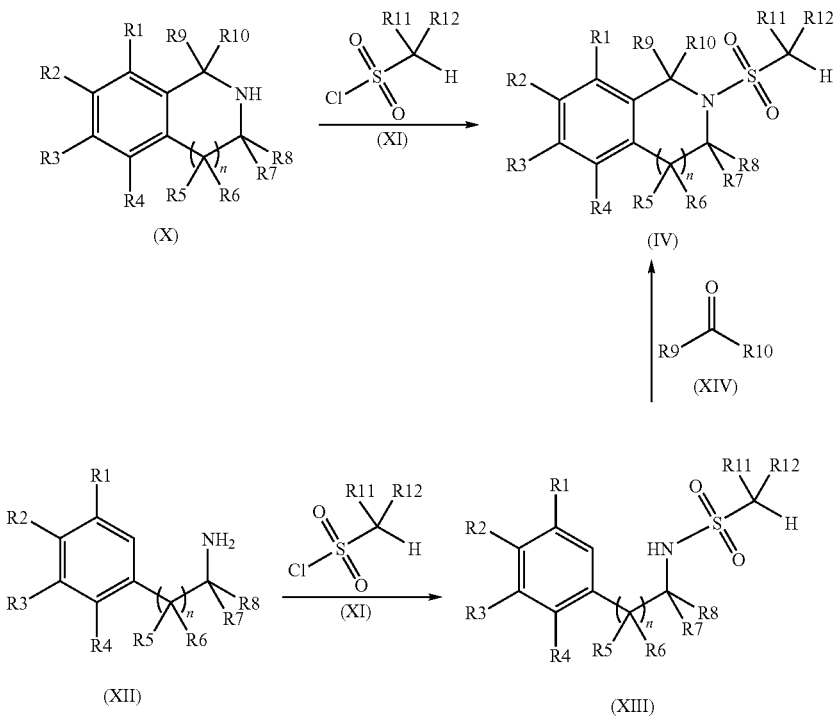

Intermediates of Formulae (V), (VII), (X), (XI) and (XII) are commercially available or may be prepared using conditions well known by those skilled in the art. For example, intermediate of Formula (X) may be prepared following procedures described in Cho et al., 2005, *Bioorg. Med. Chem. Lett.*, 185-189 or in Bailey et al., 1973, *J. Med. Chem.*, 151-156.

According to a further general process, compounds of Formula (I) can be converted to alternative compounds of Formula (I), employing suitable interconversion techniques well known by a person skilled in the art. Alternatively, any compounds of Formulae (II), (III), (IV), (VI), (VIII) and (IX) may be converted to alternative compounds of Formulae (II), (III), (IV), (VI), (VIII) and (IX) respectively, employing suitable interconversion techniques well known by those skilled in the art.

Compounds of Formula (I) could be prepared with or without isolation of intermediates of Formula II, III, IV, VI, VIII and IX. A preferred synthetic method for the preparation of compounds of Formula (I) starts from compounds of Formula (IV) which has the advantage that synthesis of compounds of Formula (I) can be achieved without isolation of intermediates as described below in examples (Scheme 2).

Compounds of Formula (I) and its precursors of Formulae (II) and (VI) contain at least one chiral center, and all individual optically active forms and combinations of these are disclosed as individual and specific embodiments of the invention, as well as their corresponding racemates. The processes outlined in the above Schemes, in particular Schemes 1 and 2, afford compounds of Formula (I) and its precursors of Formulae (II) and (VI), in racemic form or as mixtures of diastereoisomers, in cases where additional chiral centers are present. Pure stereoisomers can be obtained from stereoisomer mixtures using procedures well known to those skilled in the art, including for example separation of enantiomers by chiral HPLC, or crystallization and/or chromatography for mixture of diastereoisomers. Alternatively, a mixture of enantiomers can be separated by the formation of diastereoisomeric derivatives having convenient optically active auxiliary moiety, followed by separation of the formed diastereoisomers and then cleavage of the chiral auxiliary.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999. Those skilled in the art will recognize that certain reactions are best carried out when potentially reactive functionality on the molecule is masked or protected, thus avoiding side reactions and/or increasing the yield of the reaction. Examples of protecting group moieties may be found in Philip J. Kocienski, 1994 above and in Greene et al., 1999, above. The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

The following reagents commercially available were used: 1,2,3,4-tetrahydroisoquinoline (Fluka), diisopropylethylamine or DIEA (Fluka), methane sulfonyl chloride (Aldrich), lithium bis(trimethylsilyl)amide or LiHMDS (Aldrich), diethyl chlorophosphate (Aldrich), 3-phenylpropionaldehyde (Aldrich), hydroxylamine or $NH_2OH$ (Fluka), acetic anhydride (Fluka), 2,3-O-isopropylidene-D-glyceraldehyde (Interchim), hexanal (Aldrich), cyclopropanecarboxaldehyde (Aldrich), 2-thiophene carboxaldehyde (Fluka), isoindoline (Aldrich), 3-thiophenecarboxaldehyde (Aldrich), 2-methyl-2-morpholinopropanal (Bionet), 5-pyrimidinecarboxaldehyde (Apollo), 3-pyridine carboxaldehyde (Fluka), 6,7-dimethoxy-1,2,3,4-tetrahydroisoquinoline hydrochloride (Aldrich), 6-methoxy-3-pyridinecarboxaldehyde (Aldrich), aminoacetaldehyde dimethylacetal (Aldrich), 1-benzyl-piperidine-4-carbaldehyde (J & W Pharmlab), benzyloxyacetaldehyde (Aldrich), boron trifluoride diethyl ether complex (Aldrich), 7-bromo-1,2,3,4-tetrahydroisoquinoline hydrochloride (Arch), 4-chlorophenethylamine (Aldrich), cyclopentanecarboxaldehyde (Aldrich), cyclopentanone (Fluka), 3,3-dimethylbutyraldehyde (Fluka), 3,4-dichlorophenethylamine (Acros), 2-ethylbutyraldehyde (Aldrich), ethyl isobutyrate (Aldrich), ethyl 2-formyl-1-cyclopropanecarboxylate (Aldrich), 5-fluoro-2,3-dihydro-1H-isoindole hydrochloride (Astatech), 4-fluorophenylboronic acid (Aldrich), 7-fluoro-1,2,3,4-tetrahydroisoquinoline hydrochloride (Arch), 2-formyl-pyrrolidine-1-carboxylic acid tert-butyl ester (Pharmacore), 3-(2-furyl) acrolein (Acros), 3-furaldehyde (Aldrich), glycolaldehyde (ICN), 3-hydroxyphenylboronic acid (Aldrich), 4-isopropyl benzaldehyde (Aldrich), isobutyraldehyde (Aldrich), isopropyl iodide (Aldrich), isovaleraldehyde (Aldrich), lithium aluminium hydride (Fluka), 7-methoxy-1,2,3,4-tetrahydroisoquinoline hydrochloride (Arch), 3-(methylthio) propionaldehyde (Aldrich), methyl phenoxyacetate (Aldrich), methyl tetrahydro-2H-pyran-4-carboxylate (Fluka), methyl 3-(3-pyridyl)propionate (Lancaster), oxalyl chloride (Aldrich), 2-pentynyl chloride (TCI), phenylboronic acid (Aldrich), propyl iodide (Aldrich), pyridine-4-boronic acid (Aldrich), sodium borohydride (Fluka), 3-[(tert-butyldimethylsilyl)oxy]-1-propanal (Toronto), 4-(tert-butyl) phenethylamine (Emkachem), 3-thienylboronic acid (Aldrich), 1,3,5-trioxane (Fluka), trimethylacetaldehyde (Aldrich), triethylamine (Fluka), 7-trifluoromethyl-1,2,3,4-tetrahydroisoquinoline hydrochloride (Arch), 4,4,4-trifluorobutyraldehyde (ABCR).

Example 1

Formation of N-{1-[(3,4-dihydroisoquinolin-2(1H)-ylsulfonyl)methyl]-3-phenylpropyl}-N-hydroxyformamide (1)

Step a) Formation of 2-(methylsulfonyl)-1,2,3,4-tetraisoquinoline

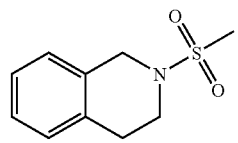

A solution of 1,2,3,4-tetrahydroisoquinoline (10.0 g, 75 mmol) and DIEA (15.3 ml, 90 mmol) in anhydrous DCM (200 ml) was cooled at 0° C. and methanesulfonyl chloride (7.0 ml, 90 mmol) was added dropwise. The resulting mixture was stirred at 0° C. for 1 hour. Then the reaction mixture was washed with a 1N aqueous solution of HCl (150 ml) and a saturated aqueous solution of $NaHCO_3$ (150 ml). The aqueous layers were extracted with DCM (2×100 ml). The organic layers were combined, dried ($MgSO_4$) and the volume of solvent was reduced to 40 ml by evaporation under reduced pressure. A solid started to precipitate out and pentane was added to finish the precipitation. The solid was filtered, washed with pentane (2×) and dried under reduced pressure to give 15.7 g (98%) of the title compound as a yellow powder. HPLC, Rt: 2.6 min (purity: 95.3%). LC/MS, $M^+(ESI)$: 212.2.

Step b) Formation of N-{1-[(3,4-dihydroisoquinolin-2(1H)-ylsulfonyl)methyl]-3-phenylpropyl}-N-hydroxyformamide

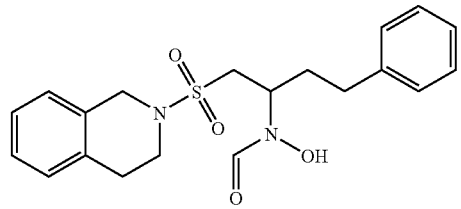

A solution of 2-(methylsulfonyl)-1,2,3,4-tetraisoquinoline (500 mg, 2.37 mmol) was prepared in anhydrous THF (20 ml) and cooled at 0° C. A solution of LiHMDS (1M in THF, 5.2 ml, 5.2 mmol) was added dropwise. After 5 min., diethyl chlorophosphate (0.34 ml, 2.37 mmol) was added. After 5 min., 3-phenylpropionaldehyde (0.37 ml, 2.84 mmol) was added and the reaction mixture was stirred at room temperature for 40 min. Then a 50% aqueous solution of $NH_2OH$ (2.1 ml) was added and the resulting biphasic mixture was heated at 60° C. for 2.5 hours. Brine (20 ml) was added and the layers were separated. The aqueous layer was extracted with EtOAc (2×20 ml). The organic layers were combined, dried ($MgSO_4$) and the solvents were removed under reduced pressure to give a yellow oil. A mixture of formic acid (7 ml) and acetic anhydride (1.7 ml) was stirred at 0° C. for 30 min., then a solution of the previous oil in anhydrous THF (15 ml) was added and the resulting mixture was stirred at 0° C. for 30 min. The mixture was evaporated under reduced pressure.

The residue was taken up in MeOH (10 ml) and heated at 60° C. for 30 min. The mixture was evaporated under reduced pressure to give a yellow oil, which was taken up in EtOAc (20 ml) and washed with a saturated aqueous solution of NaHCO₃ (20 ml). The aqueous layer was extracted with EtOAc (2×20 ml). The organic layers were combined, dried (MgSO₄) and the solvent was removed under reduced pressure to give a yellow oil. After purification by flash chromatography on silica gel (gradient cHex:EtOAc 4:1 to pure EtOAc) followed by a precipitation in EtOAc (6 ml), the title compound (1) was obtained as a white powder (364 mg, 40% yield). HPLC, Rt: 3.8 min (purity: 100%). LC/MS, M⁺(ESI): 389.3, M⁻(ESI): 387.2.

Example 2

Formation of N-{2-(3,4-dihydroisoquinolin-2(1H)-ylsulfonyl)-1-[(4S)-2,2-dimethyl-1,3-dioxolan-4-yl]ethyl}-N-hydroxyformamide (2)

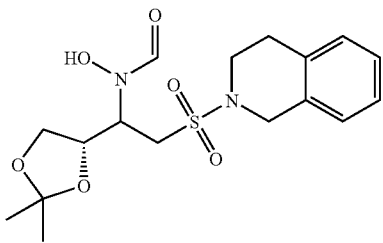

The title compound was prepared following procedure described in Example 1 step b), but starting from 2,3-O-isopropylidene-D-glyceraldehyde. After purification by precipitation in EtOAc, the title compound (2) was obtained as a white powder (392 mg, 43% yield). HPLC, Rt: 3.0 min (purity: 95.0%). LC/MS, M⁺(ESI): 385.3, M⁻(ESI): 383.3.

Example 3

Formation of N-{1-[(3,4-dihydroisoquinolin-2(1H)-ylsulfonyl)methyl]hexyl}-N-hydroxyformamide (3)

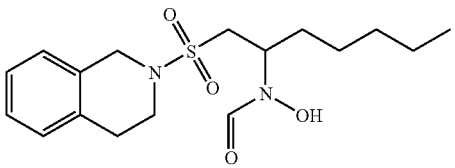

The title compound was prepared following procedure described in Example 1 step b), but starting from hexanal. After purification by precipitation in EtOAc, the title compound (3) was obtained as a white powder (546 mg, 65% yield). HPLC, Rt: 3.8 min (purity: 98.5%). LC/MS, M⁺(ESI): 355.3, M⁻(ESI): 353.3.

Example 4

Formation of N-[1-cyclopropyl-2-(3,4-dihydroisoquinolin-2(1H)-yl sulfonyl)ethyl]-N-hydroxyformamide (4)

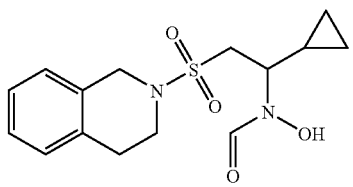

The title compound was prepared following procedure described in Example 1 step b), but starting from cyclopropanecarboxaldehyde. After purification by precipitation in EtOAc: pentane 1:1, the title compound (4) was obtained as a white powder (380 mg, 50% yield). HPLC, Rt: 2.8 min (purity: 100%). LC/MS, M⁺(ESI): 325.2, M⁻(ESI): 323.2.

Example 5

Formation of N-[2-(3,4-dihydroisoquinolin-2(1H)-ylsulfonyl)-1-(2-thienyl)ethyl]-N-hydroxyformamide (5)

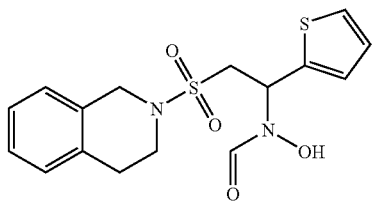

The title compound was prepared following procedure described in Example 1 step b), but starting from 2-thiophenecarboxaldehyde. After purification by flash chromatography on silica gel (gradient cHex:EtOAc 4:1 to EtOAc) followed by a precipitation in EtOAc/cHex, the title compound (5) was obtained as an off-white powder (371 mg, 43% yield). HPLC, Rt: 3.3 min (purity: 98.6%). LC/MS, M⁺(ESI): 367.2, M⁻(ESI): 365.2.

Example 6

Formation of N-{1-[(1,3-dihydro-2H-isoindol-2-ylsulfonyl)methyl]-3-phenylpropyl}-N-hydroxyformamide (6)

Step a) Formation of 2-(methylsulfonyl)isoindoline

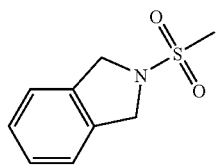

The title compound was prepared following procedure described in Example 1 step a), but starting from isoindoline.

The title compound was obtained as a grey powder (2.53 g, 76% yield). HPLC, Rt: 2.1 min (purity: 100%). LC/MS, M$^+$(ESI): 198.1.

Step b) Formation of N-{1-[(1,3-dihydro-2H-isoindol-2-ylsulfonyl)methyl]-3-phenylpropyl}-N-hydroxyformamide

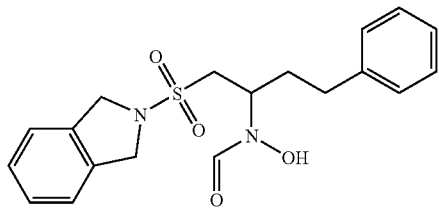

The title compound was prepared following procedure described in Example 1 step b), but starting from 2-(methylsulfonyl)isoindoline. After purification by precipitation in EtOAc, the title compound (6) was obtained as a white powder (448 mg, 47% yield). HPLC, Rt: 3.7 min (purity: 100%). LC/MS, M$^+$(ESI): 375.3, M$^-$(ESI): 373.3.

Example 7

Formation of N-[2-(3,4-dihydroisoquinolin-2(1H)-ylsulfonyl)-1-(3-thienyl)ethyl]-N-hydroxyformamide (7)

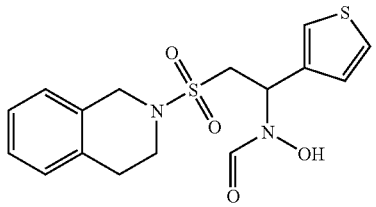

The title compound was prepared following procedure described in Example 1 step b), but starting from 3-thiophenecarboxaldehyde. After purification by flash chromatography on silica gel (gradient cHex:EtOAc 4:1 to pure EtOAc) followed by a precipitation in EtOAc/cHex, the title compound (7) was obtained as an off-white powder (334 mg, 39% yield). HPLC, Rt: 3.2 min (purity: 95.4%). LC/MS, M$^+$(ESI): 367.2, M$^-$(ESI): 365.2.

Example 8

Formation of N-{1-[(3,4-dihydroisoquinolin-2(1H)-ylsulfonyl)methyl]-2-methyl-2-morpholin-4-ylpropyl}-N-hydroxyformamide (8)

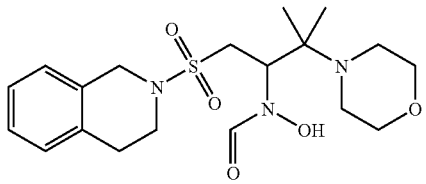

The title compound was prepared following procedure described in Example 1 step b), but starting from 2-methyl-2-morpholinopropanal. After purification by precipitation in EtOAc, the title compound (8) was obtained as a white powder (294 mg, 30% yield). HPLC, Rt: 2.1 min (purity: 99.9%). LC/MS, M$^+$(ESI): 412.4, M$^-$(ESI): 410.3.

Example 9

Formation of N-[2-(3,4-dihydroisoquinolin-2(1H)-ylsulfonyl)-1-pyrimidin-5-ylethyl]-N-hydroxyformamide (9)

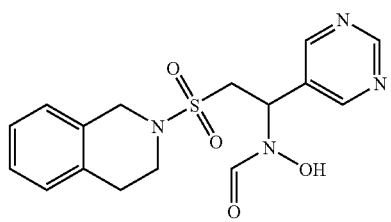

The title compound was prepared following procedure described in Example 1 step b), but starting from 5-pyrimidinecarboxaldehyde. After purification by precipitation in EtOAc/cHex, followed by recrystallization from iPrOH, the title compound (9) was obtained as a yellow powder (68 mg, 8% yield). HPLC, Rt: 2.4 min (purity: 90.5%). LC/MS, M$^+$(ESI): 363.2, M$^-$(ESI): 361.1.

Example 10

Formation of N-[2-(3,4-dihydroisoquinolin-2(1H)-ylsulfonyl)-1-pyridin-3-ylethyl]-N-hydroxyformamide (10)

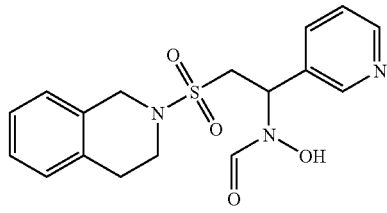

The title compound was prepared following procedure described in Example 1 step b), but starting from 3-pyridinecarboxaldehyde. After purification by precipitation in EtOAc/pentane, the title compound (10) was obtained as an off-white powder (153 mg, 18% yield). HPLC, Rt: 1.9 min (purity: 91.6%). LC/MS, M$^+$(ESI): 362.3, M$^-$(ESI): 360.3.

Example 11

Formation of N-[2-(3,4-dihydroisoquinolin-2(1H)-ylsulfonyl)-1-pyridin-3-ylethyl]-N-hydroxyformamide, hydrochloride salt (11)

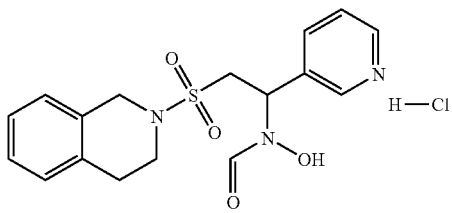

An excess of a solution of HCl (4N in 1,4-dioxane) was added to a solution of N-[2-(3,4-dihydroisoquinolin-2(1H)-ylsulfonyl)-1-pyridin-3-ylethyl]-N-hydroxyformamide (55 mg, 80% purity) in 1,4-dioxane. A solid precipitated out. The supernatant was removed by decantation, then the solid was washed by decantation with Et2O (2×) and dried under reduced pressure to give the title compound (11) as an off-white powder (25 mg, 40% yield). HPLC, Rt: 1.9 min (purity: 83.0%). LC/MS, M$^+$(ESI): 362.3, M$^-$(ESI): 360.3.

Example 12

Formation of N-(1-{[(6,7-dimethoxy-3,4-dihydroisoquinolin-2(1H)-yl) sulfonyl]methyl}-3-phenylpropyl)-N-hydroxyformamide (12)

Step a) Formation of 6,7-dimethoxy-2-(methylsulfonyl)-1,2,3,4-tetrahydroisoquinoline

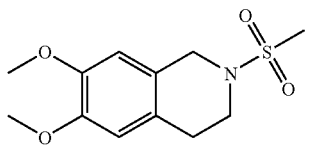

The title compound was prepared following procedure described in Example 1 step a), but starting from 6,7-dimethoxy-1,2,3,4-tetrahydroisoquinoline hydrochloride and one additional equivalent of DIEA. The title compound was obtained as a pale yellow powder (930 mg, 79% yield). HPLC, Rt: 2.3 min (purity: 99.2%). LC/MS, M$^+$(ESI): 272.2.

Step b) Formation of N-(1-{[(6,7-dimethoxy-3,4-dihydroisoquinolin-2(1H)-yl)sulfonyl]methyl}-3-phenylpropyl)-N-hydroxyformamide

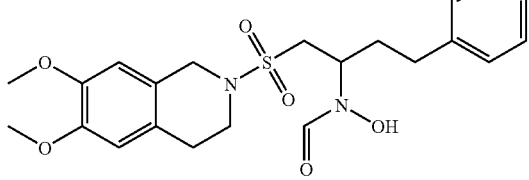

The title compound was prepared following procedure described in Example 1 step b), but starting from 6,7-dimethoxy-2-(methylsulfonyl)-1,2,3,4-tetrahydroisoquinoline. After purification by precipitation in EtOAc/pentane, the title compound (12) was obtained as a white powder (366 mg, 44% yield). HPLC, Rt: 3.4 min (purity: 99.7%). LC/MS, M$^+$(ESI): 449.4, M$^-$(ESI): 447.4.

Example 13

Formation of N-[2-(3,4-dihydroisoquinolin-2(1H)-ylsulfonyl)-1-(6-methoxypyridin-3-yl)ethyl]-N-hydroxyformamide (13)

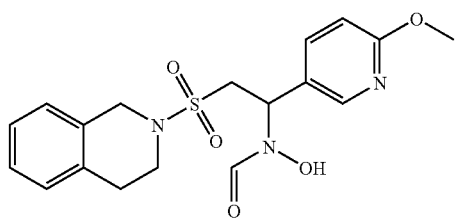

The title compound was prepared following procedure described in Example 1 step b), but starting from 6-methoxy-3-pyridinecarboxaldehyde. After purification by flash chromatography on silica gel (gradient cHex:EtOAc 4:1 to EtOAc), followed by a precipitation in EtOAc/pentane, the title compound (14) was obtained as an orange powder (135 mg, 15% yield). HPLC, Rt: 2.8 min (purity: 98.4%). LC/MS, M$^+$(ESI): 392.4, M$^-$(ESI): 390.3.

Example 14

Formation of N-{2-[(6,7-dimethoxy-3,4-dihydroisoquinolin-2(1H)-yl) sulfonyl]-1-[(4S)-2,2-dimethyl-1,3-dioxolan-4-yl]ethyl}-N-hydroxyformamide (14)

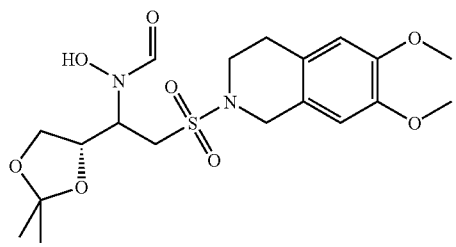

The title compound was prepared following procedure described in Example 1 step b), but starting from 6,7-dimethoxy-2-(methylsulfonyl)-1,2,3,4-tetrahydroisoquinoline and 2,3-O-isopropylidene-D-glyceraldehyde. After purification by crystallization at −20° C. in EtOAc/pentane, the title compound (14) was obtained as a white powder (117 mg, 18% yield). HPLC, Rt: 2.6 min (purity: 97.3%). LC/MS, M$^+$(ESI): 445.4, M$^-$(ESI): 443.4. $^1$H.

Example 15

Formation of N-{1-cyclopentyl-2-[(6,7-dimethoxy-3,4-dihydroisoquinolin-2(1H)-yl)sulfonyl]ethyl}-N-hydroxyformamide (15)

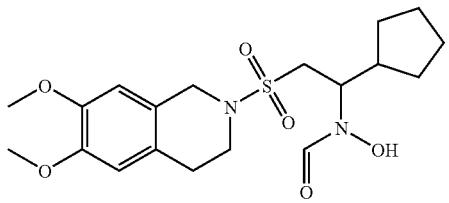

The title compound was prepared following procedure described in Example 1 step b), but starting from 6,7-dimethoxy-2-(methylsulfonyl)-1,2,3,4-tetrahydroisoquinoline and cyclopentanecarboxaldehyde. After purification by crystallization in EtOAc/pentane, the title compound (15) was obtained as a white powder (400 mg, 53%). HPLC, Rt: 2.9 min (purity: 96.0%). LC/MS, M$^+$(ESI): 413.5, M$^-$(ESI): 411.4.

Example 16

Formation of N-{2-(1,3-dihydro-2H-isoindol-2-yl-sulfonyl)-1-[(4S)-2,2-dimethyl-1,3-dioxolan-4-yl]ethyl}-N-hydroxyformamide (16)

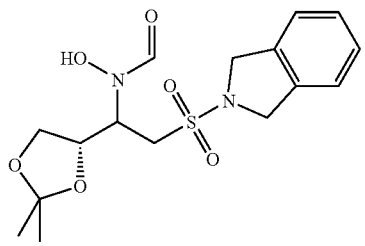

The title compound was prepared following procedure described in Example 1 step b), but starting from 2-(methylsulfonyl)isoindoline and 2,3-O-isopropylidene-D-glyceraldehyde. After purification by crystallization in EtOAc/pentane, the title compound (16) was obtained as a grey powder (75 mg, 14%). HPLC, Rt: 2.4 min (purity: 98.0%). LC/MS, M$^+$(ESI): 371.1, M$^-$(ESI): 369.1.

Example 17

Formation of N-(1-{[(6,7-dimethoxy-3,4-dihydroisoquinolin-2(1H)-yl)sulfonyl]methyl}-2-ethylbutyl)-N-hydroxyformamide (17)

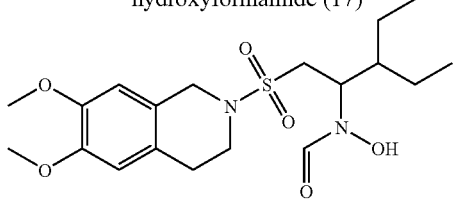

The title compound was prepared following procedure described in Example 1 step b), but starting from 6,7-dimethoxy-2-(methylsulfonyl)-1,2,3,4-tetrahydroisoquinoline and 2-ethylbutyraldehyde. The addition of hydroxylamine required 48 hrs and the use of 30 equivalents. After purification by crystallization in EtOAc/cHex, the title compound (17) was obtained as a white powder (490 mg, 64%). HPLC, Rt: 3.2 min (purity: 95.7%). LC/MS, M$^+$(ESI): 415.4, M$^-$(ESI): 413.3.

Example 18

Formation of N-{1-[(4S)-2,2-dimethyl-1,3-dioxolan-4-yl]-2-[(6-isopropyl-3,4-dihydroisoquinolin-2(1H)-yl)sulfonyl]ethyl}-N-hydroxyformamide (18)

Step a) Formation of N-[(4-isopropylphenyl)methylene]-2,2-dimethoxyethanamine

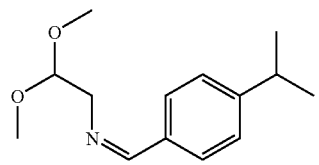

A mixture of 4-isopropyl benzaldehyde (25 g, 183 mmol) and aminoacetaldehyde dimethylacetal (28.9 g, 275 mmol) in toluene (250 ml) was refluxed with azeotropic removal of water for 13 hours. The solvent was removed under vacuum to afford the titled compound as viscous oil (36 g, 83%). TLC-Chloroform/methanol: (95/5): R$_f$=0.75. $^1$H-NMR (CDCl$_3$, 400 MHz) δ 1.28 (6H, d), 2.95 (1H, m), 3.44 (6H, s), 3.78 (2H, d), 4.68 (1H, t), 7.28 (2H, d), 7.68 (2H, d), 8.27 (1H, s).

Step b) Formation of 6-isopropylisoquinoline

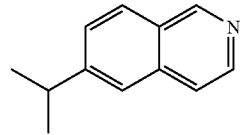

N-[(4-isopropylphenyl)methylene]-2,2-dimethoxyethanamine (5.0 g) was added to hot concentrated sulfuric acid (50 ml) at 140° C. dropwise over a period of 10 min. The mixture was stirred at this temperature for additional 10 min and cooled to RT. The mixture was basified with an aqueous solution of NaOH and the product was extracted with MTBE (6×75 ml). The combined organic layers were dried (MgSO$_4$) and evaporated under reduced pressure. The residue was purified by flash chromatography on silica (pet. ether/EtOAc 9/1) to afford the titled compound as a solid (200 mg, 15%). TLC—Chloroform/methanol: (9.5/0.5): R$_f$=0.55. $^1$H NMR (CDCl$_3$, 400 MHz) δ 1.28 (6H, d), 3.10 (1H, m), 7.49 (1H, d), 7.53 (2H, m), 7.89 (1H, d), 8.49 (1H, d), 9.19 (1H, s).

Step c) Formation of 6-isopropyl-1,2,3,4-tetrahydroisoquinoline hydrochloride

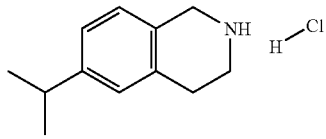

A mixture of 6-isopropylisoquinoline (1.8 g) and platinum (IV) oxide (450 mg) in acetic acid (60 ml) was hydrogenated under a pressure of 5 Kg of hydrogen for 3 days. The catalyst was filtered and the filtrate was evaporated under reduced pressure. The residue was suspended in a solution of HCl (4M in dioxane, 50 ml) and evaporated under reduced pressure to afford the titled compound as a solid (2.0 g, 95%). This step was repeated twice to ensure the complete exchange of acetate salt with HCl. TLC—Chloroform/methanol: (9/1): $R_f$=0.15. MP: 193.4-196° C. $^1$H-NMR (DMSO-$d_6$, 400 MHz) δ 1.18 (6H, d), 2.86 (1H, m), 2.97 (2H, m), 3.37 (2H, m), 4.19 (2H, s), 7.08 (1H, s), 7.12 (2H, m), 9.31 (2H, br. s).

Step d) Formation of 6-isopropyl-2-(methylsulfonyl)-1,2,3,4-tetrahydroisoquinoline

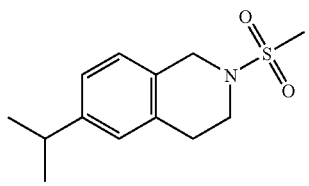

The title compound was prepared following procedure described in Example 1 step a), but starting from 6-isopropyl-1,2,3,4-tetrahydroisoquinoline hydrochloride and one additional equivalent of DIEA. The title compound was obtained as a white powder (1.75 g, 73%). HPLC, Rt: 4.3 min (purity: 84%). LC/MS, M$^+$(ESI): 254.1.

Step e) Formation of N-{1-[(4S)-2,2-dimethyl-1,3-dioxolan-4-yl]-2-[(6-isopropyl-3,4-dihydroisoquinolin-2(1H)-yl)sulfonyl]ethyl}-N-hydroxyformamide

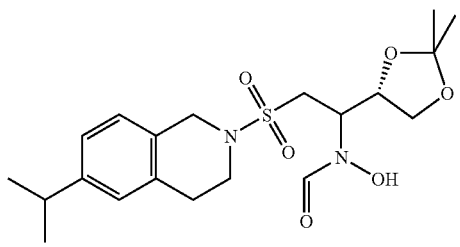

The title compound was prepared following procedure described in Example 1 step b), but starting from 6-isopropyl-2-(methylsulfonyl)-1,2,3,4-tetrahydroisoquinoline and 2,3-O-isopropylidene-D-glyceraldehyde. After purification by crystallization in EtOAc, the title compound (18) was obtained as a white powder (260 mg, 41%). HPLC, Rt: 3.6 min (purity: 98.4%). LC/MS, M$^+$(ESI): 427.4, M$^-$(ESI): 425.4.

Example 19

Formation of N-{2-[(7-chloro-3,4-dihydroisoquinolin-2(1H)-yl)sulfonyl]-1-[(4S)-2,2-dimethyl-1,3-dioxolan-4-yl]ethyl}-N-hydroxyformamide (19)

Step a) Formation of N-[2-(4-chlorophenyl)ethyl]methanesulfonamide

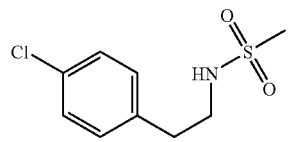

A solution of 4-chlorophenethylamine (5.0 g, 32 mmol) and DIEA (6.0 ml, 35 mmol) in anhydrous DCM (100 ml) was cooled at −5° C. and methanesulfonyl chloride (2.75 ml, 35 mmol) was added dropwise. The resulting mixture was stirred at −5° C. for 1 hour. Then the reaction mixture was washed with a 1N aqueous solution of HCl (2×100 ml) and a saturated aqueous solution of NaHCO$_3$ (100 ml). The aqueous layers were extracted with DCM (100 ml). The organic layers were combined, dried (MgSO$_4$) and the solvent was removed under reduced pressure to give 7.4 g (98%) of the title compound as a pale yellow powder. HPLC, Rt: 2.6 min (purity: 95.1%). LC/MS, M$^+$(ESI): 234.1, M$^-$(ESI): 232.1.

Step b) Formation of 7-chloro-2-(methylsulfonyl)-1,2,3,4-tetrahydroisoquinoline

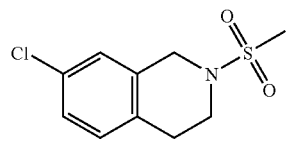

A solution N-[2-(4-chlorophenyl)ethyl]methanesulfonamide (6.9 g, 29.5 mmol) and trioxane (2.65 g, 29.5 mmol) was prepared in anhydrous DCM (150 ml), then boron trifluoride diethyl ether complex (12.7 ml, 102.73 mmol) was added dropwise. The resulting mixture was stirred at room temperature for 20 minutes, then washed with water (150 ml) and a saturated aqueous solution of NaHCO$_3$ (150 ml). The aqueous layers were extracted with DCM (100 ml). The organic layers were combined, dried (MgSO$_4$) and the solvent was removed under reduced pressure to give a pale yellow solid. The solid was taken up with DCM (10 ml, partially soluble), then Et$_2$O (50 ml) and pentane (50 ml) were added. The resulting precipitate was filtered, washed with Et$_2$O/pentane (1/1) and pentane, then dried under reduced pressure to give 6.0 g (83%) of the title compound as a white powder. HPLC, Rt: 3.1 min (purity: 100%). LC/MS, M$^+$(ESI): 246.1.

Step c) Formation of N-{2-[(7-chloro-3,4-dihydroisoquinolin-2(1H)-yl)sulfonyl]-1-[(4S)-2,2-dimethyl-1,3-dioxolan-4-yl]ethyl}-N-hydroxyformamide

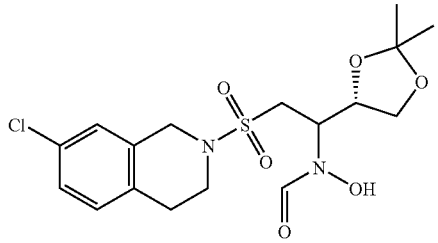

A solution of 7-chloro-2-(methylsulfonyl)-1,2,3,4-tetrahydroisoquinoline (200 mg, 0.81 mmol) was prepared in anhydrous THF (6 ml) and cooled at −78° C. Diethyl chlorophosphate (0.13 ml, 0.90 mmol) was added dropwise, followed by a solution of LiHMDS (1M in THF, 1.8 ml, 1.8 mmol). After 10 min. at −78° C., a solution of 2,3-O-isopropylidene-D-glyceraldehyde (130 mg, 1.0 mmol) in anhydrous THF (1 ml) was added. The reaction mixture was stirred at −78° C. for 15 min, then at room temperature for 90 min. Then a 50% aqueous solution of NH$_2$OH (2.1 ml) was added and the resulting biphasic mixture was heated at 60° C. for 15 hours. The reaction mixture was washed with brine (5 ml) and the layers were separated. The organic layer was dried (MgSO$_4$) and the solvent was removed under reduced pressure to give a yellow oily residue. A mixture of formic acid (2.4 ml) and acetic anhydride (0.6 ml) was stirred at 0° C. for 30 min., then a solution of the previous oil in anhydrous THF (5 ml) was added and the resulting mixture was stirred at 0° C. for 5 min., then at RT for 90 min. The mixture was evaporated under reduced pressure. The residue was taken up with MeOH (10 ml) and heated at 60° C. for 90 min. The mixture was evaporated under reduced pressure to give a yellow oily residue, which was taken up in EtOAc (15 ml) and washed with a saturated aqueous solution of NaHCO$_3$ (5 ml). The organic layer was dried (Na$_2$SO$_4$) and the solvent was removed under reduced pressure to give the crude compound. Purification by crystallization from EtOAc/pentane gave 56 mg (16%) of the title compound (19) as a white powder. HPLC, Rt: 3.1 min (purity: 99.7%). LC/MS, M$^+$(ESI): 419.3, M$^-$(ESI): 417.3.

Example 20

Formation of N-(1-{[(6,7-dimethoxy-3,4-dihydroisoquinolin-2(1H)-yl)sulfonyl]methyl}-2,2-dimethylpropyl)-N-hydroxyformamide (20)

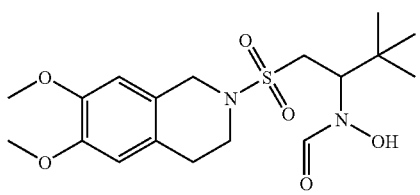

The title compound was prepared following procedure described in Example 1 step b), but starting from 6,7-dimethoxy-2-(methylsulfonyl)-1,2,3,4-tetrahydroisoquinoline and trimethylacetaldehyde. After purification by crystallization in EtOAc/pentane, the title compound (20) was obtained as a white powder (175 mg, 24%). HPLC, Rt: 2.7 min (purity: 99.0%). LC/MS, M$^+$(ESI): 401.4, M$^-$(ESI): 399.4.

Example 21

Formation of N-{2-[(7-chloro-3,4-dihydroisoquinolin-2(1H)-yl)sulfonyl]-1-cyclopentylethyl}-N-hydroxyformamide (21)

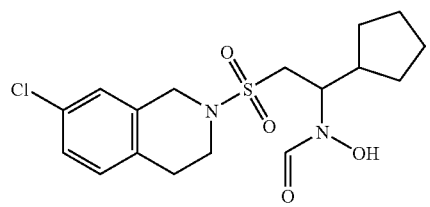

The title compound was prepared following procedure described in Example 19 step c), but starting from 7-chloro-2-(methylsulfonyl)-1,2,3,4-tetrahydroisoquinoline and cyclopentanecarboxaldehyde. After purification by crystallization in EtOAc/pentane, the title compound (21) was obtained as a white powder (270 mg, 34%). HPLC, Rt: 3.6 min (purity: 93.6%). LC/MS, M$^+$(ESI): 387.3, M$^-$(ESI): 385.3.

Example 22

Formation of N-{(1R)-2-[(7-chloro-3,4-dihydroisoquinolin-2(1H)-yl)sulfonyl]-1-[(2R)-tetrahydrofuran-2-yl]ethyl}-N-hydroxyformamide (22)

Step a) Formation of 2-[(7-chloro-3,4-dihydroisoquinolin-2(1H)-yl)sulfonyl]-1-[(2R)-tetrahydrofuran-2-yl]ethanone

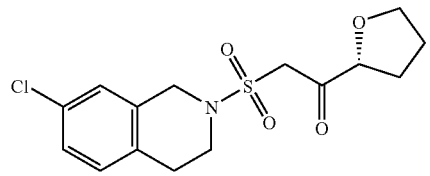

A solution of 7-chloro-2-(methylsulfonyl)-1,2,3,4-tetrahydroisoquinoline (540 mg, 2.2 mmol) was prepared in anhydrous THF (6 ml) and cooled at −78° C. Then a solution of LiHMDS (1M in THF, 4.8 ml, 4.8 mmol) was added dropwise. After 25 min., a 1M solution of methyl (2R)-tetrahydrofuran-2-carboxylate (300 mg, 2.3 mmol) in anhydrous THF was added. The resulting mixture was stirred at −78° C. for 4 hours, then at RT for 15 hours. The reaction mixture was poured in a 1N aqueous solution of HCl (5 ml) and extracted with Et$_2$O (3×10 ml). The organic layers were combined, washed with water (10 ml) and brine (10 ml), then dried (MgSO$_4$) and the solvents were removed under reduced pressure to give a pale yellow solid. The solid was washed with a minimum amount of MeOH to give the title compound as a white powder (520 mg, 69%). HPLC, Rt: 3.4 min (purity: 97.0%). LC/MS, M$^+$(ESI): 344.2, M$^-$(ESI): 342.2.

Step b) Formation of 2-[(7-chloro-3,4-dihydroisoquinolin-2(1H)-yl)sulfonyl]-1-[(2R)-tetrahydrofuran-2-yl]ethanol

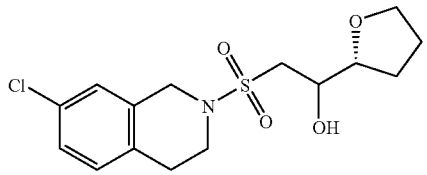

A solution of 2-[(7-chloro-3,4-dihydroisoquinolin-2(1H)-yl)sulfonyl]-1-[(2R)-tetrahydrofuran-2-yl]ethanone (520 mg, 1.51 mmol) was prepared in a mixture of THF/MeOH (ratio 1/5, 10 ml), then NaBH$_4$ (86 mg, 2.27 mmol) was added portionwise. The resulting mixture was stirred at RT for 1 hour. The reaction mixture was concentrated under reduced pressure, then diluted with EtOAc (50 ml) and washed with a 1N aqueous solution of HCl (4 ml). The aqueous layer was extracted with EtOAc (3×). The organic layers were combined, washed with water and brine, dried (MgSO$_4$) and the solvent was removed under reduced pressure to give the title compound as a white powder (420 mg, 80%) used in the next step without further purification. HPLC, Rt: 3.1 min (purity: 97.9%). LC/MS, M$^+$(ESI): 346.2.

Step c) Formation 7-chloro-2-({2-[(2R)-tetrahydrofuran-2-yl]vinyl}sulfonyl)-1,2,3,4-tetrahydroisoquinoline

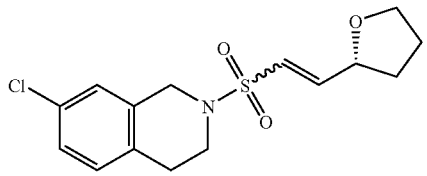

A solution of 2-[(7-chloro-3,4-dihydroisoquinolin-2(1H)-yl)sulfonyl]-1-[(2R)-tetrahydrofuran-2-yl]ethanol (420 mg, 1.21 mmol) and Et$_3$N (370 mg, 3.63 mmol) in anhydrous DCM (5 ml) was cooled at 0° C., then methanesulfonyl chloride (0.14 ml, 1.82 mmol) was added dropwise. The resulting mixture was stirred at 0° C. for 5 min., then at RT for 15 hours. The reaction mixture was poured into a 1N aqueous solution of HCl and extracted with EtOAc (2×). The organic layers were combined, dried (MgSO$_4$) and the solvents were removed under reduced pressure to give the title compound as an orange solid (400 mg, quantitative). HPLC, Rt: 3.7 min (purity: 94.2%). LC/MS, M$^+$(ESI): 328.2.

Step d) Formation of (1R)-2-[(7-chloro-3,4-dihydroisoquinolin-2(1H)-yl)sulfonyl]-N-hydroxy-1-[(2R)-tetrahydrofuran-2-yl]ethanamine and (1S)-2-[(7-chloro-3,4-dihydroisoquinolin-2(1H)-yl)sulfonyl]-N-hydroxy-1-[(2R)-tetrahydrofuran-2-yl]ethanamine (1R,2R)

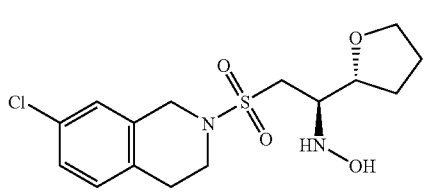

and

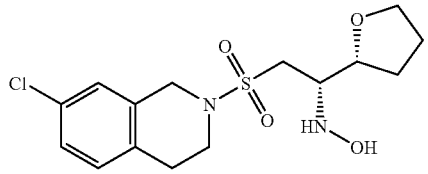

(1S,2R)

A solution of 7-chloro-2-({2-[(2R)-tetrahydrofuran-2-yl]vinyl}sulfonyl)-1,2,3,4-tetrahydroisoquinoline (400 mg, 1.22 mmol) was prepared in THF (6 ml) and a 50% aqueous solution of NH$_2$OH (1.1 ml, 18.3 mmol)) was added. The resulting biphasic mixture was heated at 60° C. for 6 hours. The solvent was evaporated and the residue was extracted with EtOAc. The organic layer was dried (MgSO$_4$) and the solvent was removed under reduced pressure to give a yellow oil. Purification by flash chromatography on silica (cHex/EtOAc 35/65) allowed the separation of both diastereoisomers (1R,2R) and (1S,2R).

The expected (1S,2R) isomer was obtained as the major product (150 mg, 34%). HPLC, Rt: 2.4 min (purity: 90.4%). LC/MS, M$^+$(ESI): 361.3.

The expected (1R,2R) isomer was obtained as the minor product (80 mg, 18%). HPLC, Rt: 2.6 min (purity: 72%). LC/MS, M$^+$(ESI): 361.2.

Step e) Formation of N-{(1R)-2-[(7-chloro-3,4-dihydroisoquinolin-2(1H)-yl)sulfonyl]-1-[(2R)-tetrahydrofuran-2-yl]ethyl}-N-hydroxyformamide

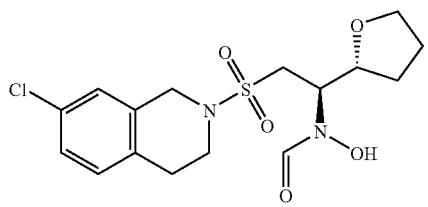

A mixture of formic acid (0.5 ml) and acetic anhydride (0.125 ml) was stirred at 0° C. for 1 hour, then a solution of (1R)-2-[(7-chloro-3,4-dihydroisoquinolin-2(1H)-yl)sulfonyl]-N-hydroxy-1-[(2R)-tetrahydrofuran-2-yl]ethanamine (80 mg, 0.22 mmol) in anhydrous THF (5 ml) was added and the resulting mixture was stirred at RT for 1 hour. The mixture was evaporated under reduced pressure. The residue was taken up with MeOH (5 ml) and heated at 55° C. for 1 hour. The reaction mixture was evaporated under reduced pressure. After purification by crystallization in EtOAc/pentane, the title compound (22) was obtained as a white powder (37 mg, 43%). HPLC, Rt: 3.0 min (purity: 94.1%). LC/MS, M$^+$(ESI): 389.3, M$^-$(ESI): 387.3.

Example 23

Formation of N-{(1S)-2-[(7-chloro-3,4-dihydroiso-quinolin-2(1H)-yl)sulfonyl]-1-[(2R)-tetrahydrofuran-2-yl]ethyl}-N-hydroxyformamide (23)

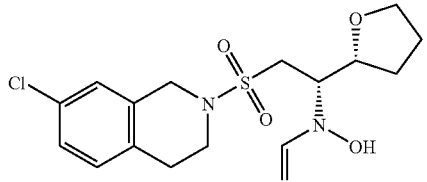

The title compound was prepared following procedure described in Example 22 step e), but starting from (1S)-2-[(7-chloro-3,4-dihydroisoquinolin-2(1H)-yl)sulfonyl]-N-hydroxy-1-[(2R)-tetrahydrofuran-2-yl]ethanamine. After purification by crystallization in EtOAc/pentane, the title compound (23) was obtained as a white powder (99 mg, 61%). HPLC, Rt: 2.9 min (purity: 96.0%). LC/MS, M+(ESI): 389.3, M−(ESI): 387.3.

Example 24

Formation of N-((2S)-1-{[(6,7-dimethoxy-3,4-dihydroisoquinolin-2(1H)-yl)sulfonyl]methyl}-2,3-dihydroxypropyl)-N-hydroxyformamide (24)

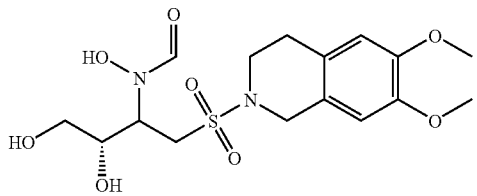

A solution of N-{2-[(6,7-dimethoxy-3,4-dihydroisoquinolin-2(1H)-yl)sulfonyl]-1-[(4S)-2,2-dimethyl-1,3-dioxolan-4-yl]ethyl}-N-hydroxyformamide (100 mg, 0.23 mg) was prepared in MeOH (1 ml) and water (2 ml), then a 1N aqueous solution of HCl (0.5 ml). The reaction mixture was stirred for 22 hours at RT. The reaction mixture was diluted with a saturated aqueous solution of NaHCO₃ (10 ml) and extracted with EtOAc (3×10 ml). The organic layers were combined, dried (Na₂SO₄) and the solvents were removed under reduced pressure. The residue was taken up with pentane and an off-white solid precipitated out. The solid was filtered, washed with pentane and dried under reduced pressure to give 15 mg (17%) of the title compound (24) as an off-white powder. HPLC, Rt: 1.9 min (purity: 92.9%). LC/MS, M+(ESI): 405.4, M−(ESI): 403.3.

Example 25

Formation of N-(1-cyclopentyl-2-{[6-(trifluoromethyl)-3,4-dihydro-isoquinolin-2(1H)-yl]sulfonyl}ethyl)-N-hydroxyformamide (25)

Step a) Formation of 2-(methylsulfonyl)-6-(trifluoromethyl)-1,2,3,4-tetrahydroisoquinoline

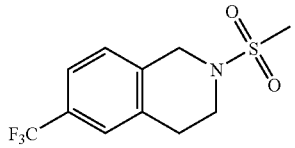

The title compound was prepared following procedure described in Example 1 step a), but starting from 6-trifluoromethyl-1,2,3,4-tetrahydroisoquinoline hydrochloride and one additional equivalent of DIEA. After purification by crystallization in EtOAc/pentane, the title compound was obtained as a beige powder (4.0 g, 78%). HPLC, Rt: 2.15 min (purity: 99.2%). LC/MS, M+(ESI): 280.2.

Step b) Formation of N-(1-cyclopentyl-2-{[6-(trifluoromethyl)-3,4-dihydroisoquinolin-2(1H)-yl]sulfonyl}ethyl)-N-hydroxyformamide

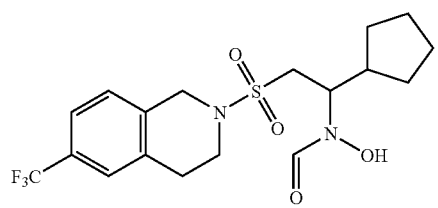

The title compound was prepared following procedure described in Example 1 step b), but starting from 2-(methylsulfonyl)-6-(trifluoromethyl)-1,2,3,4-tetrahydroisoquinoline and cyclopentanecarboxaldehyde. After purification by crystallization in EtOAc/pentane, the title compound (25) was obtained as a white powder (335 mg, 45%). HPLC, Rt: 3.7 min (purity: 99.4%). LC/MS, M+(ESI): 421.4, M−(ESI): 419.3.

Example 26

Formation of N-(1-{[(5-fluoro-1,3-dihydro-2H-isoindol-2-yl)sulfonyl]methyl}-3,3-dimethylbutyl)-N-hydroxyformamide (26)

Step a) Formation of 5-fluoro-2-(methylsulfonyl)isoindoline

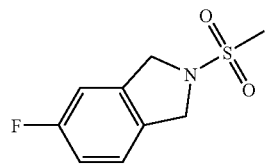

The title compound was prepared following procedure described in Example 1 step a), but starting from 5-fluoro-2,3-dihydro-1H-isoindole hydrochloride and one additional equivalent of DIEA. After purification by crystallization in DCM/Et₂O, the title compound was obtained as a grey powder (530 mg, 43%). HPLC, Rt: 2.2 min (purity: 100%). LC/MS, M+(ESI): 216.1.

Step b) Formation of N-(1-{[(5-fluoro-1,3-dihydro-2H-isoindol-2-yl)sulfonyl]methyl}-3,3-dimethylbutyl)-N-hydroxyformamide

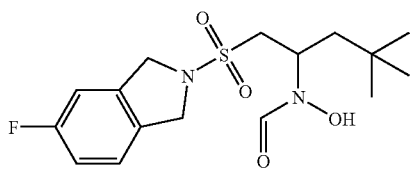

The title compound was prepared following procedure described in Example 19 step c), but starting from 5-fluoro-2-(methylsulfonyl)isoindoline and 3,3-dimethylbutyraldehyde. After purification by crystallization in EtOAc/cHex, the title compound (26) was obtained as a white powder (210 mg, 39%). HPLC, Rt: 3.3 min (purity: 99.1%). LC/MS, M$^+$(ESI): 359.3, M$^-$(ESI): 357.3.

Example 27

Formation of N-hydroxy-N-((1S)-1-[(2R)-tetrahydrofuran-2-yl]-2-{[7-(trifluoromethyl)-3,4-dihydroisoquinolin-2(1H)-yl]sulfonyl}ethyl)formamide (27)

Step a) Formation of 2-(methylsulfonyl)-7-(trifluoromethyl)-1,2,3,4-tetrahydroisoquinoline

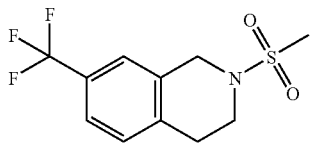

The title compound was prepared following procedure described in Example 1 step a), but starting from 7-trifluoromethyl-1,2,3,4-tetrahydroisoquinoline hydrochloride and one additional equivalent of DIEA. After purification by crystallization in Et$_2$O/pentane, the title compound was obtained as a white powder (2.0 g, 80%). HPLC, Rt: 4.0 min (purity: 100%).

Step b) Formation of 1-[(2R)-tetrahydrofuran-2-yl]-2-{[7-(trifluoromethyl)-3,4-dihydroisoquinolin-2(1H)-yl]sulfonyl}ethanone

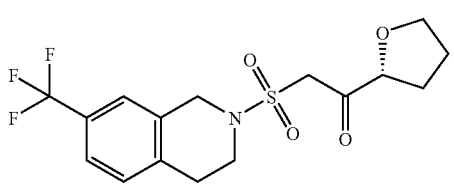

The title compound was prepared following procedure described in Example 22 step a), but starting from 2-(methylsulfonyl)-7-(trifluoromethyl)-1,2,3,4-tetrahydroisoquinoline. After purification by crystallization in Et$_2$O, the title compound was obtained as an off-white powder (290 mg, 54%). HPLC, Rt: 3.7 min (purity: 88.5%). LC/MS, M$^+$(ESI): 378.3, M$^-$(ESI): 376.3.

Step c) Formation of 1-[(2R)-tetrahydrofuran-2-yl]-2-{[7-(trifluoromethyl)-3,4-dihydro-isoquinolin-2(1H)-yl]sulfonyl}ethanol

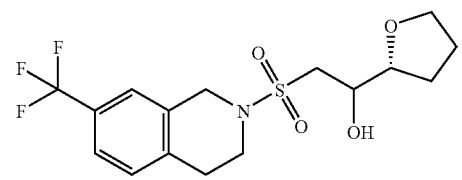

The title compound was prepared following procedure described in Example 22 step b), but starting from 1-[(2R)-tetrahydrofuran-2-yl]-2-{[7-(trifluoromethyl)-3,4-dihydroisoquinolin-2(1H)-yl]sulfonyl}ethanone. The crude title compound was obtained as a pale yellow oil (288 mg, 99%) used without further purification in the next step. HPLC, Rt: 3.3 min (purity: 90.4%). LC/MS, M$^+$(ESI): 380.7.

Step d) Formation of a mixture 2-({2-[(2R)-tetrahydrofuran-2-yl]vinyl}sulfonyl)-7-(trifluoromethyl)-1,2,3,4-tetrahydroisoquinoline

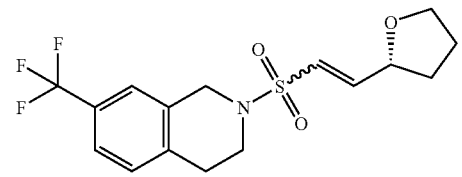

The title compound was prepared following procedure described in Example 22 step c), but starting from 1-[(2R)-tetrahydrofuran-2-yl]-2-{[7-(trifluoromethyl)-3,4-dihydroisoquinolin-2(1H)-yl]sulfonyl}ethanol. The crude title compound was obtained as a brown oil (190 mg, 69%) used without further purification in the next step. HPLC, Rt: 3.9 min (purity: 84.3%). LC/MS, M$^+$(ESI): 362.3.

Step e) Formation of (1R)—N-hydroxy-1-[(2R)-tetrahydrofuran-2-yl]-2-{[7-(trifluoro-methyl)-3,4-dihydroisoquinolin-2(1H)-yl]sulfonyl}ethanamine and (1S)—N-hydroxy-1-[(2R)-tetrahydrofuran-2-yl]-2-{[7-(trifluoromethyl)-3,4-dihydroisoquinolin-2(1H)-yl]sulfonyl}ethanamine

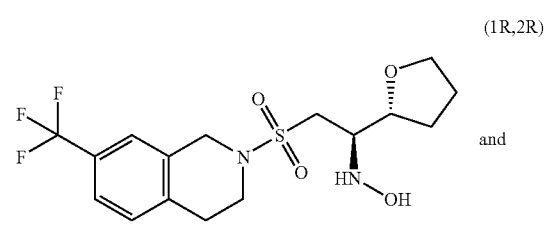

(1R,2R)

and

-continued

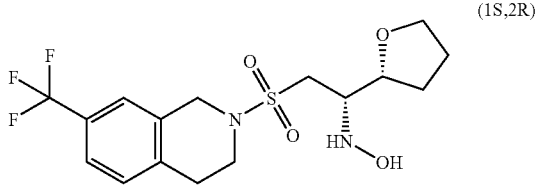
(1S,2R)

The title compound was prepared following procedure described in Example 22 step d), but starting from 2-({2-[(2R)-tetrahydrofuran-2-yl]vinyl}sulfonyl)-7-(trifluoromethyl)-1,2,3,4-tetrahydroisoquinoline. Purification by flash chromatography on silica (cHex/EtOAc 35/65) allowed the separation of both diastereoisomers (1R,2R) and (1S,2R).

The expected (1S,2R) isomer was obtained as the major product (150 mg, 53%). HPLC (254 nm), Rt: 2.7 min (purity: 83%). LC/MS, M+(ESI): 395.4.

The expected (1R,2R) isomer was obtained as the minor product (55 mg, 19%). HPLC (254 nm), Rt: 3.3 min (purity: 51%). LC/MS, M+(ESI): 395.4, M−(ESI): 393.4.

Step f) Formation of N-hydroxy-N-((1S)-1-[(2R)-tetrahydrofuran-2-yl]-2-{[7-(trifluoro-methyl)-3,4-dihydroisoquinolin-2(1H)-yl]sulfonyl}ethyl)formamide

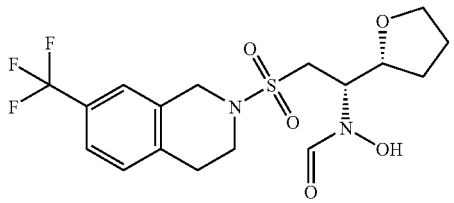

The title compound was prepared following procedure described in Example 22 step e), but starting from (1S)—N-hydroxy-1-[(2R)-tetrahydrofuran-2-yl]-2-{[7-(trifluoromethyl)-3,4-dihydroisoquinolin-2(1H)-yl]sulfonyl}ethanamine. After purification by crystallization in EtOAc/pentane, the title compound (27) was obtained as a white powder (73 mg, 45%). HPLC, Rt: 3.1 min (purity: 99.3%). LC/MS, M+(ESI): 423.3, M−(ESI): 421.3.

Example 28

Formation of N-(1-[(4S)-2,2-dimethyl-1,3-dioxolan-4-yl]-2-{[7-(trifluoro-methyl)-3,4-dihydroisoquinolin-2(1H)-yl]sulfonyl}ethyl)-N-hydroxyformamide (28)

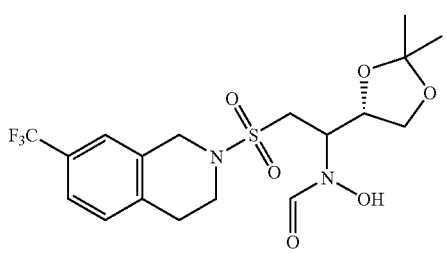

The title compound was prepared following procedure described in Example 19 step c), but starting from 2-(methylsulfonyl)-7-(trifluoromethyl)-1,2,3,4-tetrahydroisoquinoline and 2,3-O-isopropylidene-D-glyceraldehyde. After purification by crystallization in EtOAc/cHex, the title compound (28) was obtained as a white powder (72 mg, 11%). HPLC, Rt: 3.9 min (purity: 90.3%). LC/MS, M+(ESI): 453.3, M−(ESI): 451.3.

Example 29

Formation of N-{(1S)-2-[(5-fluoro-1,3-dihydro-2H-isoindol-2-yl)-sulfonyl]-1-[(2R)-tetrahydrofuran-2-yl]ethyl}-N-hydroxyformamide (29)

Step a) Formation of 2-[(5-fluoro-1,3-dihydro-2H-isoindol-2-yl)sulfonyl]-1-[(2R)-tetrahydrofuran-2-yl]ethanone

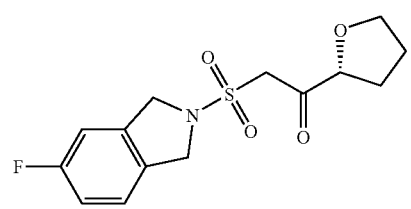

The title compound was prepared following procedure described in Example 22 step a), but starting from 5-fluoro-2-(methylsulfonyl)isoindoline. After purification by crystallization in Et₂O, the title compound was obtained as a grey powder (89 mg, 38%). HPLC, Rt: 2.8 min (purity: 97.4%). LC/MS, M+(ESI): 314.2, M−(ESI): 312.2.

Step b) Formation of 2-[(5-fluoro-1,3-dihydro-2H-isoindol-2-yl)sulfonyl]-1-[(2R)-tetrahydrofuran-2-yl]ethanol

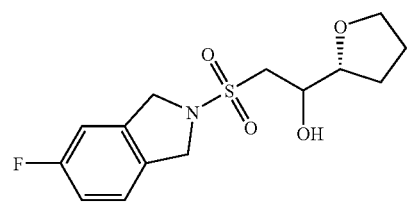

The title compound was prepared following procedure described in Example 22 step b), but starting from 2-[(5-fluoro-1,3-dihydro-2H-isoindol-2-yl)sulfonyl]-1-[(2R)-tetrahydrofuran-2-yl]ethanone. The crude title compound was obtained as a grey solid (78 mg, 86%) used without further purification in the next step. HPLC, Rt: 2.5 min (purity: 92.3%). LC/MS, M+(ESI): 316.2.

Step c) Formation of a mixture 5-fluoro-2-({2-[(2R)-tetrahydrofuran-2-yl]vinyl}sulfonyl)-isoindoline

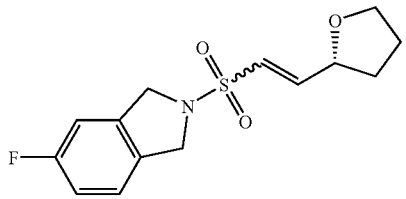

The title compound was prepared following procedure described in Example 22 step c), but starting from 2-[(5-fluoro-1,3-dihydro-2H-isoindol-2-yl)sulfonyl]-1-[(2R)-tetrahydrofuran-2-yl]ethanol. The crude title compound was obtained as a brown oil (69 mg, 94%) used without further purification in the next step. HPLC, Rt: 3.2 min (purity: 76.8%). LC/MS, M$^+$(ESI): 298.2.

Step d) Formation of (1R)-2-[(5-fluoro-1,3-dihydro-2H-isoindol-2-yl)sulfonyl]-N-hydroxy-1-[(2R)-tetrahydrofuran-2-yl]ethanamine and (1S)-2-[(5-fluoro-1,3-dihydro-2H-isoindol-2-yl)sulfonyl]-N-hydroxy-1-[(2R)-tetrahydrofuran-2-yl]ethanamine

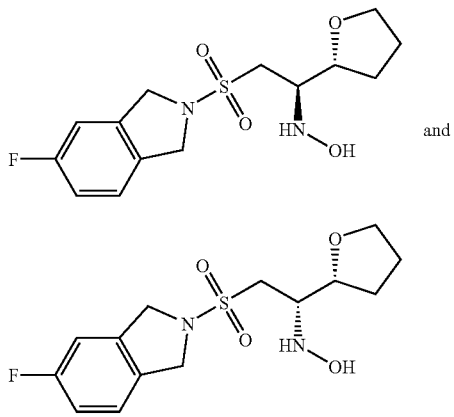

The title compounds were prepared following procedure described in Example 22 step d), but starting from 5-fluoro-2-({2-[(2R)-tetrahydrofuran-2-yl]vinyl}sulfonyl)isoindoline. Purification by flash chromatography on silica (cHex/EtOAc 35/65) allowed the separation of both diastereoisomers (1R,2R) and (1S,2R).

The expected (1S,2R) isomer was obtained as the major product (28 mg, 39%). HPLC, Rt: 1.9 min (purity: 74%). LC/MS, M$^+$(ESI): 331.2.

The expected (1R,2R) isomer was obtained as the minor product (21 mg, 29%). HPLC, Rt: 2.0 min (purity: 69%).

Step e) Formation of N-{(1S)-2-[(5-fluoro-1,3-dihydro-2H-isoindol-2-yl)sulfonyl]-1-[(2R)-tetrahydrofuran-2-yl]ethyl}-N-hydroxyformamide

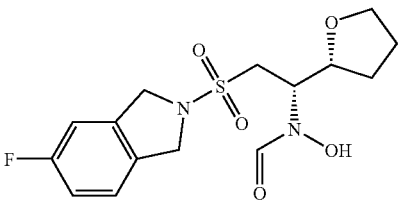

The title compound was prepared following procedure described in Example 22 step e), but starting from (1S)-2-[(5-fluoro-1,3-dihydro-2H-isoindol-2-yl)sulfonyl]-N-hydroxy-1-[(2R)-tetrahydrofuran-2-yl]ethanamine. After purification by crystallization in EtOAc/pentane, the title compound (29) was obtained as a beige powder (12 mg, 40%). HPLC, Rt: 2.3 min (purity: 90.6%). LC/MS, M$^+$(ESI): 359.2, M$^-$(ESI): 357.2.

Example 30

Formation of N-[2,2-dimethyl-1-({[6-(trifluoromethyl)-3,4-dihydro-isoquinolin-2(1H)-yl]sulfonyl}methyl)hept-4-yn-1-yl]-N-hydroxyformamide (30)

Step a) Formation of ethyl 2,2-dimethylhept-4-ynoate

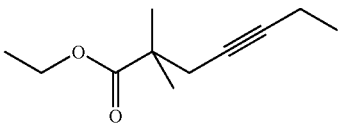

To a solution of LDA (146 ml, 291 mmol, 2M in THF) at −78° C. under nitrogen was added a solution of ethyl isobutyrate (33.9 g, 291 mmol) in dry THF (100 ml) and the mixture was stirred at −78° C. for 2 hours. To the mixture was added 2-pentynyl chloride (25 g, 243 mmol) slowly over a period of 20 min. The reaction mixture was slowly warmed to RT over a period of 12 hours. Water (200 ml) was added and the product was extracted with Et$_2$O (2×200 ml). The combined organic layers were washed with water, brine and dried (MgSO$_4$). The solvent was removed under vacuum and the residue was purified by flash chromatography on silica (pet. ether/EtOAc 9/1) to afford the titled compound as a colorless liquid (29 g, 66%). TLC: Pet ether/EtOAc (8/2): R$_f$=0.75. $^1$H-NMR (CDCl$_3$:300 MHz) δ 1.11 (3H, t), 1.24 (6H, s), 2.15 (2H, m), 2.38 (2H, s), 4.14 (2H, m).

Step b) Formation of 2,2-Dimethylhept-4-yn-1-ol

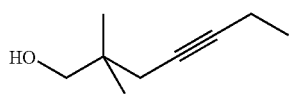

To a slurry of LiAlH$_4$ (7.4 g, 194 mmol) in anhydrous Et$_2$O (200 ml) at 0° C. was added a solution of ethyl 2,2-dimethylhept-4-ynoate (29 g, 159 mmol) in anhydrous Et$_2$O (100 ml) slowly over a period of 30 min. The reaction mixture was stirred at 0° C. for 3 hours. A 10% aqueous solution of NaOH (35 ml) was added slowly. The solid was filtered off. The filtrate was washed with brine, dried (MgSO$_4$) and the solvent was removed under reduced pressure to afford the titled compound as a colorless liquid (20 g, 89%). TLC: Pet. ether/EtOAc (8/2): R$_f$=0.3. $^1$H NMR (CDCl$_3$, 300 MHz) δ 0.95 (6H, s), 1.03 (3H, t), 1.81 (1H, br. s), 2.10 (2H, s), 2.17 (2H, m), 3.14 (2H, s).

Step c) Formation of 2,2-dimethylhept-4-ynal

To a solution of oxalyl chloride (27 g, 214 mmol) in anhydrous DCM (300 ml) at −78° C. under nitrogen was added anhydrous DMSO (33.4 g, 428 mmol) and the mixture was stirred at −78° C. for 20 min. A solution of 2,2-dimethylhept-4-yn-1-ol (20 g, 142 mmol) in anydrous DCM (50 ml) was added slowly over a period of 25 min. The reaction mixture was stirred at −78° C. for 2 hours and quenched by the addition of TEA (165 ml, 1.14 mol) and diluted with water (700 ml). The organic layer was separated and washed with a 1.5M aqueous solution of HCl (200 ml), water and brine. The organic layer was dried (MgSO4) and the solvent was removed under reduced pressure to afford the titled compound as a pale brown liquid (16.5 g, 87%). TLC: Pet. ether/EtOAc (8/2): R$_f$=0.75.

$^1$H-NMR (CDCl$_3$, 400 MHz) δ 1.11 (9H, m), 2.15 (2H, m), 2.31 (2H, s), 9.54 (1H, s).

Step d) Formation of N-[2,2-dimethyl-1-({[6-(trifluoromethyl)-3,4-dihydroisoquinolin-2(1H)-yl]sulfonyl}methyl)hept-4-yn-1-yl]-N-hydroxyformamide

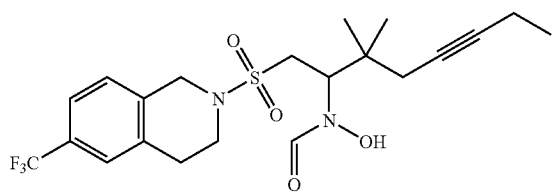

The title compound was prepared following procedure described in Example 19 step c), but starting from 2-(methylsulfonyl)-6-(trifluoromethyl)-1,2,3,4-tetrahydroisoquinoline and 2,2-dimethyl-hept-4-ynal. After purification by crystallization in EtOAc, the title compound (30) was obtained as a beige powder (700 mg, 38%). HPLC, Rt: 4.8 min (purity: 99.5%). LC/MS, M$^+$(ESI): 461.4, M$^-$(ESI): 459.8.

Example 31

Formation of N-[2,2-dimethyl-3-phenyl-1-({[6-(trifluoromethyl)-3,4-dihydroisoquinolin-2(1H)-yl]sulfonyl}methyl)propyl]-N-hydroxyformamide (31)

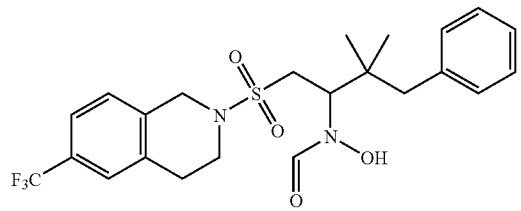

The title compound was prepared following procedure described in Example 19 step c), but starting from 2-(methylsulfonyl)-6-(trifluoromethyl)-1,2,3,4-tetrahydroisoquinoline and 2,2-dimethyl-3-phenylpropanal. After purification by crystallization in EtOAc/pentane, the title compound (31) was obtained as a white powder (400 mg, 39%). HPLC, Rt: 5.0 min (purity: 100%). LC/MS, M$^+$(ESI): 485.3, M$^-$(ESI): 483.4.

Example 32

Formation of N-hydroxy-N-((1R)-1-[(2R)-tetrahydrofuran-2-yl]-2-{[7-(trifluoromethyl)-3,4-dihydroisoquinolin-2(1H)-yl]sulfonyl}ethyl)formamide (32)

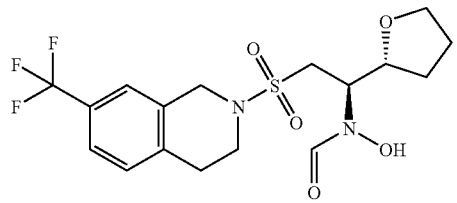

The title compound was prepared following procedure described in Example 22 step e), but starting from (1R)—N-hydroxy-1-[(2R)-tetrahydrofuran-2-yl]-2-{[7-(trifluoromethyl)-3,4-dihydroisoquinolin-2(1H)-yl]sulfonyl}ethanamine. After purification by crystallization in EtOAc/pentane, the title compound (32) was obtained as a white powder (45 mg, 76%). HPLC, Rt: 3.2 min (purity: 77%). LC/MS, M$^+$(ESI): 423.4, M$^-$(ESI): 421.3.

Example 33

Formation of N-hydroxy-N-[1-{[(7-methoxy-3,4-dihydroisoquinolin-2(1H)-yl)sulfonyl]methyl}-3-(tetrahydrofuran-2-yl)propyl]formamide (33)

Step a) Formation of 7-methoxy-2-(methylsulfonyl)-1,2,3,4-tetrahydroisoquinoline

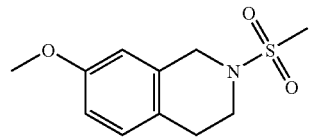

The title compound was prepared following procedure described in Example 1 step a), but starting from 7-methoxy- 1,2,3,4-tetrahydroisoquinoline hydrochloride and one additional equivalent of DIEA. After purification by crystallization in Et$_2$O/pentane, the title compound was obtained as a pale orange powder (0.9 g, 72%). HPLC, Rt: 2.5 min (purity: 100%). LC/MS, M$^+$(ESI): 242.2.

Step b) Formation of N-((2E)-3-(2-furyl)-1-{[(7-methoxy-3,4-dihydroisoquinolin-2(1H)-yl)sulfonyl]methyl}prop-2-en-1-yl)-N-hydroxyformamide

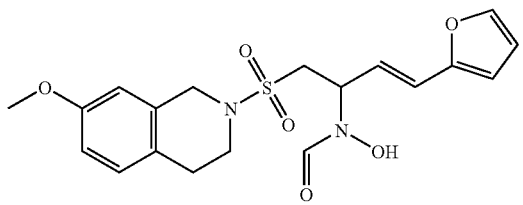

The title compound was prepared following procedure described in Example 19 step c), but starting from 7-methoxy-2-(methylsulfonyl)-1,2,3,4-tetrahydroisoquinoline and 3-(2-furyl)acrolein. After purification by preparative HPLC (Waters Xterra column, gradient water/ACN 95/5 to 0/100), the title compound was obtained as a white powder (33 mg, 6%). HPLC, Rt: 3.3 min (purity: 87.7%). LC/MS, M$^+$(ESI): 407.2, M$^-$(ESI): 405.3.

Step c) Formation of N-hydroxy-N-[1-{[(7-methoxy-3,4-dihydroisoquinolin-2(1H)-yl)sulfonyl]methyl}-3-(tetrahydrofuran-2-yl)propyl]formamide

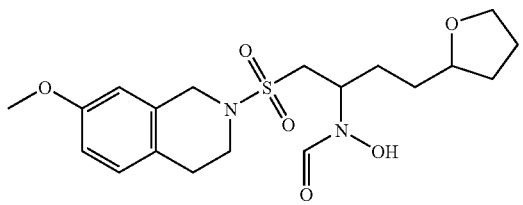

A solution of N-((2E)-3-(2-furyl)-1-{[(7-methoxy-3,4-dihydroisoquinolin-2(1H)-yl)sulfonyl]methyl}prop-2-en-1-yl)-N-hydroxyformamide (30 mg, 0.073 mmol) in MeOH (3 ml) was hydrogenated over 10% Pd/C under 5 bars of hydrogen for 2 hours. The reaction mixture was filtered and the solvent was evaporated under reduced pressure to give the title compound (33) as a colorless oil (10 mg, 33%). HPLC, Rt: 3.2 min (purity: 84.3%). LC/MS, M$^+$(ESI): 413.3, M$^-$(ESI): 411.2.

Example 34

Formation of N-(1-{[(6,7-dichloro-3,4-dihydroisoquinolin-2(1H)-yl)-sulfonyl]methyl}-2-ethylbutyl)-N-hydroxyformamide (34)

Step a) Formation of N-[2-(3,4-dichlorophenyl)ethyl]methanesulfonamide

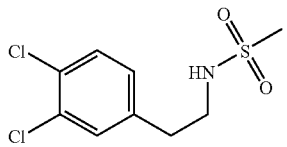

The title compound was prepared following procedure described in Example 19 step a), but starting from 3,4-dichlorophenethylamine. After purification by crystallization in Et$_2$O/pentane, the title compound was obtained as a pale yellow solid (1.41 g, 99%). HPLC, Rt: 3.7 min (purity: 97.5%). LC/MS, M$^+$(ESI): 268.0, M$^-$(ESI): 266.1.

Step b) Formation of 6,7-dichloro-2-(methylsulfonyl)-1,2,3,4-tetrahydroisoquinoline

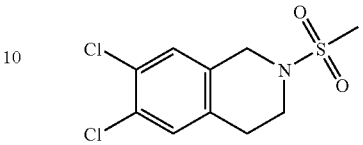

The title compound was prepared following procedure described in Example 19 step b), but starting from N-[2-(3,4-dichlorophenyl)ethyl]methanesulfonamide. A crude mixture was obtained as a mixture of 6,7-dichloro- and 7,8-dichloro-2-(methylsulfonyl)-1,2,3,4-tetrahydroisoquinoline with a ratio of 2.3:1. After purification by crystallization in iPrOH (40 ml/g of crude), the pure title compound was obtained as a white powder (1.93 g, 37%). HPLC, Rt: 3.4 min (purity: 100%). LC/MS, M$^+$(ESI): 280.1.

Step c) Formation of N-(1-{[(6,7-dichloro-3,4-dihydroisoquinolin-2(1H)-yl)sulfonyl]-methyl}-2-ethylbutyl)-N-hydroxyformamide

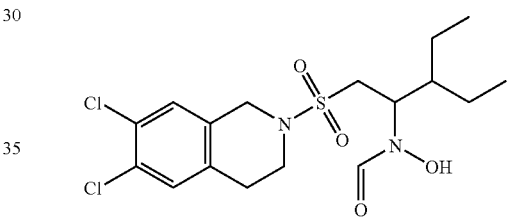

The title compound was prepared following procedure described in Example 19 step c), but starting from 6,7-dichloro-2-(methylsulfonyl)-1,2,3,4-tetrahydroisoquinoline and 2-ethylbutyraldehyde. The addition of hydroxylamine required 48 hrs and the use of 22 equivalents. After purification by crystallization in EtOAc, the title compound (34) was obtained as a white powder (270 mg, 53%). HPLC, Rt: 3.9 min (purity: 100%). LC/MS, M$^+$(ESI): 423.3, M$^-$(ESI): 421.2.

Example 35

Formation of N-(2-ethyl-1-{[(6-isopropyl-3,4-dihydroisoquinolin-2(1H)-yl)sulfonyl]methyl}butyl)-N-hydroxyformamide (35)

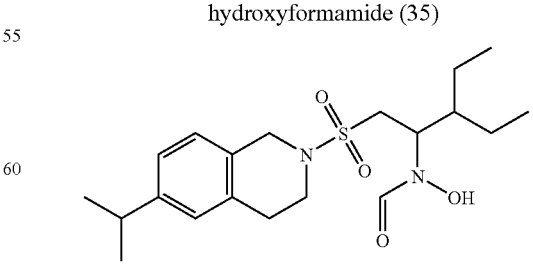

The title compound was prepared following procedure described in Example 19 step c), but starting from 6-isopropyl-2-(methylsulfonyl)-1,2,3,4-tetrahydroisoquinoline and 2-ethylbutyraldehyde. The addition of hydroxylamine required 48 hrs and the use of 22 equivalents. After purification by crystallization in EtOAc/pentane, the title compound (35) was obtained as a white powder (79 mg, 17%). HPLC, Rt: 4.7 min (purity: 95.4%). LC/MS, M$^+$(ESI): 397.4, M$^-$(ESI): 395.3.

Example 36

Formation of N-(1-{[(7-bromo-3,4-dihydroisoquinolin-2(1H)-yl)sulfonyl]-methyl}-2-ethylbutyl)-N-hydroxyformamide (36)

Step a) Formation of 7-bromo-2-(methylsulfonyl)-1,2,3,4-tetrahydroisoquinoline

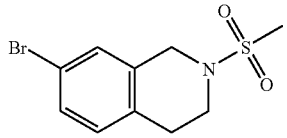

The title compound was prepared following procedure described in Example 1 step a), but starting from 7-bromo-1,2,3,4-tetrahydroisoquinoline hydrochloride and one additional equivalent of DIEA. The title compound was obtained as a pale yellow powder (1.75 g, 75%). HPLC, Rt: 3.1 min (purity: 100%). LC/MS, M$^+$(ESI): 292.1.

Step b) Formation of N-(1-{[(7-bromo-3,4-dihydroisoquinolin-2(1H)-yl)sulfonyl]methyl}-2-ethylbutyl)-N-hydroxyformamide

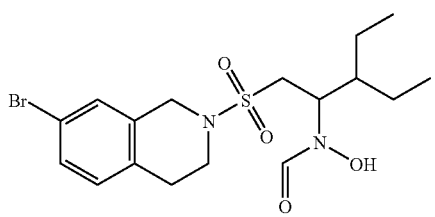

The title compound was prepared following procedure described in Example 19 step c), but starting from 7-bromo-2-(methylsulfonyl)-1,2,3,4-tetrahydroisoquinoline and 2-ethylbutyraldehyde. The addition of hydroxylamine required 48 hrs and the use of 22 equivalents. After purification by crystallization in EtOAc/pentane, the title compound (36) was obtained as a white powder (256 mg, 49%). HPLC, Rt: 4.4 min (purity: 100%). LC/MS, M$^+$(ESI): 435.2, M$^-$(ESI): 433.1.

Example 37

Formation of N-[2-ethyl-1-({[6-(trifluoromethyl)-3,4-dihydroisoquinolin-2(1H)-yl]sulfonyl}methyl)butyl]-N-hydroxyformamide (37)

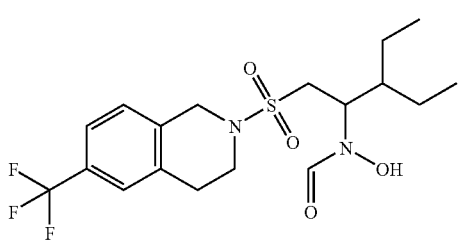

The title compound was prepared following procedure described in Example 19 step c), but starting from 2-(methylsulfonyl)-6-(trifluoromethyl)-1,2,3,4-tetrahydroisoquinoline and 2-ethylbutyraldehyde. The addition of hydroxylamine required 48 hrs and the use of 22 equivalents. After purification by crystallization in EtOAc/pentane, the title compound (37) was obtained as a white powder (233 mg, 46%). HPLC, Rt: 4.5 min (purity: 100%). LC/MS, M$^+$(ESI): 423.4, M$^-$(ESI): 421.3.

Example 38

Formation of N-(2-ethyl-1-{[(7-methoxy-3,4-dihydroisoquinolin-2(1H)-yl)sulfonyl]methyl}butyl)-N-hydroxyformamide (38)

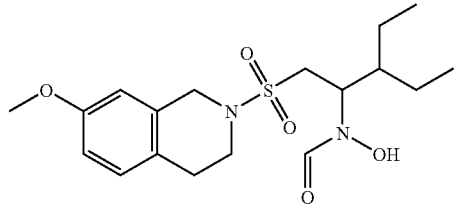

The title compound was prepared following procedure described in Example 19 step c), but starting from 7-methoxy-2-(methylsulfonyl)-1,2,3,4-tetrahydroisoquinoline and 2-ethylbutyraldehyde. The addition of hydroxylamine required 48 hrs and the use of 22 equivalents. After purification by crystallization in EtOAc/pentane, the title compound (38) was obtained as a white powder (84 mg, 18%). HPLC, Rt: 3.9 min (purity: 99.8%). LC/MS, M$^+$(ESI): 385.3, M$^-$(ESI): 383.3.

Example 39

Formation of N-(1-{[(6,7-dichloro-3,4-dihydroisoquinolin-2(1H)-yl)-sulfonyl]methyl}-2-methylpropyl)-N-hydroxyformamide (39)

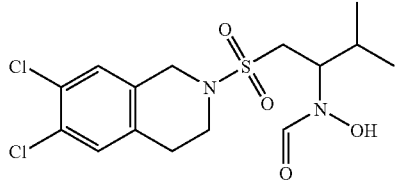

The title compound was prepared following procedure described in Example 19 step c), but starting from 6,7-dichloro-2-(methylsulfonyl)-1,2,3,4-tetrahydroisoquinoline and isobutyraldehyde. After purification by crystallization in EtOAc, the title compound (39) was obtained as a white powder (204 mg, 43%). HPLC, Rt: 4.1 min (purity: 99.2%). LC/MS, M$^+$(ESI): 395.2, M$^-$(ESI): 393.2.

Example 40

Formation of N-(3,3-dimethyl-1-{[(7-propoxy-3,4-dihydroisoquinolin-2(1H)-yl)sulfonyl]methyl}butyl)-N-hydroxyformamide (40)

Step a) Formation of tert-butyl 7-propoxy-3,4-dihydroisoquinoline-2(1H)-carboxylate

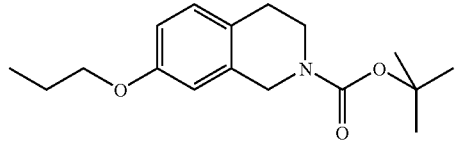

To a mixture of tert-butyl 7-hydroxy-3,4-dihydroisoquinoline-2(1H)-carboxylate (2.2 g, 8 mmol) in anhydrous DMF (20 ml) was added potassium carbonate (2.43 g, 17 mmol) followed by propyl iodide (4.42 g, 26 mmol). The mixture was stirred at 75° C. for 16 hours, then evaporated under reduced pressure. The residue was taken up with EtOAc (50 ml) and washed with water and brine. The organic layer was dried (MgSO$_4$) and the solvent was removed under reduced pressure to afford the titled compound as a solid (2.2 g, 88%) used in the next step without further purification. TLC—Chloroform/methanol (9/1): R$_f$=0.75. $^1$H-NMR (CDCl$_3$, 400 MHz) δ 1.04 (3H, t), 1.50 (9H, s), 1.81 (2H, m), 2.76 (2H, m), 3.62 (2H, m), 3.91 (2H, m), 4.54 (2H, s), 6.65 (1H, s), 6.74 (1H, d), 7.04 (1H, d).

Step b) Formation of 7-propoxy-1,2,3,4-tetrahydroisoquinoline hydrochloride

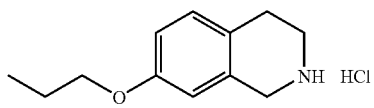

To a solution of HCl (2M in dioxane, 40 ml) was added tert-butyl 7-propoxy-3,4-dihydroisoquinoline-2(1H)-carboxylate (2.2 g). The resulting mixture was stirred at RT for 4 hours. The solvent was removed under reduced pressure to afford the title compound as a solid (1.7 g, 97%). TLC—Chloroform/methanol (9/1): R$_f$=0.15. $^1$H-NMR (DMSO-d$_6$, 400 MHz) δ 0.96 (3H, t), 1.71 (2H, m), 2.90 (2H, m), 3.32 (2H, m), 3.89 (2H, m), 4.17 (2H, s), 6.81 (2H, m), 7.10 (1H, d), 9.63 (2H, br. s).

Step c) Formation of 2-(methylsulfonyl)-7-propoxy-1,2,3,4-tetrahydroisoquinoline

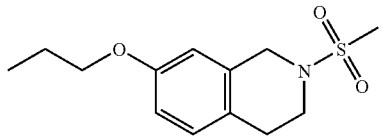

The title compound was prepared following procedure described in Example 1 step a), but starting from 7-propoxy-1,2,3,4-tetrahydroisoquinoline hydrochloride and one additional equivalent of DIEA. After purification by flash chromatography on silica (cHex/EtOAc), the title compound was obtained as a white powder (2.0 g, 95%). HPLC, Rt: 4.0 min (purity: 99.6%). LC/MS, M$^+$(ESI): 270.1.

Step e) Formation of N-(3,3-dimethyl-1-{[(7-propoxy-3,4-dihydroisoquinolin-2(1H)-yl)sulfonyl]methyl}butyl)-N-hydroxyformamide

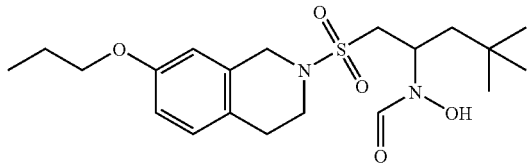

A solution of 2-(methylsulfonyl)-7-propoxy-1,2,3,4-tetrahydroisoquinoline (270 mg, 1.0 mmol) was prepared in anhydrous THF (15 ml) and cooled at 0° C. Diethyl chlorophosphate (0.14 ml, 1.0 mmol) was added dropwise, followed by a solution of LiHMDS (1M in THF, 2.2 ml, 2.2 mmol). After 5 min. at 0° C., 3,3-dimethylbutyraldehyde (140 μl, 1.2 mmol) was added. The reaction mixture was stirred at 0° C. for 1 hour. Then a 50% aqueous solution of NH$_2$OH (0.88 ml, 15 mmol) was added and the resulting biphasic mixture was heated at 60° C. for 15 hours. The reaction mixture was washed with brine (5 ml) and the layers were separated. The organic layer was dried (MgSO$_4$) and the solvent was removed under reduced pressure to give an oil. A mixture of formic acid (2.8 ml) and acetic anhydride (0.7 ml) was stirred at 0° C. for 30 min., then a solution of the previous oil in anhydrous THF (10 ml) was added and the resulting mixture was stirred at 0° C. for 5 min., then at RT for 5 hours. The mixture was evaporated under reduced pressure. The residue was taken up with MeOH (10 ml) and heated at 60° C. for 2 hours. The mixture was evaporated under reduced pressure to give a solid residue. Purification by crystallization from EtOAc/cHex gave 186 mg (45%) of the title compound (40) as a white powder. HPLC, Rt: 3.9 min (purity: 98.2%). LC/MS, M$^+$(ESI): 413.4, M$^-$(ESI): 411.3.

Example 41

Formation of N-(1-{[(7-chloro-3,4-dihydroisoquinolin-2(1H)-yl)sulfonyl]-methyl}-3,3-dimethylbutyl)-N-hydroxyformamide (41)

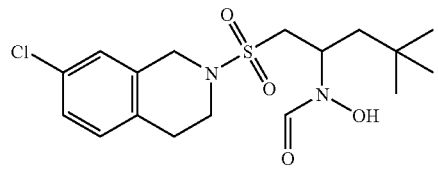

The title compound was prepared following procedure described in Example 40 step e), but starting from 7-chloro-2-(methylsulfonyl)-1,2,3,4-tetrahydroisoquinoline. After purification by crystallization in EtOAc/cHex, the title compound (41) was obtained as a yellow powder (181 mg, 46%). HPLC, Rt: 3.7 min (purity: 99.6%). LC/MS, M$^+$(ESI): 389.3, M$^-$(ESI): 387.3.

Example 42

Formation of N-(1-{[(6,7-dichloro-3,4-dihydroisoquinolin-2(1H)-yl)-sulfonyl]methyl}-3,3-dimethylbutyl)-N-hydroxyformamide (42)

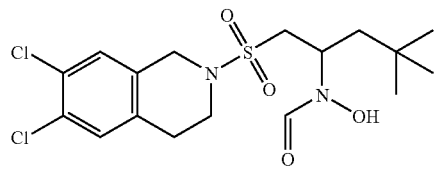

The title compound was prepared following procedure described in Example 40 step e), but starting from 6,7-dichloro-2-(methylsulfonyl)-1,2,3,4-tetrahydroisoquinoline. After purification by crystallization in EtOAc/cHex, the title compound (42) was obtained as a white powder (198 mg, 47%). HPLC, Rt: 3.9 min (purity: 98.8%). LC/MS, M$^+$(ESI): 423.3, M$^-$(ESI): 421.2.

Example 43

Formation of N-[3,3-dimethyl-1-({[6-(trifluoromethyl)-3,4-dihydro-isoquinolin-2(1H)-yl]sulfonyl}methyl)butyl]-N-hydroxyformamide (43)

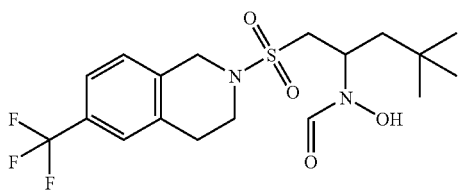

The title compound was prepared following procedure described in Example 40 step e), but starting from 2-(methylsulfonyl)-6-(trifluoromethyl)-1,2,3,4-tetrahydroisoquinoline. After purification by crystallization in EtOAc/cHex, the title compound (43) was obtained as a yellow powder (47 mg, 36%). HPLC, Rt: 3.9 min (purity: 100%). LC/MS, M+(ESI): 423.3, M−(ESI): 421.3.

Example 44

Formation of tert-butyl (2RS)-2-{(1SR)-2-[(6,7-dichloro-3,4-dihydro-isoquinolin-2(1H)-yl)sulfonyl]-1-[formyl(hydroxy)amino]ethyl}pyrrolidine-1-carboxylate (44)

Step a) Formation of a mixture of tert-butyl 2-{(E)-2-[(6,7-dichloro-3,4-dihydroisoquinolin-2(1H)-yl)sulfonyl]vinyl}pyrrolidine-1-carboxylate and tert-butyl 2-{(Z)-2-[(6,7-dichloro-3,4-dihydroisoquinolin-2(1H)-yl)sulfonyl]vinyl}pyrrolidine-1-carboxylate

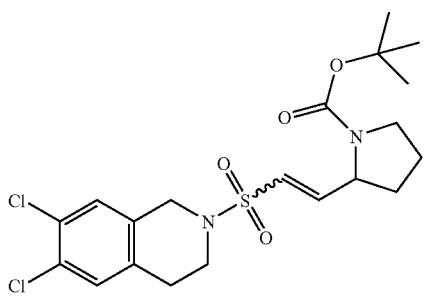

A solution of 6,7-dichloro-2-(methylsulfonyl)-1,2,3,4-tetrahydroisoquinoline (600 mg, 2.14 mmol) was prepared in anhydrous THF (5 ml) and cooled at −78° C. A solution of LiHMDS (1M in THF, 4.7 ml, 4.7 mmol) was added dropwise, followed by diethyl chlorophosphate (0.31 ml, 2.14 mmol). After 30 min. at −78° C., a solution of 2-formyl-pyrrolidine-1-carboxylic acid tert-butyl ester (512 mg, 2.57 mmol) in anhydrous THF (1 ml) was added. The resulting mixture was stirred at −78° C. for 1 hour, then at room temperature for 4 hours. The reaction mixture was diluted with EtOAc, then washed with water and brine. The organic layer was dried (MgSO4) and the solvents were removed under reduced pressure to give a colorless oil. After purification by flash chromatography on silica (cHex/EtOAc, gradient from 85/15 to 70/30), the title compound was obtained as a colorless oil consisting of a E/Z isomer mixture (616 mg, 62%, ratio 3/2). HPLC, Rt: 4.7 min and 4.8 min (total purity: 94%). LC/MS, M+(ESI): 461.3, M−(ESI): 459.8.

Step b) Formation of tert-butyl (2RS)-2-[(1RS)-2-[(6,7-dichloro-3,4-dihydroisoquinolin-2(1H)-yl)sulfonyl]-1-(hydroxyamino)ethyl]pyrrolidine-1-carboxylate and tert-butyl (2RS)-2-[(1SR)-2-[(6,7-dichloro-3,4-dihydroisoquinolin-2(1H)-yl)sulfonyl]-1-(hydroxyamino)ethyl]pyrrolidine-1-carboxylate

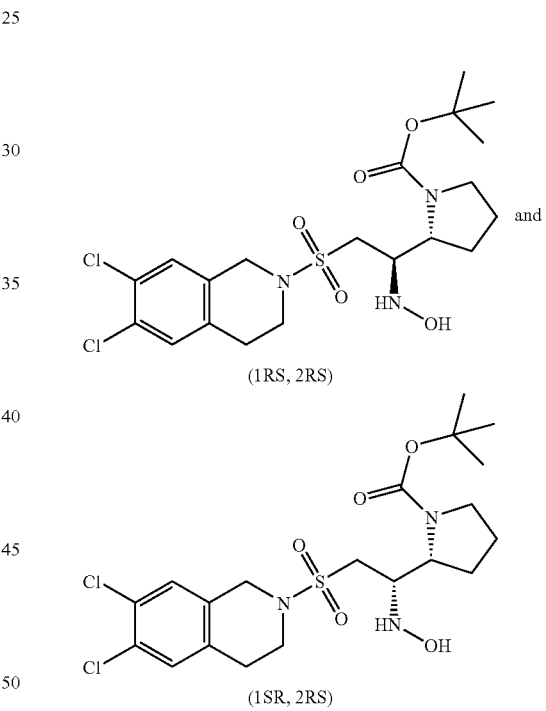

The title compound was prepared following procedure described in Example 22 step d), but starting from tert-butyl 2-{2-[(6,7-dichloro-3,4-dihydroisoquinolin-2(1H)-yl)sulfonyl]vinyl}pyrrolidine-1-carboxylate (E and Z isomer mixture). Purification by flash chromatography on silica (cHex/EtOAc, gradient from 4/1 to 1/1) allowed the separation of both diastereoisomer pairs (1RS,2RS) and (1SR,2RS).

The expected syn compound (1SR,2RS) was obtained as a colorless oil (200 mg, 31%). HPLC, Rt: 3.7 min (purity: 93.1%). LC/MS, M+(ESI): 494.4, M−(ESI): 492.2.

The expected anti compound (1RS,2RS) was obtained as a colorless oil (260 mg, 40%). HPLC, Rt: 3.7 min (purity: 73%). LC/MS, M+(ESI): 494.4.

Step c) Formation of tert-butyl (2RS)-2-{(1SR)-2-[(6,7-dichloro-3,4-dihydroisoquinolin-2(1H)-yl)sulfonyl]-1-[formyl(hydroxy)amino]ethyl}pyrrolidine-1-carboxylate

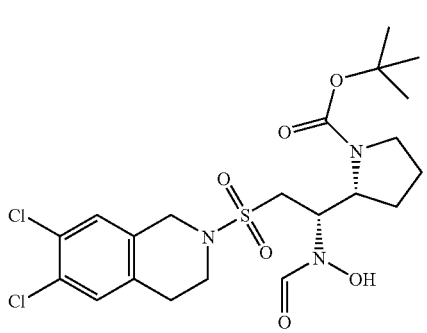

The title compound was prepared following procedure described in Example 22 step e), but starting from tert-butyl (2RS)-2-[(1SR)-2-[(6,7-dichloro-3,4-dihydroisoquinolin-2(1H)-yl)sulfonyl]-1-(hydroxyamino)ethyl]pyrrolidine-1-carboxylate. After purification by crystallization in EtOAc/pentane, the title compound (44) was obtained as a white powder (120 mg, 60%). HPLC, Rt: 4.0 min (purity: 94.1%). LC/MS, M⁺(ESI): 522.3, M⁻(ESI): 520.3.

Example 45

Formation of N-hydroxy-N-{(1S)-2-[(6-isopropyl-3,4-dihydroisoquinolin-2(1H)-yl)sulfonyl]-1-[(2R)-tetrahydrofuran-2-yl]ethyl}formamide (45)

Step a) Formation of 2-[(6-isopropyl-3,4-dihydroisoquinolin-2(1H)-yl)sulfonyl]-1-[(2R)-tetrahydrofuran-2-yl]ethanone

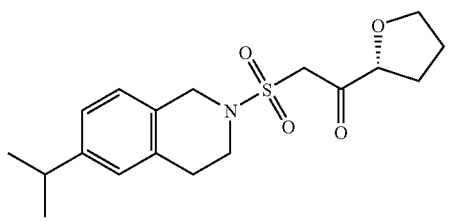

The title compound was prepared following procedure described in Example 22 step a), but starting from 6-isopropyl-2-(methylsulfonyl)-1,2,3,4-tetrahydroisoquinoline.
After purification by crystallization in EtOAc/pentane, the title compound was obtained as a brown powder (227 mg, 40%). HPLC, Rt: 4.0 min (purity: 76.5%). LC/MS, M⁺(ESI): 352.3, M⁻(ESI): 350.3.

Step b) Formation of 2-[(6-isopropyl-3,4-dihydroisoquinolin-2(1H)-yl)sulfonyl]-1-[(2R)-tetrahydrofuran-2-yl]ethanol

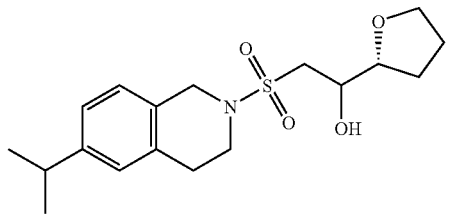

The title compound was prepared following procedure described in Example 22 step b), but starting from 2-[(6-isopropyl-3,4-dihydroisoquinolin-2(1H)-yl)sulfonyl]-1-[(2R)-tetrahydrofuran-2-yl]ethanone. The crude title compound was obtained as a yellow solid (200 mg, 88%) used without further purification in the next step. HPLC, Rt: 4.3 min (purity: 85.6%). LC/MS, M⁺(ESI): 354.3.

Step c) Formation of a mixture of 6-isopropyl-2-({2-[(2R)-tetrahydrofuran-2-yl]vinyl}-sulfonyl)-1,2,3,4-tetrahydroisoquinoline

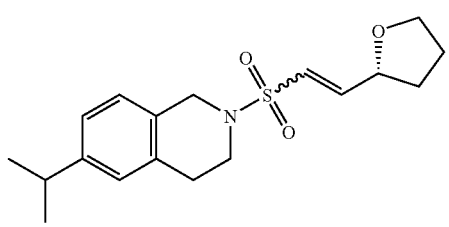

The title compound was prepared following procedure described in Example 22 step c), but starting from 2-[(6-isopropyl-3,4-dihydroisoquinolin-2(1H)-yl)sulfonyl]-1-[(2R)-tetrahydrofuran-2-yl]ethanol. The crude title compound was obtained as a brown oil (162 mg, 85%) used without further purification in the next step. HPLC, Rt: 4.1 min (purity: 89.2%). LC/MS, M⁺(ESI): 336.3.

Step d) Formation of (1S)—N-hydroxy-2-[(6-isopropyl-3,4-dihydroisoquinolin-2(1H)-yl)-sulfonyl]-1-[(2R)-tetrahydrofuran-2-yl]ethanamine

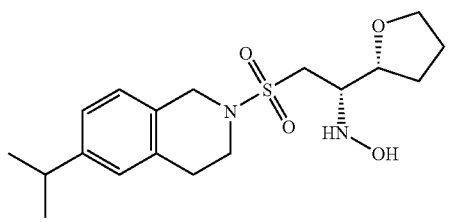

(1S, 2R)

The title compound was prepared following procedure described in Example 22 step d), but starting from 6-isopropyl-2-({2-[(2R)-tetrahydrofuran-2-yl]vinyl}sulfonyl)-1,2,3, 4-tetrahydroisoquinoline. Purification by flash chromatography on silica (cHex/EtOAc, gradient from 3/1 to 1/3) gave only the expected (1S,2R)-diastereoisomer (34 mg, 19%). HPLC, Rt: 3.0 min (purity: 86.3%). LC/MS, M⁺(ESI): 369.3.

Step e) Formation of N-hydroxy-N-{(1S)-2-[(6-isopropyl-3,4-dihydroisoquinolin-2(1H)-yl)sulfonyl]-1-[(2R)-tetrahydrofuran-2-yl]ethyl}formamide

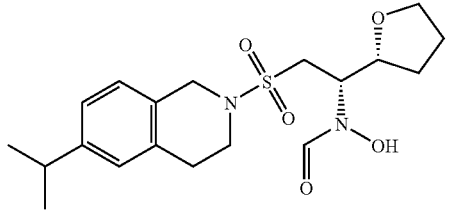

The title compound was prepared following procedure described in Example 22 step e), but starting from (1S)—N-hydroxy-2-[(6-isopropyl-3,4-dihydroisoquinolin-2(1H)-yl)sulfonyl]-1-[(2R)-tetrahydrofuran-2-yl]ethanamine. After purification by crystallization in EtOAc/pentane, the title compound (45) was obtained as a white powder (18 mg, 49%). HPLC, Rt: 4.0 min (purity: 100%). LC/MS, M⁺(ESI): 397.3, M⁻(ESI): 395.3.

Example 46

Formation of tert-butyl (2RS)-2-{(1RS)-2-[(6,7-dichloro-3,4-dihydro-isoquinolin-2(1H)-yl)sulfonyl]-1-[formyl(hydroxy)amino]ethyl}pyrrolidine-1-carboxylate (46)

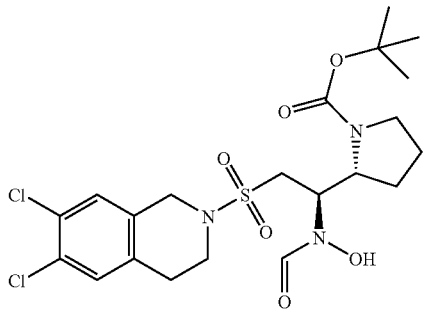

The title compound was prepared following procedure described in Example 22 step e), but starting from tert-butyl (2RS)-2-[(1RS)-2-[(6,7-dichloro-3,4-dihydroisoquinolin-2(1H)-yl)sulfonyl]-1-(hydroxyamino)ethyl]pyrrolidine-1-carboxylate. After purification by crystallization in EtOAc/pentane, the title compound (46) was obtained as a white powder (210 mg, 79%). HPLC, Rt: 4.4 min (purity: 91.9%). LC/MS, M⁺(ESI): 522.3, M⁻(ESI): 520.3.

Example 47

Formation of N-hydroxy-N-(1-[(2R)-tetrahydrofuran-2-yl]-2-{[6-(tri-fluoromethyl)-3,4-dihydroisoquinolin-2(1H)-yl]sulfonyl}ethyl)formamide (47)

Step a) Formation of 1-[(2R)-tetrahydrofuran-2-yl]-2-{[6-(trifluoromethyl)-3,4-dihydroisoquinolin-2(1H)-yl]sulfonyl}ethanone

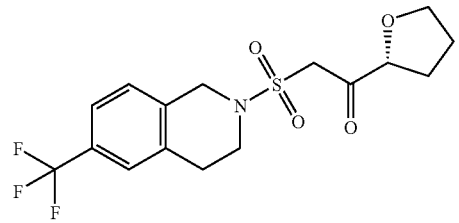

The title compound was prepared following procedure described in Example 22 step a), but starting from 2-(methylsulfonyl)-6-(trifluoromethyl)-1,2,3,4-tetrahydroisoquinoline. After purification by crystallization in EtOAc/pentane, the title compound was obtained as a yellow powder (220 mg, 36%). HPLC, Rt: 3.7 min (purity: 76.8%). LC/MS, M⁺(ESI): 378.2, M⁻(ESI): 376.2.

Step b) Formation of 1-[(2R)-tetrahydrofuran-2-yl]-2-{[6-(trifluoromethyl)-3,4-dihydro-isoquinolin-2(1H)-yl]sulfonyl}ethanol

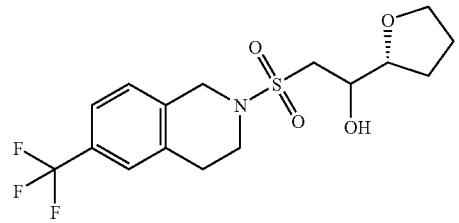

The title compound was prepared following procedure described in Example 22 step b), but starting from 1-[(2R)-tetrahydrofuran-2-yl]-2-{[6-(trifluoromethyl)-3,4-dihydroisoquinolin-2(1H)-yl]sulfonyl}ethanone. The crude title compound was obtained as a white solid (170 mg, 77%) used without further purification in the next step. HPLC, Rt: 4.0 min (purity: 86.0%). LC/MS, M⁺(ESI): 380.2.

Step c) Formation of a mixture 2-({2-[(2R)-tetrahydrofuran-2-yl]vinyl}sulfonyl)-6-(tri-fluoromethyl)-1,2,3,4-tetrahydroisoquinoline

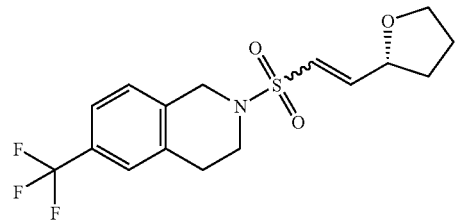

The title compound was prepared following procedure described in Example 22 step c), but starting from 1-[(2R)-tetrahydrofuran-2-yl]-2-{[6-(trifluoromethyl)-3,4-dihydroisoquinolin-2(1H)-yl]sulfonyl}ethanol. The crude title compound was obtained as a brown solid (163 mg, 100%) used without further purification in the next step. HPLC, Rt: 4.6 min (purity: 90.1%). LC/MS, M+(ESI): 362.2.

Step d) Formation of N-hydroxy-1-[(2R)-tetrahydrofuran-2-yl]-2-{[6-(trifluoromethyl)-3,4-dihydroisoquinolin-2(1H)-yl]sulfonyl}ethanamine

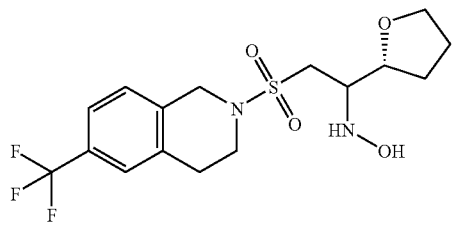

The title compound was prepared following procedure described in Example 22 step d), but starting from 2-({2-[(2R)-tetrahydrofuran-2-yl]vinyl}sulfonyl)-6-(trifluoromethyl)-1,2,3,4-tetrahydroisoquinoline (E and Z isomer mixture). After purification by flash chromatography on silica (cHex/EtOAc, gradient from 3/1 to 1/3), the title compound was obtained as a white powder consisting of a mixture of both diastereoisomers (1R,2R) and (1S,2R) (40 mg, 22%). LC/MS, M+(ESI): 395.4.

Step e) Formation of N-hydroxy-N-(1-[(2R)-tetrahydrofuran-2-yl]-2-{[6-(trifluoromethyl)-3,4-dihydroisoquinolin-2(1H)-yl]sulfonyl}ethyl)formamide

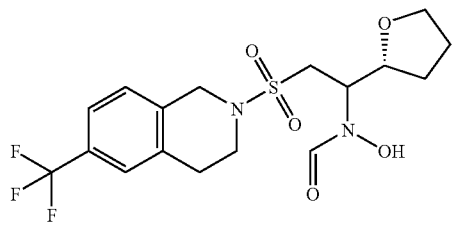

The title compound was prepared following procedure described in Example 22 step e), but starting from N-hydroxy-1-[(2R)-tetrahydrofuran-2-yl]-2-{[6-(trifluoromethyl)-3,4-dihydroisoquinolin-2(1H)-yl]sulfonyl}ethanamine. After purification by crystallization in EtOAc/pentane, the title compound (47) was obtained as a white powder (33 mg, 77%) consisting of a mixture of both (1R,2R)- and (1S,2R)-diastereoisomers (ratio 1/1). HPLC (gradient 20 min, ELSD detector), Rt: 13.2 and 13.4 min (total purity: 94.0%). LC/MS, M+(ESI): 423.3, M−(ESI): 421.1.

Example 48

Formation of N-(1-{[(7-chloro-3,4-dihydroisoquinolin-2(1H)-yl)sulfonyl]-methyl}-3-hydroxypropyl)-N-hydroxyformamide (48)

Step a) Formation of N-(3-{[tert-butyl(dimethyl)silyl]oxy}-1-{[(7-chloro-3,4-dihydroisoquinolin-2(1H)-yl)sulfonyl]methyl}propyl)-N-hydroxyformamide

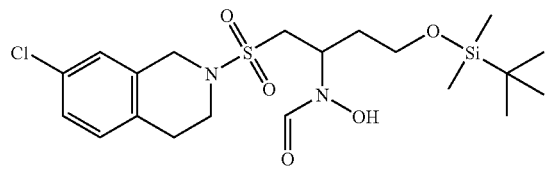

The title compound was prepared following procedure described in Example 40 step e), but starting from 7-chloro-2-(methylsulfonyl)-1,2,3,4-tetrahydroisoquinoline and 3-[(tert-butyldimethylsilyl)oxy]-1-propanal. The crude title compound was obtained as a yellow oil (238 mg, quantitative) used in the next step without further purification. LC/MS, M+(ESI): 477.0, M−(ESI): 475.3.

Step b) Formation of N-(1-{[(7-chloro-3,4-dihydroisoquinolin-2(1H)-yl)sulfonyl]methyl}-3-hydroxypropyl)-N-hydroxyformamide

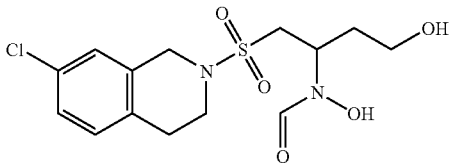

A solution of N-(3-{[tert-butyl(dimethyl)silyl]oxy}-1-{[(7-chloro-3,4-dihydroisoquinolin-2(1H)-yl)sulfonyl]methyl}propyl)-N-hydroxyformamide (238 mg) was prepared in THF (5 ml) and tetrabutylammonium fluoride (1M in THF, 0.5 ml, 0.5 mmol) was added. The reaction mixture was stirred at RT for 15 hours. The solvent was removed under reduced pressure. The residue was taken up with EtOAc and washed with water. The organic layer was dried (MgSO4) and the solvent was removed under reduced pressure to give an oil. After purification by crystallization in EtOAc/cHex, the title compound (48) was obtained as yellow powder (17 mg, 10% overall yield). HPLC, Rt: 2.9 min (purity: 74%). LC/MS, M+(ESI): 363.1, M−(ESI): 361.1.

Example 49

Formation of N-[2-[(6,7-dichloro-3,4-dihydroisoquinolin-2(1H)-yl)-sulfonyl]-1-(hydroxymethyl)ethyl]-N-hydroxyformamide (49)

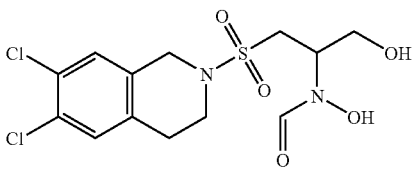

The title compound was prepared following procedure described in Example 40 step e), but starting from 6,7- dichloro-2-(methylsulfonyl)-1,2,3,4-tetrahydroisoquinoline and glycolaldehyde. After purification by crystallization in DCM/Et₂O, the title compound (49) was obtained as a white powder (123 mg, 27%). HPLC, Rt: 3.3 min (purity: 94.1%). LC/MS, M⁺(ESI): 383.1, M⁻(ESI): 381.0.

Example 50

Formation of N-[1-({[7-(4-fluorophenyl)-3,4-dihydroisoquinolin-2(1H)-yl]sulfonyl}methyl)-2-methylpropyl]-N-hydroxyformamide (50)

Step a) Formation of 7-(4-fluorophenyl)-2-(methylsulfonyl)-1,2,3,4-tetrahydroisoquinoline

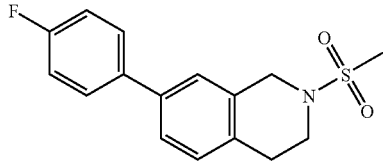

A mixture of 7-bromo-2-(methylsulfonyl)-1,2,3,4-tetrahydroisoquinoline (2.90 g, 10.0 mmol), 4-fluorophenylboronic acid (2.10 g, 15.0 mmol), anhydrous potassium carbonate (4.15 g, 30.0 mmol) and triphenylphosphine (525 mg, 2.0 mmol) was prepared in MeOH (20 ml) and 1,4-dioxane (10 ml). Argon was bubbled for 10 min., then Pd(OAc)₂ (112 mg, 0.50 mmol) was added. The resulting mixture was refluxed for 5 hours. The reaction mixture was diluted with Et₂O (50 ml) and the resulting suspension was filtered trough a pad of Celite. The filtrate was evaporated under reduced pressure. The residue was taken up with Et₂O and washed with water (3×) and brine. The organic layer was dried (MgSO₄) and the solvent was removed under reduced pressure to give a black oil. After purification by flash chromatography on silica (cHex/EtOAc, gradient from 3/1 to 3/2), the title compound was obtained as a beige solid (2.50 g, 82%). HPLC, Rt: 4.4 min (purity: 98.8%). LC/MS, M⁺(ESI): 306.2.

Step b) Formation of N-[1-({[7-(4-fluorophenyl)-3,4-dihydroisoquinolin-2(1H)-yl]-sulfonyl}methyl)-2-methylpropyl]-N-hydroxyformamide

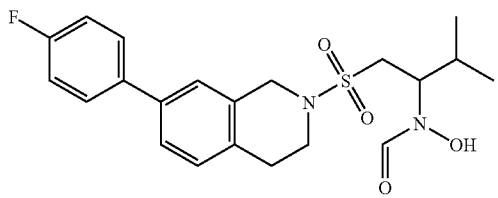

The title compound was prepared following procedure described in Example 40 step e), but starting from 7-(4-fluorophenyl)-2-(methylsulfonyl)-1,2,3,4-tetrahydroisoquinoline and isobutyraldehyde. After purification by crystallization in EtOAc/pentane, the title compound (50) was obtained as a white powder (319 mg, 63%). HPLC, Rt: 4.6 min (purity: 99.2%). LC/MS, M⁺(ESI): 421.3, M⁻(ESI): 419.1.

Example 51

Formation of N-hydroxy-N-(1-{[(7-isopropoxy-3,4-dihydroisoquinolin-2(1H)-yl)sulfonyl]methyl}-3-methylbutyl)formamide (51)

Step a) Formation of tert-butyl 7-isopropoxy-3,4-dihydroisoquinoline-2(1H)-carboxylate

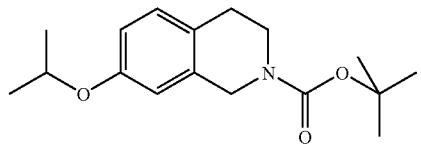

The title compound was prepared following procedure described in Example 40 step a), but starting from isopropyl iodide. The title compound was obtained as a solid (1.2 g, 48%). TLC—Chloroform/methanol (9/1): R_f=0.75. ¹H-NMR (CDCl₃, 400 MHz) δ 1.33 (6H, d), 1.50 (9H, s), 2.76 (2H, m), 3.64 (2H, m), 4.52 (3H, m), 6.64 (1H, s), 6.74 (1H, d), 7.04 (1H, d).

Step b) Formation of 7-isopropoxy-1,2,3,4-tetrahydroisoquinoline hydrochloride

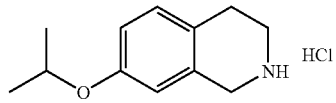

The title compound was prepared following procedure described in Example 40 step e), but starting from tert-butyl 7-isopropoxy-3,4-dihydroisoquinoline-2(1H)-carboxylate. The title compound was obtained as a solid (750 mg, 96%). TLC—Chloroform/methanol (9/1): R_f=0.15. ¹H NMR (DMSO-d₆, 400 MHz) δ 1.24 (6H, d), 2.90 (2H, m), 3.32 (2H, m), 4.17 (2H, m), 4.56 (1H, m), 6.77 (1H, s), 6.80 (1H, d), 7.09 (1H, d), 9.54 (2H, br. s).

Step c) Formation of 7-isopropoxy-2-(methylsulfonyl)-1,2,3,4-tetrahydroisoquinoline

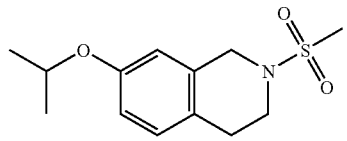

The title compound was prepared following procedure described in Example 1 step a), but starting from 7-isopropoxy-1,2,3,4-tetrahydroisoquinoline hydrochloride and one additional equivalent of DIEA. After purification by crystallization in Et₂O/pentane, the title compound was obtained as Step d) Formation of N-hydroxy-N-(1-{[(7-isopropoxy-3,4-dihydroisoquinolin-2(1H)-yl)sulfonyl]methyl}-3-methylbutyl)formamide

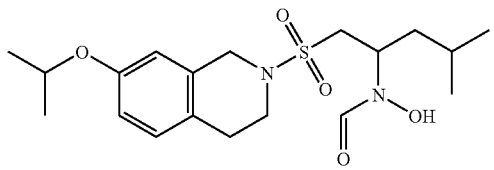

The title compound was prepared following procedure described in Example 40 step e), but starting from 7-isopropoxy-2-(methylsulfonyl)-1,2,3,4-tetrahydroisoquinoline and isovaleraldehyde. After purification by crystallization in EtOAc/pentane, the title compound (51) was obtained as a white powder (276 mg, 58%). HPLC, Rt: 4.5 min (purity: 98.8%). LC/MS, M+(ESI): 399.3, M−(ESI): 397.2.

Example 52

Formation of N-[2-[(7-fluoro-3,4-dihydroisoquinolin-2(1H)-yl)sulfonyl]-1-(3-furyl)ethyl]-N-hydroxyformamide (52)

Step a) Formation of 7-fluoro-2-(methylsulfonyl)-1,2,3,4-tetrahydroisoquinoline

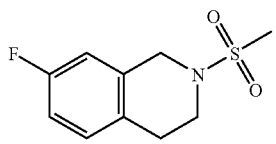

The title compound was prepared following procedure described in Example 1 step a), but starting from 7-fluoro-1,2,3,4-tetrahydroisoquinoline hydrochloride and one additional equivalent of DIEA. After purification by crystallization in Et₂O/pentane, the title compound was obtained as an off-white powder (2.1 g, 80%). HPLC, Rt: 2.5 min (purity: 100%). LC/MS, M+(ESI): 230.1.

Step b) Formation of N-[2-[(7-fluoro-3,4-dihydroisoquinolin-2(1H)-yl)sulfonyl]-1-(3-furyl)ethyl]-N-hydroxyformamide

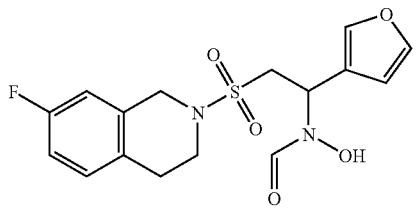

The title compound was prepared following procedure described in Example 40 step e), but starting from 7-fluoro-2-(methylsulfonyl)-1,2,3,4-tetrahydroisoquinoline and 3-furaldehyde. After purification by crystallization in EtOAc/Et₂O, the title compound (52) was obtained as a white powder (248 mg, 56%). HPLC, Rt: 3.3 min (purity: 98.7%). LC/MS, M+(ESI): 369.1, M−(ESI): 367.1.

Example 53

Formation of N-{1-(1-benzylpiperidin-4-yl)-2-[(7-fluoro-3,4-dihydro-isoquinolin-2(1H)-yl)sulfonyl]ethyl}-N-hydroxyformamide (53)

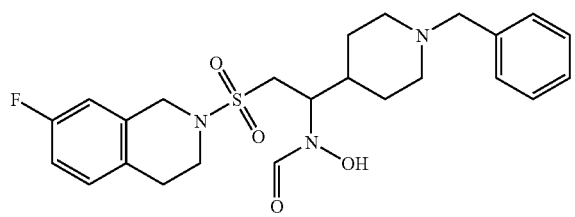

The title compound was prepared following procedure described in Example 40 step e), but starting from 7-fluoro-2-(methylsulfonyl)-1,2,3,4-tetrahydroisoquinoline and 1-benzyl-piperidine-4-carbaldehyde. After purification by crystallization in EtOAc/pentane, the title compound (53) was obtained as an off-white powder (293 mg, 51%). HPLC, Rt: 2.9 min (purity: 97.4%). LC/MS, M+(ESI): 476.4, M−(ESI): 474.0.

Example 54

Formation of N-[1-{[(7-tert-butyl-3,4-dihydroisoquinolin-2(1H)-yl)-sulfonyl]methyl}-3-(methylthio)propyl]-N-hydroxyformamide (54)

Step a) Formation of N-[2-(4-tert-butylphenyl)ethyl]methanesulfonamide

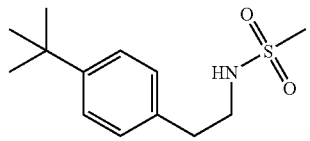

The title compound was prepared following procedure described in Example 19 step a), but starting from 4-(tert-butyl)phenethylamine. After purification by crystallization in DCM/Et₂O/pentane, the title compound was obtained as a white powder (5.9 g, 82%). HPLC, Rt: 4.3 min (purity: 100%). LC/MS, M+(ESI): 256.2, M−(ESI): 254.2.

Step b) Formation of 7-tert-butyl-2-(methylsulfonyl)-1,2,3,4-tetrahydroisoquinoline

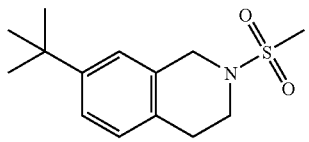

The title compound was prepared following procedure described in Example 19 step b), but starting from N-[2-(4-tert-butylphenyl)ethyl]methanesulfonamide. After purification by crystallization in DCM/Et$_2$O/pentane, the title compound was obtained as a white powder (910 mg, 87%). HPLC, Rt: 4.6 min (purity: 98.4%). LC/MS, M$^+$(ESI): 268.2.

Step c) Formation of N-[1-{[(7-tert-butyl-3,4-dihydroisoquinolin-2(1H)-yl)sulfonyl]-methyl}-3-(methylthio)propyl]-N-hydroxyformamide

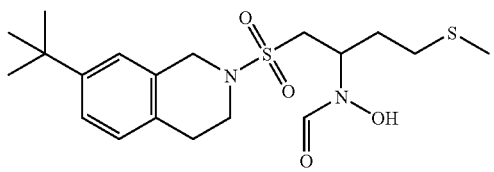

The title compound was prepared following procedure described in Example 40 step e), but starting from 7-tert-butyl-2-(methylsulfonyl)-1,2,3,4-tetrahydroisoquinoline and 3-(methylthio)propionaldehyde. After purification by crystallization in EtOAc/pentane, the title compound (54) was obtained as a white powder (224 mg, 45%). HPLC, Rt: 4.5 min (purity: 99.5%). LC/MS, M$^+$(ESI): 415.2, M$^-$(ESI): 413.1.

Example 55

Formation of N-(1-{[(7-bromo-3,4-dihydroisoquinolin-2(1H)-yl)-sulfonyl]methyl}-3-methylbutyl)-N-hydroxyformamide (55)

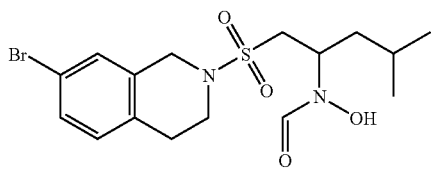

The title compound was prepared following procedure described in Example 40 step e), but starting from 7-bromo-2-(methylsulfonyl)-1,2,3,4-tetrahydroisoquinoline and isovaleraldehyde. After purification by crystallization in EtOAc, the title compound (55) was obtained as a white powder (202 mg, 40%). HPLC, Rt: 4.2 min (purity: 99.2%). LC/MS, M$^+$(ESI): 419.1, M$^-$(ESI): 417.0.

Example 56

Formation of N-{2-[(7-bromo-3,4-dihydroisoquinolin-2(1H)-yl)sulfonyl]-1,1-dimethylethyl}-N-hydroxyformamide (56)

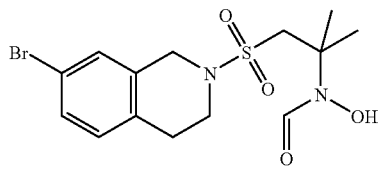

The title compound was prepared following procedure described in Example 40 step e), but starting from 7-bromo-2-(methylsulfonyl)-1,2,3,4-tetrahydroisoquinoline and acetone. After purification by crystallization in MeOH, the title compound (56) was obtained as a white powder (253 mg, 54%). HPLC, Rt: 3.4 min (purity: 96.9%). LC/MS, M$^+$(ESI): 391.1, M$^-$(ESI): 388.9.

Example 57

Formation of N-(2-(benzyloxy)-1-{[(7-tert-butyl-3,4-dihydroisoquinolin-2(1H)-yl)sulfonyl]methyl}ethyl)-N-hydroxyformamide (57)

The title compound was prepared following procedure described in Example 40 step e), but starting from 7-tert-butyl-2-(methylsulfonyl)-1,2,3,4-tetrahydroisoquinoline and benzyloxyacetaldehyde. After purification by crystallization in Et$_2$O, the title compound (57) was obtained as a white powder (270 mg, 59%). HPLC, Rt: 4.9 min (purity: 100%). LC/MS, M$^+$(ESI): 461.3, M$^-$(ESI): 459.1.

Example 58

Formation of N-(2-(benzyloxy)-1-{[(7-chloro-3,4-dihydroisoquinolin-2(1H)-yl)sulfonyl]methyl}ethyl)-N-hydroxyformamide (58)

The title compound was prepared following procedure described in Example 40 step e), but starting from 7-chloro- 2-(methylsulfonyl)-1,2,3,4-tetrahydroisoquinoline and benzyloxyacetaldehyde. After purification by crystallization in Et₂O/pentane, the title compound (58) was obtained as a white powder (126 mg, 29%). HPLC, Rt: 4.3 min (purity: 97.9%). LC/MS, M⁺(ESI): 439.3, M⁻(ESI): 436.9.

Example 59

Formation of N-[2-(benzyloxy)-1-({[7-(trifluoromethyl)-3,4-dihydro-isoquinolin-2(1H)-yl]sulfonyl}methyl)ethyl]-N-hydroxyformamide (59)

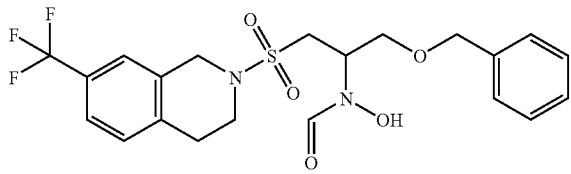

The title compound was prepared following procedure described in Example 40 step e), but starting from 2-(methylsulfonyl)-7-(trifluoromethyl)-1,2,3,4-tetrahydroisoquinoline and benzyloxyacetaldehyde. After purification by crystallization in Et₂O, the title compound (59) was obtained as a white powder (204 mg, 43%). HPLC, Rt: 4.5 min (purity: 100%). LC/MS, M⁺(ESI): 473.3, M⁻(ESI): 470.9.

Example 60

Formation of N-{1-cyclopentyl-2-[(7-fluoro-3,4-dihydroisoquinolin-2(1H)-yl)sulfonyl]ethyl}-N-hydroxyformamide (60)

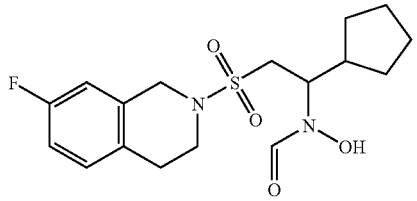

The title compound was prepared following procedure described in Example 40 step e), but starting from 7-fluoro-2-(methylsulfonyl)-1,2,3,4-tetrahydroisoquinoline and cyclopentanecarboxaldehyde. After purification by crystallization in EtOAc/pentane, the title compound (60) was obtained as a white powder (190 mg, 47%). HPLC, Rt: 3.7 min (purity: 100%). LC/MS, M⁺(ESI): 371.2, M⁻(ESI): 369.1.

Example 61

Formation of N-[2-[(7-chloro-3,4-dihydroisoquinolin-2(1H)-yl)sulfonyl]-1-(phenoxymethyl)ethyl]-N-hydroxyformamide (61)

Step a) Formation of 1-[(7-chloro-3,4-dihydroisoquinolin-2(1H)-yl)sulfonyl]-3-phenoxyacetone

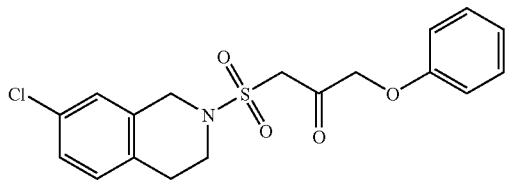

solution of 7-chloro-2-(methylsulfonyl)-1,2,3,4-tetrahydroisoquinoline (400 mg, 1.63 mmol) was prepared in anhydrous THF (8 ml) and cooled at −78° C. Then a solution of LiHMDS (1M in THF, 3.6 ml, 3.6 mmol) was added dropwise. After 5 min., methyl phenoxyacetate (0.26 ml, 1.79 mmol) was added. The resulting mixture was stirred at −78° C. for 1 hour, then at RT for 15 hours. The reaction mixture was diluted with EtOAc (20 ml), then washed with a 1N aqueous solution of HCl (2×20 ml) and a saturated aqueous solution of NaHCO₃ (20 ml). The aqueous layers were extracted with EtOAc (20 ml). The organic layers were combined, dried (MgSO₄) and the solvent was removed under reduced pressure. After purification by crystallization in EtOAc/Et₂O/pentane, the title compound was obtained as an off-white powder (494 mg, 80%). HPLC, Rt: 4.9 min (purity: 95.6%). LC/MS, M⁺(ESI): 380.2, M⁻(ESI): 378.2.

Step b) Formation of 1-[(7-chloro-3,4-dihydroisoquinolin-2(1H)-yl)sulfonyl]-3-phenoxy-propan-2-ol

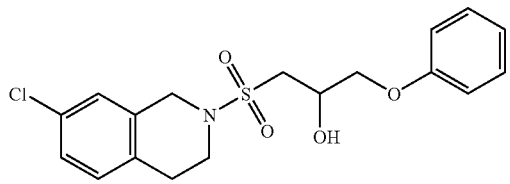

A suspension of 1-[(7-chloro-3,4-dihydroisoquinolin-2(1H)-yl)sulfonyl]-3-phenoxyacetone (468 mg, 1.23 mmol) was prepared in MeOH (15 ml), then NaBH4 (77 mg, 1.85 mmol) was added portionwise. The resulting mixture was stirred at RT for 1 h00. The reaction mixture was concentrated under reduced pressure, then diluted with EtOAc (30 ml) and washed with a 1N aqueous solution of HCl (15 ml) and a saturated aqueous solution of NaHCO₃ (15 ml). The aqueous layers were extracted with EtOAc (30 ml). The organic layers were combined, dried (MgSO₄) and the solvent was removed under reduced pressure. After purification by crystallization in EtOAc/pentane, the title compound was obtained as a white powder (415 mg, 88%). HPLC, Rt: 4.5 min (purity: 99.2%). LC/MS, M⁺(ESI): 382.2.

Step c) Formation of a mixture of 7-chloro-2-{[(1E)-3-phenoxyprop-1-en-1-yl]sulfonyl}-1,2,3,4-tetrahydroisoquinoline and 7-chloro-2-{[(1Z)-3-phenoxyprop-1-en-1-yl]sulfonyl}-1,2,3,4-tetrahydroisoquinoline

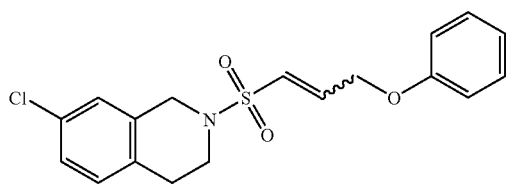

A solution of 1-[(7-chloro-3,4-dihydroisoquinolin-2(1H)-yl)sulfonyl]-3-phenoxypropan-2-ol (370 mg, 0.97 mmol) and Et₃N (0.32 ml, 2.33 mmol) in anhydrous DCM (5 ml) was cooled at 0° C., then methanesulfonyl chloride (0.09 ml, 1.16 mmol) was added dropwise. The resulting mixture was stirred at 0° C. for 1 h00, then at RT for 20 h00. The reaction mixture was diluted with DCM (10 ml), then washed with a 1N aqueous solution of HCl (2×10 ml) and a saturated aqueous solution of NaHCO₃ (10 ml). The aqueous layers were extracted with DCM (2×10 ml). The organic layers were combined, dried (MgSO₄) and the solvent was removed under reduced pressure to give the title compound as a pale yellow powder (294 mg, 83%), mixture of E/Z isomers (ratio 85/15 by HPLC). HPLC, Rt: 5.3 min and 5.4 min (total purity: 98%). LC/MS, M⁺(ESI): 364.1, M⁻(ESI): 362.0.

Step d) Formation of N-[2-[(7-chloro-3,4-dihydroisoquinolin-2(1H)-yl)sulfonyl]-1-(phenoxymethyl)ethyl]-N-hydroxyformamide

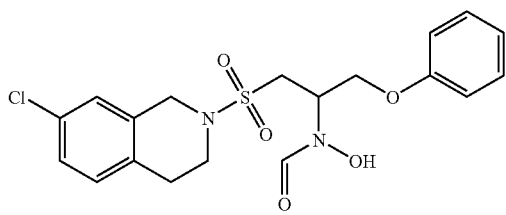

A solution of 7-chloro-2-{(3-phenoxyprop-1-en-1-yl)sulfonyl}-1,2,3,4-tetrahydroisoquinoline (E and Z mixture, 279 mg, 0.77 mmol) was prepared in THF (7 ml) and a 50% aqueous solution of NH$_2$OH (0.7 ml, 11.5 mmol)) was added. The resulting biphasic mixture was heated at 60° C. for 3 h00. The reaction mixture was washed with brine (5 ml) and the layers were separated. The organic layer was dried (MgSO$_4$) and the solvent was removed under reduced pressure to give a yellow oil. A mixture of formic acid (2.0 ml) and acetic anhydride (0.5 ml) was stirred at 0° C. for 30 min., then a solution of the previous oil in anhydrous THF (5 ml) was added and the resulting mixture was stirred at 0° C. for 10 min., then at RT for 90 min. The mixture was evaporated under reduced pressure. The residue was taken up with MeOH (15 ml) and heated at 60° C. for 2 h00. The mixture was cooled at RT and a solid precipitated out. The solid was filtered, washed with MeOH (3x) and dried under reduced pressure to give the title compound (61) as a white powder (255 mg, 78%). HPLC, Rt: 4.4 min (purity: 98.1%). LC/MS, M$^+$(ESI): 425.2, M$^-$(ESI): 423.1.

Example 62

Formation of N-(1-{[(7-chloro-3,4-dihydroisoquinolin-2(1H)-yl)-sulfonyl]methyl}cyclopentyl)-N-hydroxyformamide (62)

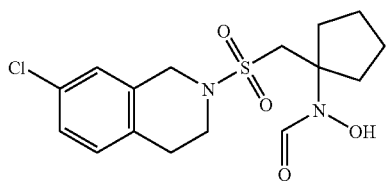

The title compound was prepared following procedure described in Example 40 step e), but starting from 7-chloro-2-(methylsulfonyl)-1,2,3,4-tetrahydroisoquinoline and cyclopentanone. After purification by crystallization in Et2O/pentane, the title compound (62) was obtained as a white powder (272 mg, 37%). HPLC, Rt: 3.6 min (purity: 96.2%). LC/MS, M$^+$(ESI): 373.1, M$^-$(ESI): 371.0.

Example 63

Formation of N-[2,2-dimethyl-1-({[6-(trifluoromethyl)-3,4-dihydro-isoquinolin-2(1H)-yl]sulfonyl}methyl)heptyl]-N-hydroxyformamide (63)

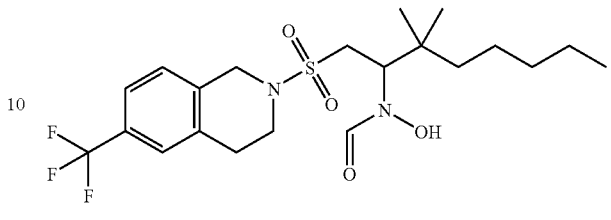

A solution of N-[2,2-dimethyl-1-({[6-(trifluoromethyl)-3,4-dihydroisoquinolin-2(1H)-yl]sulfonyl}methyl)hept-4-yn-1-yl]-N-hydroxyformamide (370.00 mg, 0.80 mmol) was prepared in EtOH (15 ml) and hydrogenated over 10% Pd/C under 25 bars for 3 h00. The reaction mixture was filtered through a Celite pad and the solvent was evaporated under reduced pressure. The residue was taken up with DCM and evaporated to give the title compound (63) as a beige foam (364 mg, 98%). HPLC, Rt: 5.3 min (purity: 90.5%). LC/MS, M$^+$(ESI): 465.4, M$^-$(ESI): 463.0.

Example 64

Formation of N-{2-[(7-bromo-3,4-dihydroisoquinolin-2(1H)-yl)sulfonyl]-1-cyclopentylethyl}-N-hydroxyformamide (64)

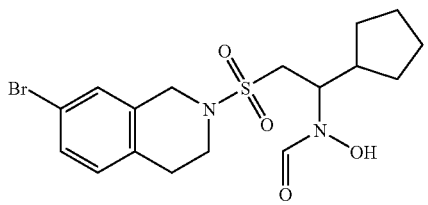

The title compound was prepared following procedure described in Example 40 step e), but starting from 7-bromo-2-(methylsulfonyl)-1,2,3,4-tetrahydroisoquinoline and cyclopentanecarboxaldehyde. After purification by crystallization in EtOAc/cHex, the title compound (64) was obtained as a white powder (3.1 g, 77%). HPLC, Rt: 4.1 min (purity: 95.1%). LC/MS, M$^+$(ESI): 433.1, M$^-$(ESI): 430.9.

Example 65

Formation of N-(1-{[(7-chloro-3,4-dihydroisoquinolin-2(1H)-yl)sulfonyl]methyl}-2,2-dimethylpropyl)-N-hydroxyformamide (65)

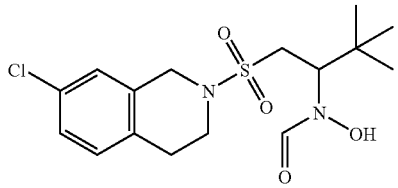

The title compound was prepared following procedure described in Example 40 step e), but starting from 7-chloro-2-(methylsulfonyl)-1,2,3,4-tetrahydroisoquinoline and trimethylacetaldehyde. After purification by crystallization in EtOAc/pentane, the title compound (65) was obtained as a white powder. HPLC, Rt: 3.9 min (purity: 88.6%). LC/MS, M⁺(ESI): 375.2, M⁻(ESI): 373.1.

Example 66

Formation of N-[2-[(7-tert-butyl-3,4-dihydroiso-quinolin-2(1H)-yl)sulfonyl]-1-(tetrahydro-2H-pyran-4-yl)ethyl]-N-hydroxyformamide (66)

Step a) Formation of 2-[(7-tert-butyl-3,4-dihydroiso-quinolin-2(1H)-yl)sulfonyl]-J-(tetrahydro-2H-pyran-4-yl)ethanol

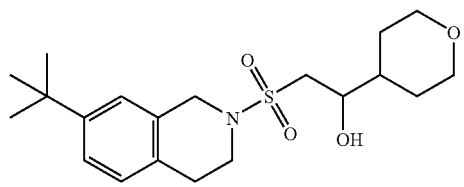

A solution of 7-tert-butyl-2-(methylsulfonyl)-1,2,3,4-tetrahydroisoquinoline (400 mg, 1.5 mmol) was prepared in anhydrous THF (8 ml) and cooled at −78° C. Then a solution of LiHMDS (1M in THF, 3.3 ml, 3.3 mmol) was added dropwise. After 5 min., methyl tetrahydro-2H-pyran-4-carboxylate (0.22 ml, 1.65 mmol) was added. The resulting mixture was stirred at −78° C. for 5 min., then at RT for 1 h30. The reaction mixture was cooled at 0° C., then a solution of HCl (1M in MeOH, 5.3 ml) and MeOH (5 ml) were added. NaBH₄ (85 mg, 2.24 mmol) was added and the resulting suspension was stirred at 0° C. for 25 min. The reaction mixture was evaporated under reduced pressure. The residue was taken up with EtOAc (20 ml) and washed with a 1N aqueous solution of HCl (2×20 ml). The aqueous layers were extracted with EtOAc (20 ml). The organic layers were combined, dried (MgSO₄) and the solvents were removed under reduced pressure to give a colorless oil. After purification by crystallization in EtOAc/pentane, the title compound was obtained as a white powder (455 mg, 80%). HPLC, Rt: 4.4 min (purity: 96.8%). LC/MS, M⁺(ESI): 382.3.

Step b) Formation of N-[2-[(7-tert-butyl-3,4-dihydroisoquinolin-2(1H)-yl)sulfonyl]-1-(tetrahydro-2H-pyran-4-yl)ethyl]-N-hydroxyformamide

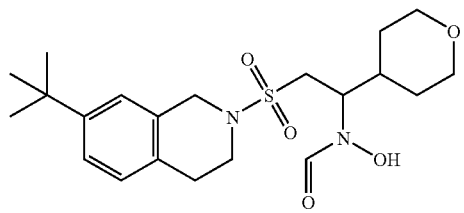

A solution of 2-[(7-tert-butyl-3,4-dihydroisoquinolin-2 (1H)-yl)sulfonyl]-1-(tetrahydro-2H-pyran-4-yl)ethanol (431 mg, 1.13 mmol) and Et₃N (0.38 ml, 2.71 mmol) in anhydrous THF (10 ml) was cooled at 0° C., then methanesulfonyl chloride (0.105 ml, 1.36 mmol) was added dropwise. The resulting mixture was stirred at 0° C. for 15 min, then at 60° C. for 20 h00. A 50% aqueous solution of NH₂OH (1.0 ml, 16.9 mmol)) was added and the resulting mixture was stirred at 60° C. for 2 h30. Then the reaction mixture was washed with brine (5 ml), dried (MgSO₄) and the solvent was removed under reduced pressure to give a yellow oil. A mixture of formic acid (3.2 ml) and acetic anhydride (0.8 ml) was stirred at 0° C. for 30 min., then a solution of the previous oil in anhydrous THF (5 ml) was added and the resulting mixture was stirred at 0° C. for 10 min., then at RT for 30 min. The mixture was evaporated under reduced pressure. The residue was taken up with MeOH (10 ml) and heated at 60° C. for 30 min. The reaction mixture was evaporated under reduced pressure, then the residue was taken up with EtOAc (20 ml) and washed with water (2×10 ml), a saturated aqueous solution of NaHCO₃ (10 ml) and brine (10 ml). The aqueous layers were extracted with EtOAc (20 ml). The organic layers were combined, dried (MgSO₄) and the solvent was removed under reduced pressure to give a yellow oil. After purification by crystallization in EtOAc/Et2O/pentane, the title compound (66) was obtained as a white powder (175 mg, 36%). HPLC, Rt: 4.0 min (purity: 100%). LC/MS, M⁺(ESI): 425.3, M⁻(ESI): 422.9.

Example 67

Formation of ethyl 2-[2-[(6,7-dimethoxy-3,4-dihydroisoquinolin-2(1H)-yl)sulfonyl]-1-[formyl(hydroxy)amino]ethyl]cyclopropanecarboxylate (67)

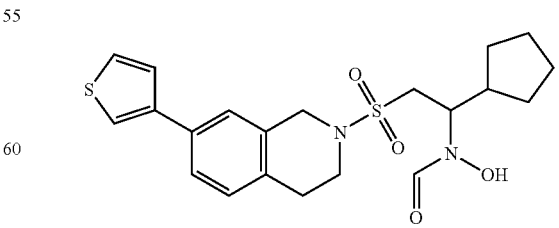

The title compound was prepared following procedure described in Example 19 step c), but starting from 6,7-dimethoxy-2-(methylsulfonyl)-1,2,3,4-tetrahydroisoquinoline and ethyl 2-formyl-1-cyclopropanecarboxylate. After purification by crystallization in Et₂O, the title compound (67) was obtained as a white powder. HPLC, Rt: 3.0 min (purity: 98.9%). LC/MS, M⁺(ESI): 457.4, M⁻(ESI): 455.1.

Example 68

Formation of N-(1-cyclopentyl-2-{[7-(3-thienyl)-3,4-dihydroisoquinolin-2(1H)-yl]sulfonyl}ethyl)-N-hydroxyformamide (68)

A mixture of N-{2-[(7-bromo-3,4-dihydroisoquinolin-2 (1H)-yl)sulfonyl]-1-yclopentylethyl}-N-hydroxyformamide (200 mg, 0.46 mmol), 3-thienylboronic acid (90 mg, 0.70 mmol) and potassium carbonate anhydrous (190 mg, 1.39 mmol) was prepared in MeOH (2 ml) and 1,4-dioxane (2 ml). Argon was bubbled for 5 min., then a suspension of Pd(OAc)$_2$ (5.2 mg, 0.02 mmol) and triphenylphosphine (6.1 mg, 0.02 mmol) in MeOH (2 ml) was added. The resulting mixture was heated at 80° C. under microwaves for 15 min. The reaction mixture was diluted with EtOAc and washed with water (2×). The organic layer was dried (MgSO$_4$) and the solvents were removed under reduced pressure. After purification by crystallization in EtOAc/pentane, the title compound (68) was obtained as a white powder (130 mg, 65%). HPLC, Rt: 4.4 min (purity: 99.3%). LC/MS, M$^+$(ESI): 435.3, M$^-$(ESI): 432.9.

Example 69

Formation of N-{1-cyclopentyl-2-[(7-phenyl-3,4-dihydroisoquinolin-2(1H)-yl)sulfonyl]ethyl}-N-hydroxyformamide (69)

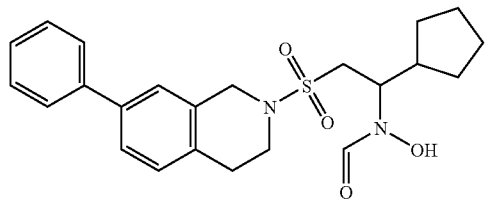

The title compound was prepared following procedure described in Example 68, but starting from phenylboronic acid. After purification by crystallization in EtOAc/pentane, the title compound (69) was obtained as a white powder (56 mg, 56%). HPLC, Rt: 4.5 min (purity: 98.0%). LC/MS, M$^+$(ESI): 429.3, M$^-$(ESI): 426.9.

Example 70

Formation of N-(1-cyclopentyl-2-{[7-(3-hydroxyphenyl)-3,4-dihydroisoquinolin-2(1H)-yl]sulfonyl}ethyl)-N-hydroxyformamide (70)

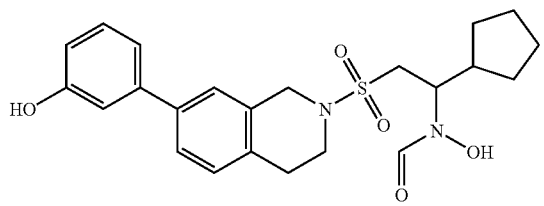

The title compound was prepared following procedure described in Example 68, but starting from 3-hydroxyphenylboronic acid. After purification by crystallization in EtOAc/pentane, the title compound (70) was obtained as a white powder (135 mg, 65%). HPLC, Rt: 3.8 min (purity: 95.8%). LC/MS, M$^+$(ESI): 445.4, M$^-$(ESI): 443.2.

Example 71

Formation of 2-[2-[(6,7-dimethoxy-3,4-dihydroisoquinolin-2(1H)-yl)-sulfonyl]-1-[formyl(hydroxy)amino]ethyl]cyclopropanecarboxylic acid (71)

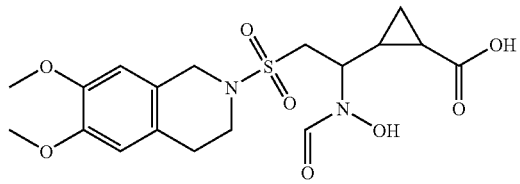

A solution of ethyl 2-{2-[(6,7-dimethoxy-3,4-dihydroisoquinolin-2(1H)-yl)sulfonyl]-1-[formyl(hydroxy)amino]ethyl}cyclopropanecarboxylate (192 mg, 0.42 mmol) was prepared in THF (5 ml) and water (2 ml), then LiOH (176 mg, 4.2 mmol) was added. The resulting mixture was stirred at RT for 3 hours. The reaction mixture was diluted with EtOAc, then washed a 1N aqueous solution of HCl and brine. The organic layer was dried (MgSO4) and the solvents were evaporated under reduced pressure. After purification by crystallization in DCM/Et2O, the title compound (71) was obtained as a white powder (100 mg, 55%). HPLC, Rt: 2.1 min (purity: 86.7%). LC/MS, M$^-$(ESI): 427.1.

Example 72

Formation of N-[1-cyclopropyl-2-(1,3-dihydro-2H-isoindol-2-ylsulfonyl)-ethyl]-N-hydroxyformamide (72)

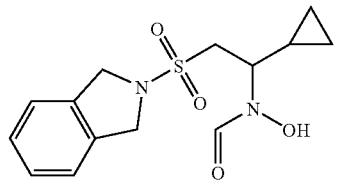

The title compound was prepared following procedure described in Example 40 step e), but starting from 2-(methylsulfonyl)isoindoline and cyclopropanecarboxaldehyde. After purification by crystallization in EtOAc/pentane, the title compound (72) was obtained as an off-white powder (181 mg, 53%). HPLC, Rt: 2.7 min (purity: 100%). LC/MS, M$^+$(ESI): 311.1, M$^-$(ESI): 309.1.

Example 73

Formation of N-{2-[(7-chloro-3,4-dihydroisoquinolin-2(1H)-yl)sulfonyl]-1-cyclopropylethyl}-N-hydroxyformamide (73)

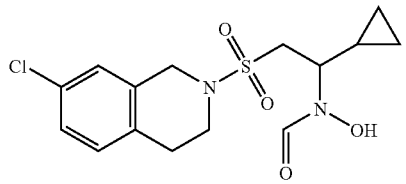

The title compound was prepared following procedure described in Example 40 step e), but starting from 7-chloro-2-(methylsulfonyl)-1,2,3,4-tetrahydroisoquinoline and cyclopropanecarboxaldehyde. After purification by crystallization in EtOAc/pentane, the title compound (73) was obtained as a white powder (246 mg, 62%). HPLC, Rt: 3.5 min (purity: 100%). LC/MS, M⁺(ESI): 359.2, M⁻(ESI): 357.0.

Example 74

Formation of N-(1-cyclopropyl-2-{[6-(trifluoromethyl)-3,4-dihydro-isoquinolin-2(1H)-yl]sulfonyl}ethyl)-N-hydroxyformamide (74)

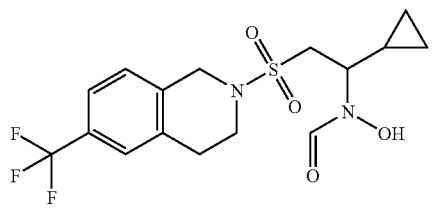

The title compound was prepared following procedure described in Example 40 step e), but starting from 2-(methylsulfonyl)-6-(trifluoromethyl)-1,2,3,4-tetrahydroisoquinoline and cyclopropanecarboxaldehyde. After purification by crystallization in Et₂O/pentane, the title compound (74) was obtained as an off-white powder (231 mg, 54%). HPLC, Rt: 3.8 min (purity: 96.4%). LC/MS, M⁺(ESI): 393.2, M⁻(ESI): 391.1.

Example 75

Formation of N-(1-cyclopropyl-2-{[7-(4-fluorophenyl)-3,4-dihydro-isoquinolin-2(1H)-yl]sulfonyl}ethyl)-N-hydroxyformamide (75)

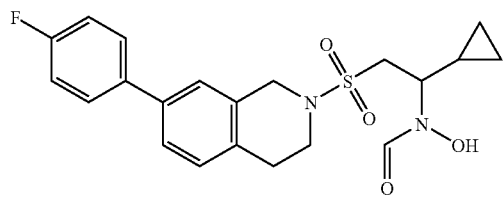

The title compound was prepared following procedure described in Example 40 step e), but starting from 7-(4-fluorophenyl)-2-(methylsulfonyl)-1,2,3,4-tetrahydroisoquinoline and cyclopropanecarboxaldehyde. After purification by crystallization in EtOAc, the title compound (75) was obtained as a white powder (278 mg, 60%). HPLC, Rt: 4.1 min (purity: 99.1%). LC/MS, M⁺(ESI): 419.3, M⁻(ESI): 416.9.

Example 76

Formation of N-(1-{[(7-chloro-3,4-dihydroisoquinolin-2(1H)-yl)-sulfonyl]methyl}-4,4,4-trifluorobutyl)-N-hydroxyformamide (76)

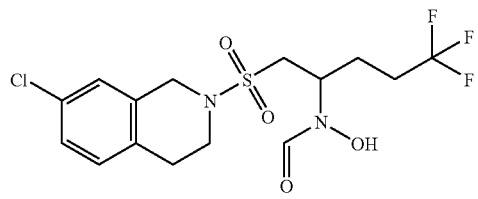

The title compound was prepared following procedure described in Example 40 step e), but starting from 7-chloro-2-(methylsulfonyl)-1,2,3,4-tetrahydroisoquinoline and 4,4,4-trifluorobutyraldehyde. After purification by crystallization in EtOAc/pentane, the title compound (76) was obtained as a white powder (420 mg, 45%). HPLC, Rt: 4.1 min (purity: 99.2%). LC/MS, M⁺(ESI): 415.1.

Example 77

Formation of N-{1-cyclopentyl-2-[(6,7-dichloro-3,4-dihydroisoquinolin-2(1H)-yl)sulfonyl]ethyl}-N-hydroxyformamide (77)

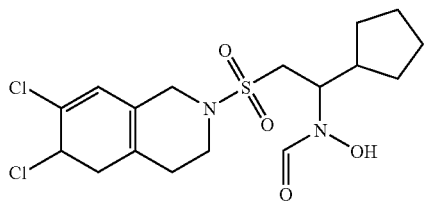

The title compound was prepared following procedure described in Example 40 step e), but starting from 6,7-dichloro-2-(methylsulfonyl)-1,2,3,4-tetrahydroisoquinoline and cyclopentanecarboxaldehyde. After purification by crystallization in MeOH, the title compound (77) was obtained as a white powder (245 mg, 42%). HPLC, Rt: 4.4 min (purity: 99.3%). LC/MS, M⁺(ESI): 421.2, M⁻(ESI): 418.9.

Example 78

Formation of N-{1-cyclopentyl-2-[(7-isopropoxy-3,4-dihydroisoquinolin-2(1H)-yl)sulfonyl]ethyl}-N-hydroxyformamide (78)

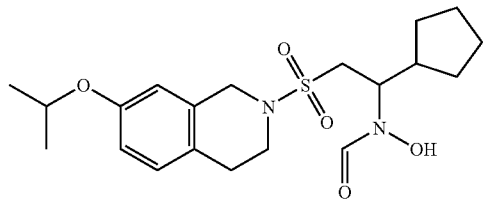

The title compound was prepared following procedure described in Example 40 step e), but starting from 7-isopropoxy-2-(methylsulfonyl)-1,2,3,4-tetrahydroisoquinoline and cyclopentanecarboxaldehyde. After purification by crystallization in EtOAc/pentane, the title compound (78) was obtained as a white powder (390 mg, 68%). HPLC, Rt: 4.2 min (purity: 99.6%). LC/MS, M⁺(ESI): 411.3, M⁻(ESI): 408.9.

Example 79

Formation of N-{1-cyclopentyl-2-[(7-pyridin-4-yl-3,4-dihydroisoquinolin-2(1H)-yl)sulfonyl]ethyl}-N-hydroxyformamide (79)

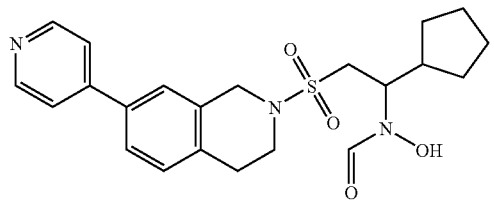

The title compound was prepared following procedure described in Example 68, but starting from pyridine-4-boronic acid. The reaction mixture was heated at 100° C. for 10 hours. After purification by crystallization in EtOAc, the title compound (79) was obtained as a white powder (95 mg, 48%). HPLC, Rt: 2.5 min (purity: 88.6%). LC/MS, M⁺(ESI): 430.3, M⁻(ESI): 428.0.

Example 80

Formation of N-{1-cyclopentyl-2-[(5-fluoro-1,3-dihydro-2H-isoindol-2-yl)sulfonyl]ethyl}-N-hydroxyformamide (80)

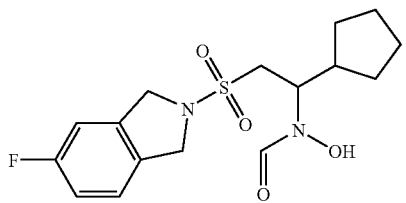

The title compound was prepared following procedure described in Example 40 step e), but starting from 5-fluoro-2-(methylsulfonyl)isoindoline and cyclopentanecarboxaldehyde. After purification by crystallization in EtOAc/pentane, the title compound (80) was obtained as a white powder. HPLC, Rt: 3.6 min (purity: 89.9%). LC/MS, M⁺(ESI): 357.1, M⁻(ESI): 355.1.

Example 81

Formation of N-{1-cyclopentyl-2-[(6-isopropyl-3,4-dihydroisoquinolin-2(1H)-yl)sulfonyl]ethyl}-N-hydroxyformamide (81)

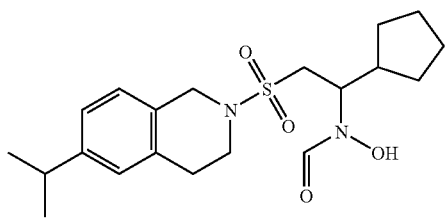

The title compound was prepared following procedure described in Example 40 step e), but starting from 6-isopropyl-2-(methylsulfonyl)-1,2,3,4-tetrahydroisoquinoline and cyclopentanecarboxaldehyde. After purification by crystallization in EtOAc/pentane, the title compound (81) was obtained as a white powder (121 mg, 37%). HPLC, Rt: 4.6 min (purity: 99.5%). LC/MS, M⁺(ESI): 395.2, M⁻(ESI): 393.3.

Example 82

Formation of N-(1-cyclopentyl-2-{[7-(trifluoromethyl)-3,4-dihydro-isoquinolin-2(1H)-yl]sulfonyl}ethyl)-N-hydroxyformamide (82)

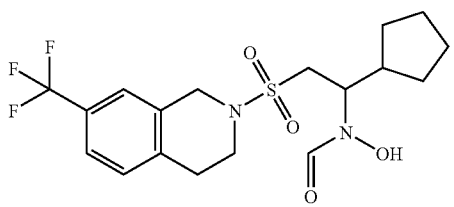

The title compound was prepared following procedure described in Example 40 step e), but starting from 2-(methylsulfonyl)-7-(trifluoromethyl)-1,2,3,4-tetrahydroisoquinoline and cyclopentanecarboxaldehyde. After purification by crystallization in EtOAc/pentane, the title compound (82) was obtained as a white powder (180 mg, 52%). HPLC, Rt: 4.4 min (purity: 100%). LC/MS, M⁺(ESI): 421.3, M⁻(ESI): 419.2.

Example 83

Formation of N-(1-cyclopropyl-2-{[7-(trifluoromethyl)-3,4-dihydroisoquinolin-2(1H)-yl]sulfonyl}ethyl)-N-hydroxyformamide (83)

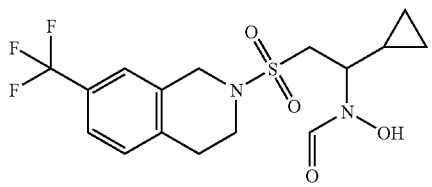

The title compound was prepared following procedure described in Example 40 step e), but starting from 2-(methylsulfonyl)-7-(trifluoromethyl)-1,2,3,4-tetrahydroisoquinoline and cyclopropanecarboxaldehyde. After purification by crystallization in EtOAc/pentane, the title compound (83) was obtained as a white powder (190 mg, 59%). HPLC, Rt: 3.8 min (purity: 97.8%). LC/MS, M⁺(ESI): 393.2, M⁻(ESI): 391.2.

Example 84

Formation of N-{1-cyclopropyl-2-[(6,7-dimethoxy-3,4-dihydro-isoquinolin-2(1H)-yl)sulfonyl]ethyl}-N-hydroxyformamide (84)

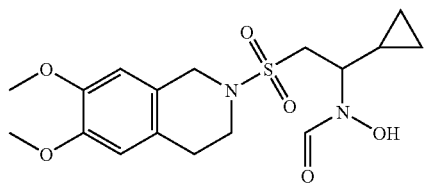

The title compound was prepared following procedure described in Example 40 step e), but starting from 6,7-dimethoxy-2-(methylsulfonyl)-1,2,3,4-tetrahydroisoquinoline and cyclopropanecarboxaldehyde. After purification by crystallization in EtOAc/pentane, the title compound (84) was obtained as a white powder (235 mg, 75%). HPLC, Rt: 2.6 min (purity: 99.3%). LC/MS, M⁺(ESI): 385.0, M⁻(ESI): 383.0.

Example 85

Formation of N-{1-cyclopropyl-2-[(6-isopropyl-3,4-dihydroisoquinolin-2(1H)-yl)sulfonyl]ethyl}-N-hydroxyformamide (85)

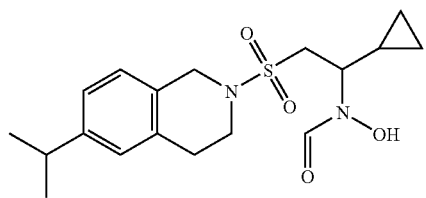

The title compound was prepared following procedure described in Example 40 step e), but starting from 6-isopropyl-2-(methylsulfonyl)-1,2,3,4-tetrahydroisoquinoline and cyclopropanecarboxaldehyde. After purification by crystallization in EtOAc/pentane, the title compound (85) was obtained as a white powder (160 mg, 53%). HPLC, Rt: 4.0 min (purity: 100%). LC/MS, M+(ESI): 367.3, M−(ESI): 365.2.

Example 86

Formation of N-(1-{[(7-chloro-3,4-dihydroisoquinolin-2(1H)-yl)sulfonyl]methyl}-3-pyridin-3-ylpropyl)-N-hydroxyformamide (61)

Step a) Formation of 1-[(7-chloro-3,4-dihydroisoquinolin-2(1H)-yl)sulfonyl]-4-pyridin-3-ylbutan-2-ol

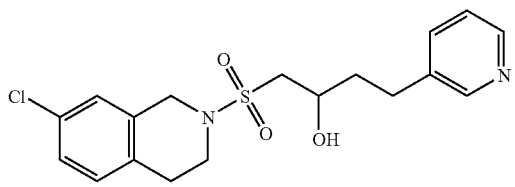

A solution of 7-chloro-2-(methylsulfonyl)-1,2,3,4-tetrahydroisoquinoline (400 mg, 1.63 mmol) was prepared in anhydrous THF (8 ml) and cooled at −78° C. Then a solution of LiHMDS (1M in THF, 3.6 ml, 3.6 mmol) was added dropwise. After 5 min., methyl 3-(3-pyridyl)propionate (295 mg, 1.79 mmol) was added. The resulting mixture was stirred at −78° C. for 5 min., then at RT for 1 hour. The reaction mixture was evaporated under reduced pressure. The residue was taken up with THF (8 ml) and a solution of HCl (1.25M in MeOH, 5.8 ml, 7.2 mmol) was added, followed by sodium borohydride (92 mg, 2.44 mmol). The resulting mixture was stirred at RT for 1 hour. The reaction mixture was diluted with EtOAc and washed with water (2×) and brine. The organic layer was dried (MgSO4) and the solvents were removed under reduced pressure to give the crude title compound as an oil (557 mg, 90%) used in the next step without further purification. HPLC, Rt: 2.7 min (purity: 69%). LC/MS, M+(ESI): 381.2.

Step b) Formation of a mixture of 7-chloro-2-[(4-pyridin-3-ylbut-1-en-1-yl)sulfonyl]-1,2,3,4-tetrahydroisoquinoline

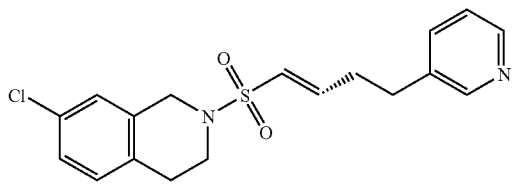

A solution of 1-[(7-chloro-3,4-dihydroisoquinolin-2(1H)-yl)sulfonyl]-4-pyridin-3-ylbutan-2-ol (270 mg of crude compound) and Et3N (0.23 ml, 1.69 mmol) in anhydrous THF (3 ml) was cooled at 0° C., then methanesulfonyl chloride (0.066 ml, 0.85 mmol) was added dropwise. The resulting mixture was stirred at 0° C. for 1 hour, then at 60° C. for 15 hours. The reaction mixture was diluted with DCM, then washed with a saturated aqueous solution of NaHCO3 and brine. The organic layer was dried (MgSO4) and the solvents were removed under reduced pressure to give the title compound as an oil (300 mg) used in the next step without further purification. HPLC, Rt: 3.1 min (purity: 63%). LC/MS, M+(ESI): 363.2, M−(ESI): 361.1.

Step c) Formation of N-(1-{[(7-chloro-3,4-dihydroisoquinolin-2(1H)-yl)sulfonyl]methyl}-3-pyridin-3-ylpropyl)-N-hydroxyformamide

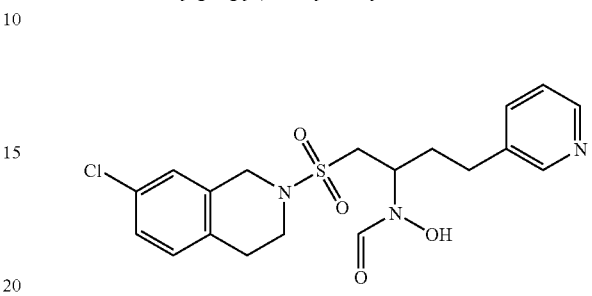

The title compound was prepared following procedure described in Example 61 step d), but starting from 7-chloro-2-[(4-pyridin-3-ylbut-1-en-1-yl)sulfonyl]-1,2,3,4-tetrahydroisoquinoline (300 mg of the crude mixture). After purification by preparative HPLC (column Waters Xterra, gradient water/ACN), the title compound (86) was obtained as a white powder (156 mg, 45% overall yield). HPLC, Rt: 2.6 min (purity: 97.4%). LC/MS, M+(ESI): 424.2.

Biological Assays:

The compounds of the present invention may be subjected to the following assays:

Example 87

Enzyme Inhibition Assays

Compounds of the invention were tested to assess their activities as inhibitors of MMP-1, MMP-2, MMP-9, MMP-14, MMP-12 and TACE. MMP-9 Assay Protocol Compounds of the invention were tested for inhibitory activity against 92 kDa gelatinase (MMP-9) in an assay using a coumarin-labeled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (McaPLGLDpaAR) (Knight et al, *FEBS Lett.* 1992; 263-266).

Stock solutions were made up as follows: Assay Butter: 100 mM Tris-HCl pH 7.6 containing 100 mM NaCl, 10 mM CaCl2, and 0.05% Brij 35.

Substrate: 0.4 mM McaPLGLDpaAR (from Bachem) (0.437 mg/ml) stock solution in 100% DMSO (stored at −20° C.). Dilute to 8 µM in assay butter.

Enzyme: Recombinant human 92 kDa gelatinase (MMP-9; APMA (4-aminophenyl mercuric acetate)-activated if necessary) appropriately diluted in assay butter.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 µM (column 1) to 5.1 nM (column 10).

The assay was performed in a total volume of 100 µL per well in 96-well microtitre plates. Activated enzyme (20 µL) was added to the wells followed by 20 µL of assay butter. Appropriate concentrations of test compounds dissolved in 10 µL of DMSO were then added followed by 50 µL of McaPLGLDpaAR (8 µM, prepared by dilution of DMSO stock in assay butter). For each as say ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SL T Labinstruments GmbH, Grödig, Austria) using 320 nm excitation, without stopping the reaction.

The effect of the test compound was determined from the dose response curve generated by the 10 duplicate concentrations of inhibitor. The $IC_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the $IC_{50}$; d=is the slope). The result was rounded to one significant figure.

MMP-12 Assay Protocol

Compounds of the invention were tested for inhibitory activity against metalloelastase (MMP-12) in an assay using a coumarin-labelled peptide substrate, (7-methoxycoumarin-4-yl)acetyl-Pro-Leu-Gly-Leu-(3-[2,4-dinitrophenyl]-L-2,3-diaminopropionyl)-Ala-Arg-NH2 (McaPLGLDpaAR) (Knight et al, 1992, above). The protocol for this assay was as described for the MMP-9 assay above.

MMP-1 Assay protocol

Compounds of the invention were tested for inhibitory activity against collagenase (MMP-1) in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLDpaAR) (Knight et al, 1992, above). The protocol for this assay was as described for the MMP-9 assay above.

MMP-14 Assay Protocol

Compounds of the invention were tested for inhibitory activity against MMP-14 in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLD paAR) (Knight et al, 1992, above). The protocol for this assay was as described for the MMP-9 assay above.

MMP-2 Assay Protocol

Compounds of the invention were tested for inhibitory activity against gelatinase A (MMP-2) in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLDpaAR) (Knight et al, 1992, above). The protocol for this assay was as described for the MMP-9 assay above.

TACE Assay Protocol

Compounds of the invention can be tested for inhibitory activity against human ADAM17 in an assay using human Mca-(endo-1a-Dap(Dnp)-TNF-alpha(−5 to +6)amide as substrate (FEBS Letters, 2000, 275-279).

Stock solutions are prepared as followed:
Assay Buffer: 20 mM Hepes pH 7.5 (Fluka) containing 0.05% Brij 35 (Fluka)
Substrate: 6.1 mM human Mca-(endo-1a-Dap(Dnp)-TNF-alpha(−5 to +6)amide (Bachem) stock solution in 100% DMSO (stored at −20° C.); diluted to 5 µM in assay buffer.
Enzyme: Recombinant human ADAM17, appropriately diluted in assay buffer (1.5 µg/ml).

Test Compounds are prepared initially as 10 mM compound solution in 100% DMSO, diluted to 1 mM in 100% DMSO, then serially diluted 3-fold in 100% DMSO across a 96-well microtitre plate. Assay concentration range is typically between 100 µM to 0.01 nM. The assay is performed in a total volume of 100 µL per well in 96-well microtitre plates. Appropriate concentrations of test compounds dissolved in 10 µL of DMSO are added to the wells, followed by substrate solution (50 µL, 5 µM prepared by dilution of DMSO stock in assay buffer) and enzyme solution (40 µL). For each as say ten concentrations of test compound are examined in triplicate. Control wells lack either enzyme or test compound. The reactions are incubated at room temperature for 1.5 hours. The fluorescence at 405 nm is measured immediately with a fluorometer using 355 nm excitation, without stopping the reaction.

The effect of the test compound is determined from the dose response curve generated by the 10 duplicate concentrations of inhibitor. The $IC_{50}$ (the concentration of compound required to give a 50% decrease in enzyme activity) is obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the $IC_{50}$; d=is the slope). The result is rounded to one significant figure.

The results are expressed in terms of $IC_{50}$ (the concentration of compound required to give a 50% decrease in enzyme activity) and are presented in Table 1 below.

The results are expressed in terms of $IC_{50}$ (the concentration of compound required to give a 50% decrease in enzyme activity) and are presented in Table 1 below.

TABLE 1

$IC_{50}$ on different MMPs:

| | IC50 (nM) or percentage inhibition | | | | | | |
|---|---|---|---|---|---|---|---|
| Example. | MMP1 | MMP2 | MMP9 | MMP12 | MMP13 | MMP14 | Tace |
| 1 | >5000 | 95 | >5000 | 27 | 97% @ 5 µM, 15% @ 0.1 µM | >5000 | 67 |
| 2 | >5000 | 530 | >5000 | 14 | 98% @ 5 µM, 17% @ 0.1 µM | >5000 | 33 |
| 3 | 31% @ 5 µM | 676 | >5000 | 14 | 98% @ 5 µM, 6% @ 0.1 µM | 67% @ 5 µM | 28 |
| 4 | 19% @ 5 µM | 653 | >5000 | 65 | 80% @ 5 µM, 0% @ 0.1 µM | 29% @ 5 µM | 114 |
| 5 | 32% @ 5 µM | 759 | >5000 | 16 | 97% @ 5 µM, 16% @ 0.1 µM | 70% @ 5 µM | |
| 6 | >5000 | 323 | 877 | 9 | 94% @ 5 µM, 11% @ 0.1 µM | 865 | 280 |

TABLE 1-continued

IC$_{50}$ on different MMPs:

IC50 (nM) or percentage inhibition

| Example. | MMP1 | MMP2 | MMP9 | MMP12 | MMP13 | MMP14 | Tace |
|---|---|---|---|---|---|---|---|
| 7 | 31% @ 5 μM | 784 | >5000 | 18 | | 71% @ 5 μM | |
| 8 | 5% @ 5 μM | >5000 | >5000 | 627 | 41% @ 5 μM | 8% @ 5 μM | |
| 9 | 29% @ 5 μM | >5000 | >5000 | 49 | | 61% @ 5 μM | 128 |
| 10 | 8% @ 5 μM | >5000 | >5000 | 13 | 93% @ 5 μM, 15% @ 0.1 μM | 36% @ 5 μM | 67 |
| 11 | | | >5000 | 26 | | | |
| 12 | 0% @ 5 μM | >5000 | >5000 | 92 | 48% @ 5 μM | 0% @ 5 μM | 1220 |
| 13 | 16% @ 5 μM | >5000 | >5000 | 10 | 96% @ 5 μM, 28% @ 0.1 μM | 64% @ 5 μM | 40 |
| 14 | 0% @ 5 μM | >5000 | >5000 | 41 | 68% @ 5 μM, 5% @ 0.1 μM | 0% @ 5 μM | 620 |
| 15 | 0% @ 5 μM | >5000 | >5000 | 185 | | 0% @ 5 μM | |
| 16 | 74% @ 5 μM, 5% @ 0.1 μM | 78 | >5000 | 12 | | 80% @ 5 μM, 0% @ 0.1 μM | 311 |
| 17 | 0% @ 5 μM | >5000 | | 103 | | 0% @ 5 μM | |
| 18 | 9% @ 5 μM | 5 | >5000 | 1.4 | | 95% @ 5 μM, 13% @ 0.1 μM | 640 |
| 19 | 45% @ 5 μM | 10 | >5000 | 6 | | 81% @ 5 μM, 10% @ 0.1 μM | 23 |
| 20 | 0% @ 5 μM | >5000 | >5000 | 280 | | 0% @ 5 μM | |
| 21 | 20% @ 5 μM | 103 | >5000 | 19 | | 45% @ 5 μM | 56 |
| 22 | 0% @ 5 μM | 470 | >5000 | 210 | | 0% @ 5 μM | 389 |
| 23 | 52% @ 5 μM | 27 | >5000 | 28 | | 72% @ 5 μM, 7% @ 0.1 μM | 13 |
| 24 | 0% @ 5 μM | >5000 | >5000 | 300 | | 0% @ 5 μM | >5000 |
| 25 | 37% @ 5 μM | 78 | >5000 | 6.0 | | 73% @ 5 μM, 0% @ 0.1 μM | 1195 |
| 26 | 92% @ 5 μM, 17% @ 0.1 μM | 60 | 62% @ 5 μM | 10 | | 82% @ 5 μM | 1098 |
| 27 | 30% @ 5 μM | 58 | 13% @ 5 μM | 6.9 | | 41% @ 5 μM | 506 |
| 28 | 18% @ 5 μM | 45 | 21% @ 5 μM | 3.9 | | 62% @ 5 μM | 1284 |
| 29 | 94% @ 5 μM, 22% @ 0.1 μM | 150 | 40% @ 5 μM | 14 | | 78% @ 5 μM | 277 |
| 30 | 8% @ 5 μM | 880 | 3% @ 5 μM | 32 | | 38% @ 5 μM | >5000 |
| 31 | 10% @ 5 μM | 939 | 3% @ 5 μM | 40 | | 19% @ 5 μM | >5000 |
| 32 | 4% @ 5 μM | >5000 | 4% @ 5 μM | 168 | | 14% @ 5 μM | >5000 |
| 33 | 4% @ 5 μM | 151 | 15% @ 5 μM | 27 | | 30% @ 5 μM | 427 |
| 34 | 12% @ 5 μM | 35 | 42% @ 5 μM | 6.0 | | 82% @ 5 μM, 3% @ 0.1 μM | 353 |
| 35 | 6% @ 5 μM | 62 | 43% @ 5 μM | 4.2 | | 85% @ 5 μM, 7% @ 0.1 μM | >5000 |
| 36 | 41% @ 5 μM | 41 | 37% @ 5 μM | 5.7 | | 75% @ 5 μM, 3% @ 0.1 μM | 228 |
| 37 | 36% @ 5 μM | 35 | 58% @ 5 μM | 4.2 | | 83% @ 5 μM, 8% @ 0.1 μM | 1090 |
| 38 | 17% @ 5 μM | 71 | 50% @ 5 μM | 7.2 | | 49% @ 5 μM | 276 |
| 39 | 25% @ 5 μM | 16 | 47% @ 5 μM | 4.1 | | 87% @ 5 μM, 10% @ 0.1 μM | 171 |
| 40 | 2% @ 5 μM | 77 | 11% @ 5 μM | 15 | | 54% @ 5 μM | 1122 |
| 41 | 54% @ 5 μM | 87 | 14% @ 5 μM | 11 | | 74% @ 5 μM, 5% @ 0.1 μM | 189 |
| 42 | 29% @ 5 μM | 31 | 35% @ 5 μM | 4.4 | | 88% @ 5 μM, 15% @ 0.1 μM | 611 |
| 43 | 53% @ 5 μM | 21 | 68% @ 5 μM, 1% @ 0.1 μM | 3.2 | | 89% @ 5 μM, 14% @ 0.1 μM | >5000 |
| 44 | 9% @ 5 μM | 91 | 21% @ 5 μM | 7.0 | | 83% @ 5 μM, 5% @ 0.1 μM | 371 |
| 45 | 2% @ 5 μM | 25 | 47% @ 5 μM | 1.5 | | 92% @ 5 μM, 19% @ 0.1 μM | 813 |
| 46 | | 5000 | | 460 | | | |
| 47 | 40% @ 5 μM | 33 | 40% @ 5 μM | 2.5 | | 79% @ 5 μM, 7% @ 0.1 μM | 933 |
| 48 | 26% @ 5 μM | 77 | 8% @ 5 μM | 46 | | 41% @ 5 μM | 269 |
| 49 | 29% @ 5 μM | 11 | 43% @ 5 μM | 5.5 | | 86% @ 5 μM, 14% @ 0.1 μM | 239 |
| 50 | 0% @ 5 μM | 90 | 72% @ 5 μM, 4% @ 0.1 μM | 3.5 | | 83% @ 5 μM, 13% @ 0.1 μM | 397 |
| 51 | | 1330 | | 109 | | | |
| 52 | 14% @ 5 μM | 298 | 10% @ 5 μM | 46 | | 49% @ 5 μM | 92 |
| 53 | 16% @ 5 μM | 298 | 5% @ 5 μM | 106 | | 34% @ 5 μM | 245 |
| 54 | | >5000 | | 234 | | | |
| 55 | 69% @ 5 μM, 7% @ 0.1 μM | 24 | 39% @ 5 μM | 6 | | 86% @ 5 μM, 19% @ 0.1 μM | 157 |
| 56 | 34% @ 5 μM | 190 | 2% @ 5 μM | 51 | | 48% @ 5 μM | >5000 |
| 57 | 0% @ 5 μM | >5000 | 0% @ 5 μM | 117 | | 0% @ 5 μM | >5000 |

TABLE 1-continued

IC$_{50}$ on different MMPs:

IC50 (nM) or percentage inhibition

| Example. | MMP1 | MMP2 | MMP9 | MMP12 | MMP13 | MMP14 | Tace |
|---|---|---|---|---|---|---|---|
| 58 | 68% @ 5 μM, 4% @ 0.1 μM | 20 | 41% @ 5 μM | 4.5 | | 79% @ 5 μM, 11% @ 0.1 μM | 56 |
| 59 | 35% @ 5 μM | 83 | 32% @ 5 μM | 7.5 | | 43% @ 5 μM | >5000 |
| 60 | 6% @ 5 μM | 411 | 0% @ 5 μM | 69 | | 16% @ 5 μM | 79 |
| 61 | 22% @ 5 μM | 38 | 12% @ 5 μM | 15 | | 43% @ 5 μM | 89 |
| 62 | 52% @ 5 μM | 293 | 1% @ 5 μM | 36 | | 75% @ 5 μM | 882 |
| 63 | 34% @ 5 μM | >5000 | 7% @ 5 μM | 88 | | 9% @ 5 μM | >5000 |
| 64 | 36% @ 5 μM | 42 | 32% @ 5 μM | 7.9 | | 71% @ 5 μM | 91 |
| 65 | 30% @ 5 μM | 277 | 13% @ 5 μM | 27 | | 50% @ 5 μM | 490 |
| 66 | | >5000 | | 209 | | | |
| 67 | | >5000 | | 111 | | | |
| 68 | 0% @ 5 μM | 221 | 31% @ 5 μM | 9 | | 99% @ 5 μM, −30% @ 0.1 μM | 268 |
| 69 | 4% @ 5 μM | 527 | 26% @ 5 μM | 18 | | 63% @ 5 μM | 606 |
| 70 | 0% @ 5 μM | 1562 | 3% @ 5 μM | 41 | | 27% @ 5 μM | >5000 |
| 71 | | >5000 | | 585 | | | |
| 72 | 75% @ 5 μM | 510 | 28% @ 5 μM | 20 | | 63% @ 5 μM | 683 |
| 73 | 19% @ 5 μM | 187 | 5% @ 5 μM | 45 | | 40% @ 5 μM | 88 |
| 74 | 44% @ 5 μM | 97 | 32% @ 5 μM | 5.2 | | 76% @ 5 μM | >5000 |
| 75 | 0% @ 5 μM | 219 | 71% @ 5 μM | 6 | | 92% @ 5 μM, 11% @ 0.1 μM | 394 |
| 76 | 43% @ 5 μM | 82 | 14% @ 5 μM | 22 | | 59% @ 5 μM | 115 |
| 77 | 17% @ 5 μM | 31 | 35% @ 5 μM | 5.1 | | 78% @ 5 μM | 229 |
| 78 | | >5000 | | 322 | | | |
| 79 | 0% @ 5 μM | 67 | 57% @ 5 μM | 2 | | 72% @ 5 μM, 19% @ 0.1 μM | 587 |
| 80 | 25% @ 5 μM | 474 | 0% @ 5 μM | 45 | | 15% @ 5 μM | >5000 |
| 81 | 3% @ 5 μM | 63 | 44% @ 5 μM | 3.1 | | 87% @ 5 μM, 0% @ 0.1 μM | >5000 |
| 82 | 10% @ 5 μM | 348 | 0% @ 5 μM | 26 | | 20% @ 5 μM | >5000 |
| 83 | 4% @ 5 μM | 686 | 4% @ 5 μM | 52 | | 6% @ 5 μM | >5000 |
| 84 | | >5000 | | 366 | | | |
| 85 | 5% @ 5 μM | 78 | 28% @ 5 μM | 4.9 | | 95% @ 5 μM, 14% @ 0.1 μM | >5000 |
| 86 | 49% @ 5 μM | 21 | 52% @ 5 μM | 9.8 | | 100% @ 5 μM, 12% @ 0.1 μM | 59 |

Example 88

IL-2-Induced Peritoneal Recruitment of Lymphocytes

Administration of IL-2 intraperitoneally causes migration of lymphocytes into the intraperitoneal cavity. This is a model for the cellular migration that occurs during inflammation.

Protocol

C3H/HEN mice (Elevage Janvier, France) were intraperitoneally injected with IL-2 (Serono Pharmaceutical Research Institute, 20 μg/kg, in saline). Compounds of the invention were suspended in 0.5% carboxymethylcellulose (CMC)/0.25% tween-20 and were administered by s.c. or p.o. route (10 ml/kg) 15 min prior to administration of IL-2.

Twenty-four hours after administration of IL-2, peritoneal white blood cells were collected by 3 successive lavages of the peritoneal cavity with 5 ml phosphate buffered saline (PBS)-1 mM EDTA (+4° C.). The suspension was centrifuged (1700 g×10 min at +4° C.). The resulting pellet was suspended in 1 ml PBS-1 mM EDTA.

Lymphocytes were identified and counted using a Beckman/Coulter counter.

Experimental Design

The animals were divided into 6 groups (6 mice each group):

Group 1: (baseline) received 0.5% CMC/0.25% tween-20 (vehicle of compound of the invention) and saline (vehicle of IL-2);

Group 2: (control IL-2) received 0.5% CMC/0.25% tween-20 and injection of IL-2;

Group 3: Experimental group (Compound of the invention Dose 1) received a compound of the invention and injection of IL-2;

Group 4: Experimental group (Compound of the invention Dose 2) received a compound of the invention and injection of IL-2;

Group 5: Experimental group (Compound of the invention Dose 3) received a compound of the invention and injection of IL-2;

Group 6: Reference group received reference compound dexamethasone and injection of IL-2.

Calculation

Inhibition of lymphocyte recruitment was calculated as follows:

$$\% \text{ inhibition} = \frac{1 - (LyX - Ly1)}{(Ly2 - Ly1)} \times 100\%$$

Where Ly 1=Number of lymphocytes in group 1 (E3/μl), Ly 2=Number of lymphocytes in group 2 (E3/μl), Ly X=Number of lymphocytes in group X (3-5) (E3/μl).

The results for compounds according to Formula (I) are presented in Table 2 below.

TABLE 2

Percentage of inhibition of IL-2-induced peritoneal recruitment of lymphocytes by compounds of the invention:

| Example | Dose (mg/kg) | Route | % inhibition |
|---|---|---|---|
| 2 | 3 | p.o. | 16 ± 13 |
| 6 | 3 | p.o. | 40 ± 6 |
| 14 | 3 | p.o. | 50 ± 10 |
| 16 | 3 | p.o. | 44 ± 7 |
| 18 | 3 | p.o. | 39 ± 7 |
| 19 | 3 | p.o. | 62 ± 9 |
| 21 | 3 | p.o. | 43 ± 9 |
| 25 | 3 | p.o. | 37 ± 7 |
| 27 | 3 | p.o. | 46 ± 9 |
| 28 | 3 | p.o. | 62 ± 5 |
| 29 | 3 | p.o. | 29 ± 11 |
| 31 | 3 | p.o. | 31 ± 10 |
| 35 | 3 | p.o. | 50 ± 8 |
| 42 | 3 | p.o. | 40 ± 10 |
| 49 | 3 | p.o. | 16 ± 12 |
| 50 | 3 | p.o. | 32 ± 4 |
| 56 | 3 | p.o. | 37 ± 8 |
| 59 | 3 | p.o. | 55 ± 9 |
| 61 | 3 | p.o. | 45 ± 9 |
| 62 | 3 | p.o. | 20 ± 9 |
| 68 | 3 | p.o. | 33 ± 7 |
| 72 | 3 | p.o. | 41 ± 7 |
| 75 | 3 | p.o. | 26 ± 11 |
| 76 | 3 | p.o. | 45 ± 11 |
| 79 | 3 | p.o. | 43 ± 10 |

Example 89

$CCl_4$-Induced Liver Fibrosis Model

Carbon tetrachloride ($CCl_4$) induces liver fibrosis when administered intraperitoneally (Bulbena O, Culat J, Bravo M L., *Inflammation* 1997 October; 21(5):475-88). Compounds of the invention can be evaluated for their ability to prevent the $CCl_4$-induced formation of fibrotic tissue.

Animals

Male Sprague-Dawley rats, 7 weeks old, weight approx. 300 g from Charles River/Iffa-Crédo, St-Germain/l'Arbresle, France.

Rats are acclimatised for 5 days before commencing experiments, in air-conditioned rooms, 2 animals per cage, Temperature: 22° C.±2, Relative humidity: 55%±10 Light: 12 hour cycle (7 a.m.-7 p.m.), Cage: Makrolon® cage 42.5× 26.6×15 on each fitted with a stainless steel cover-feed rack.

The study involves the following groups of 8 animals each, as indicated below.

Group 1: "Sham" animals receive $CCl_4$ vehicle (i.p.) and once daily, the vehicle of test substance (s.c.)

Group 2: Positive control group receives $CCl_4$ (i.p.), and once daily, the vehicle of the test substance (s.c.)

Group 3: Experimental group receives $CCl_4$ (i.p.), and once daily, 2 mg/kg s.c. of compound according to the invention.

Group 4: Experimental group receives $CCl_4$ (i.p.), and once daily, 10 mg/kg s.c. of the compound according to the invention.

Group 5: Experimental group receives $CCl_4$ (i.p.), and once daily, 20 mg/kg s.c. of the compound according to the invention.

Rats were labeled on their tails. The labels are checked and renewed, if necessary, after every $CCl_4$ injection.

Procedure $CCl_4$ (Prolabo) in olive oil is administered every 3 days for three weeks by intra-peritoneal injection (0.25 ml $CCl_4$/kg body weight, diluted in oil 1:1 vol:vol for a total volume of 0.5 ml/kg). Animals are weighed daily. If body weight decreased by more than 10% of the initial weight, the animal is excluded from the study.

Vehicles and compound are used as follows:

$CCl_4$ was administered in olive oil (Prolabo) at a 1:1 dilution;

The compound of the invention is suspended in 0.25% Tween-80 and 0.25% carboxymethylcellulose in sterile 0.9% NaCl. The solution is kept at 4° C. throughout the experiment and used each day to prepare the suspensions.

The compound of the invention is administered daily by subcutaneous (s.c.) injection at a volume of administration of 5 ml/kg. Groups 1 and 2 are dosed s.c. with 5 ml/kg of vehicle. Freshly prepared solutions are used on each day of the experiment. Administrations are carried out each day at the same time.

The treatment of groups of this study is started for each animal at the time of the first $CCl_4$ administration and is continued for 21 consecutive days. The last administration of test substances or vehicle is done 1 day before the sacrifice of the animals.

Results

Death are Reported, Date and Supposed Cause are Reported.

Serum Enzyme Levels

Animals are killed 21 days following the first $CCl_4$ administration by isofurane inhalation. Blood is withdrawn individually at the time of sacrifice, i.e. one day after the last administration of test substance or vehicle. Blood is centrifuged at 4° C. Plasma is carefully collected and aliquoted in 3 fractions. Plasma aspartate amino transferase (ASAT) and alanine amino transferase (ALAT) levels are measured in order to assess liver necrosis. Increased ASAT and ALAT levels in serum are associated with liver impairment. Average ASAT and ALAT levels for control animals and those treated with the compound of the invention at three different dosages are reported.

Histological Evaluation of Liver Fibrosis

Liver fibrosis is evaluated by measuring the area of fibrosis in the liver using microchotomy. Results are reported as percentage area that is fibrotic.

The liver is removed, the three lobes are dissected and samples are removed and either fixed in 10% formaldehyde or frozen at −80° C.

Liver sections are embedded in paraffin blocks. Sectioning and staining with Sirius red are performed. Quantification of the fibrosis in liver is carried out on a minimum of 3 sections taken from different locations in the liver. The quantitative analysis is performed using an image analyser (Imstar) and the software Morphostar.

Average area percentages of fibrosis in the livers of animals in the different groups are calculated.

Example 90

Chronic Obstructive Pulmonary Disease (COPD) Model

Compounds of the invention can be evaluated for their ability to prevent cigarette smoke-induced COPD.

Female AJ mice (Harlan, 17-25 g) are exposed daily to cigarette smoke (CS) for 11 consecutive days in groups of 5, in individual clear chambers. Animals are weighed prior to treatment, on day 6 of exposure and on day 12. The CS was generated using 1R1 cigarettes purchased from the Institute of Tobacco Research, University of Kentucky, USA and is allowed to enter the chambers at a flow rate of 100 ml/min.

In order to minimise any potential problems caused by repeated exposure to a high level of daily CS, the exposure of the mice to TS is increased gradually over the time to a maximum of 6 cigarettes from day 5 to day 11 (approximately 48 min exposure).

A sham group of mice is also exposed to air on a daily basis for equivalent lengths of time as controls (no CS exposure).

Treatment

Compounds of the invention are prepared in 0.5% carboxymethylcellulose Na salt (CMC, Sigma reference C-4888) as vehicle.

Animals are orally dosed twice daily by gavage in a dose volume of 5 ml/kg, 1 h prior to air or CS exposure and 6 h after the cessation of the exposure.

Sham animals (n=10) received vehicle and are exposed to air for up to a maximum of 50 minutes per day. The control group (n=10) received vehicle and is exposed to CS (up to a maximum of 6 cigarettes per day). Additional groups are exposed to CS (from up to a maximum of 6 cigarettes per day) and treated with one of the test compounds or the reference compound.

Bronchoalveolar Lavage and Cytospin Analysis

Twenty-four hours after the last CS exposure, bronchoalveolar lavage is performed as follows:

The trachea is dissected under deep anesthesia (sodium pentobarbitone) and cannulated using a Portex nylon intravenous cannula shortened to approximately 8 mm. Phosphate buffered saline (PBS, Gibco) containing 10 units/ml heparin (0.4 ml) is gently instilled and withdrawn 3 times. The lavage fluid is placed in an Eppendorf tube and kept on ice prior to subsequent determinations. Then, lavage fluid is separated from cells by centrifugation. The supernatant is removed and frozen for subsequent analysis. The cell pellet is resuspended in PBS and total cell numbers are calculated by counting a stained aliquot (Turks stain) under a microscope using a haemocytometer.

Differential cell count is then performed as follows: The residual cell pellet is diluted to approximately 105 cells per ml. A volume of 500 µl is placed in the funnel of a cytospin slide and is centrifuged for 8 min at 800 rpm. The slide is air-dried and stained using 'Kwik-Diff' solutions (Shandon) following purchaser instructions. Slides are dried and coverslipped and differential cell count is done using light microscopy. Up to 400 cells are counted for each slide. Cells were differentiated using standard morphometric techniques.

Statistical Analysis

The mean+/−S.D. is calculated for each experimental group.

Results are analyzed using a one-way analysis of variance (ANOVA), followed by a Bonferroni correction for multiple comparisons. Statistical significance is considered with $p<0.05$.

Example 91

Experimental Allergic Encephalomyelitis (EAE) Model

Compounds according to the invention can be evaluated for their activity in a model for multiple sclerosis in mice.

Animals

C57BL/6NCrlBR female mice are used. Mice are kept in wire cages (cm 32×14×13 h) with stainless steel feeders and fed on a standard diet (4RF21, Charles River, Italy) and water ad libitum. From day 7, wet pellets are also placed every day on the bottom of the cage. Plastic bottles are used in addition to the automatic water system.

Experimental Procedure

Mice are immunized (day=0) by injecting s.c. in the left flank 0.2 ml of an emulsion composed of 200 µg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they receive an i.p. injection of 500 ng pertussis toxin (List Biological Lab., Campbell, Calif., U.S.A.) dissolved in 400 µL of buffer (0.5 M NaCl, 0.017% Triton X-100, 0.015 M Tris, pH=7.5). On day 2, the animals are given a second injection of 500 ng pertussis toxin.

On day 7, the mice receive a second dose of 200 µg of $MOG_{35-55}$ peptide in CFA injected s.c. in the right flank. Starting approximately from day 8-10, this procedure results in a progressing paralysis, arising from the tail and ascending up to the forelimbs.

Animals are individually weighed and are examined for the presence of paralysis that is scored according to the following score-system (1):

0=no signs of disease 0.5=partial tail paralysis

1=tail paralysis 1.5=tail paralysis+partial unilateral hindlimb paralysis

2=tail paralysis+bilateral hindlimb weakness or partial paralysis 2.5=tail paralysis+partial hindlimb paralysis (lowered pelvi)

3=tail paralysis+complete hindlimb paralysis 3.5=tail paralysis+hindlimb paralysis+incontinence 4=tail paralysis+hindlimb paralysis+weakness or partial paralysis of forelimbs 5=moribund or dead Mortality and clinical signs are monitored daily in each group of treatment, by a technician who is unaware of treatments.

Daily treatment with compounds, their vehicle or with a reference compound starts on day 7 and continued for 15 or 21 consecutive days in all groups.

Histopathological Examination

At the end of the treatment period, each animal is anesthetised with sodium pentobarbital and is transcardially perfused-fixed with 4% paraformaldehyde via the left ventricle. Fixed spinal cords are then carefully dissected out.

Spinal cord slices are embedded in paraffin blocks. Sectioning and staining with hematoxylin and eosin and CD45 staining for inflammation, and with Kluver-PAS (Luxol fast blue plus Periodic Acid Schiff staining) and Bielchowski's staining for the detection of demyelination and axonal loss, are performed.

In the spinal cord, the total area of all slices is measured for each animal as points of intersection of a 10×10 grid at a magnification of 0.4×0.4 mm per grid. The perivascular inflammatory infiltrates are counted in each slice in order to obtain a total value for each animal and evaluated as number of infiltrates per mm². Demyelination and axonal loss areas are measured for each animal as points of intersection of 10×10 grid at a magnification of 0.1×0.1 mm per grid and are expressed as a percentage of total demyelination area over the total area of the slices.

Data Evaluation and Statistical Analysis

The results of clinical and histopathological observations are expressed as the mean (±SEM) scores in each treatment group. Values obtained in the test drug-treated groups are compared with that of the positive control group. Significance of differences among groups relating to clinical score are analysed by one-way ANOVA, followed in case of significance ($p<0.05$) by Fisher test.

Differences among groups for the presence of perivascular inflammatory infiltrates and the extent of demyelination and axonal loss in the spinal cord as well as body weight data are analysed by one-way ANOVA, followed in case of significance ($p<0.05$) by Fisher test.

Example 92

Preparation of a Pharmaceutical Formulation

The following formulation examples illustrate representative pharmaceutical compositions according to the present invention being not restricted thereto.

Formulation 1—Tablets

A compound of the invention is admixed as a dry powder with a dry gelatin binder in an approximate 1:2 weight ration. A minor amount of magnesium stearate is added as a lubricant. The mixture is formed into 240-270 mg tablets (80-90 mg) of active Sulfonamide derivative per tablet) in a tablet press.

Formulation 2—Capsules

A compound of the invention is admixed as a dry powder with a starch diluent in an approximate 1:1 weight ratio. The mixture is filled into 250 mg capsules (125 mg of active Sulfonamide derivative per capsule).

Formulation 3—Liquid

A compound of the invention (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active Sulfonamide derivative) in a tablet press.

Formulation 5—Injection

A compound of the invention is dissolved in a buffered sterile saline injectable aqueous medium to a concentration of approximately 5 mg/ml.

The invention claimed is:

1. A compound of Formula (Ia), wherein:
$R^2$ and $R^3$ are independently selected from:
  hydrogen,
  halogen,
  linear or branched $C_1$-$C_6$ alkyl, optionally substituted with one or more substituents selected from the group consisting of halogen, hydroxy, linear or branched $C_1$-$C_6$ alkoxy, phenoxy,
  linear or branched $C_1$-$C_6$ alkoxy,
  phenyl, optionally substituted with one or more substituents selected from the group consisting of halogen, hydroxy, linear or branched $C_1$-$C_6$ alkyl,
  phenyl-linear or branched $C_1$-$C_6$ alkyl, said phenyl optionally substituted with one or more substituents selected from the group consisting of halogen, hydroxy, linear or branched $C_1$-$C_6$ alkyl,
  a three to six member heterocyclic group having at least a heteroatom selected from the group consisting of oxygen, nitrogen and sulfur;
$R^{13}$ is selected from H, linear or branched $C_1$-$C_6$ alkyl;
$R^{14}$ is selected from
  linear or branched $C_1$-$C_8$ alkyl, optionally substituted with one or more halogen atoms and/or hydroxy groups, said $C_1$-$C_8$ alkyl optionally containing one or more unsaturated C—C bonds or containing one or more oxygen or sulfur atoms in the alkyl chain,
  $C_3$-$C_8$ cycloalkyl, optionally substituted with a carboxy or a linear or branched $C_1$-$C_4$ alkoxycarbonyl group,
  phenyl,
  phenyl-linear or branched $C_1$-$C_6$ alkyl, said $C_1$-$C_6$ alkyl optionally containing one oxygen atom,
  a heterocyclic or heterocycloalkyl group selected from the group consisting of: 1,3-dioxolane, 2,2-dimethyl-1,3-dioxolane, thiophene, 1-methyl-1-morpholino-4-ylethyl, pyrimidine, pyridine, said pyridine optionally substituted with a hydroxy or $C_1$-$C_6$ alkoxy group;
  pyridinyl-linear or branched $C_1$-$C_4$ alkyl; piperidine, said piperidine optionally substituted with phenyl-$C_1$-$C_4$ alkyl; furan, tetrahydrofuran; 2-tetrahydrofuran-2-ylethyl, pyrrolidine N-carboxylic acid, $C_1$-$C_4$ linear or branched N-alkoxycarbonylpyrrolidin-2-yl; tetrahydropyran; or
$R^{13}$ and $R^{14}$ taken together form a $C_3$-$C_8$ cycloalkyl;
n is an integer selected from 0 and 1;
as well as its geometrical isomers, its optically active forms as enantiomers, diastereomers, tautomers, racemate forms, as well as pharmaceutically acceptable salts thereof.

2. A compound according to claim 1 wherein $R^2$ and $R^3$ are independently selected from H and alkoxy.

3. A compound according to claim 1 wherein $R^{13}$ is H.

4. A compound according to claim 1 wherein $R^{13}$ is H; $R^2$ is selected from H and alkoxy; $R^{14}$ and n are as defined in the preceding claims.

5. A compound according to claim 1 wherein $R^{14}$ is selected from phenyl and a heterocyclic or heterocycloalkyl group selected from the group consisting of: 1,3-dioxolane, 2,2-dimethyl-1,3-dioxolane, thiophene, 1-methyl-1-morpholino-4-ylethyl, pyrimidine, pyridine, said pyridine optionally substituted with a hydroxy or $C_1$-$C_6$ alkoxy group; pyridinyl-linear or branched $C_1$-$C_4$ alkyl; piperidine, said piperidine optionally substituted with phenyl-$C_1$-$C_4$ alkyl; furan, tetrahydrofuran; 2-tetrahydrofuran-2-ylethyl, pyrrolidine N-carboxylic acid, $C_1$-$C_4$ linear or branched N-alkoxycarbonylpyrrolidin-2-yl; tetrahydropyran.

6. A compound according to claim 1 wherein n is 0.

7. A compound according to claim 1 wherein n is 1.

8. A compound according to claim 1, wherein $R^{13}$ is selected from H, linear or branched $C_1$-$C_6$ alkyl and $R_{14}$ is linear or branched $C_1$-$C_8$ alkyl, optionally substituted with one or more halogen atoms and/or hydroxy groups, said $C_1$-$C_8$ alkyl optionally containing one or more unsaturated C—C bonds or containing one or more oxygen or sulfur atoms in the alkyl chain.

9. A compound according to claim 1, wherein $R^{13}$ is selected from H, linear or branched $C_1$-$C_6$ alkyl and $R_{14}$ is $C_3$-$C_8$ cycloalkyl, optionally substituted with a carboxy or a linear or branched $C_1$-$C_4$ alkoxycarbonyl group.

10. A compound according to claim 1, wherein $R^{13}$ is selected from H, linear or branched $C_1$-$C_6$ alkyl and $R_{14}$ is phenyl or phenyl-linear or branched $C_1$-$C_6$ alkyl, said $C_1$-$C_6$ alkyl optionally containing one oxygen atom.

11. A compound according to claim 1, wherein $R^{13}$ is selected from H, linear or branched $C_1$-$C_6$ alkyl and $R_{14}$ is a heterocyclic or heterocycloalkyl group selected from the group consisting of: 1,3-dioxolane, 2,2-dimethyl-1,3-dioxolane, thiophene, 1-methyl-1-morpholino-4-ylethyl, pyrimidine, pyridine, said pyridine optionally substituted with a hydroxy or $C_1$-$C_6$ alkoxy group; pyridinyl-linear or branched $C_1$-$C_4$ alkyl; piperidine, said piperidine optionally substituted with phenyl-$C_1$-$C_4$ alkyl; furan, tetrahydrofuran; 2-tetrahydrofuran-2-ylethyl, pyrrolidine N-carboxylic acid, $C_1$-$C_4$ linear or branched N-alkoxycarbonylpyrrolidin-2-yl; tetrahydropyran.

12. A compound according to claim 1, wherein $R^{13}$ and $R_{14}$ taken together form a cyclopentyl group.

13. A compound according to claim 1, selected from the following group:
N-{1-[(3,4-dihydroisoquinolin-2(1H)-ylsulfonyl)methyl]-3-phenylpropyl}-N-hydroxy formamide;
N-{2-(3,4-dihydroisoquinolin-2(1H)-ylsulfonyl)-1-[(4S)-2,2-dimethyl-1,3-dioxolan-4-yl]ethyl}-N-hydroxyformamide;
N-{1-[(3,4-dihydroisoquinolin-2(1H)-ylsulfonyl)methyl]hexyl}-N-hydroxyformamide;
N-[1-cyclopropyl-2-(3,4-dihydroisoquinolin-2(1H)-ylsulfonyl)ethyl]-N-hydroxy formamide;
N-[2-(3,4-dihydroisoquinolin-2(1H)-ylsulfonyl)-1-(2-thienyl)ethyl]-N-hydroxyformamide;
N-{1-[(1,3-dihydro-2H-isoindol-2-ylsulfonyl)methyl]-3-phenylpropyl}-N-hydroxy formamide;
N-[2-(3,4-dihydroisoquinolin-2(1H)-ylsulfonyl)-1-(3-thienyl)ethyl]-N-hydroxyformamide;
N-{1-[(3,4-dihydroisoquinolin-2(1H)-ylsulfonyl)methyl]-2-methyl-2-morpholin-4-yl propyl}-N-hydroxyformamide;
N-[2-(3,4-dihydroisoquinolin-2(1H)-ylsulfonyl)-1-pyrimidin-5-ylethyl]-N-hydroxy formamide;
N-[2-(3,4-dihydroisoquinolin-2(1H)-ylsulfonyl)-1-pyridin-3-ylethyl]-N-hydroxy formamide;
N-[2-(3,4-dihydroisoquinolin-2(1H)-ylsulfonyl)-1-pyridin-3-ylethyl]-N-hydroxy formamide; hydrochloride salt;
N-(1-{[(6,7-dimethoxy-3,4-dihydroisoquinolin-2(1H)-yl)sulfonyl]methyl}-3-phenyl propyl)-N-hydroxyformamide;
N-[2-(3,4-dihydroisoquinolin-2(1H)-ylsulfonyl)-1-(6-methoxypyridin-3-yl)ethyl]-N-hydroxyformamide;
N-{2-[(6,7-dimethoxy-3,4-dihydroisoquinolin-2(1H)-yl)sulfonyl]-1-[(4S)-2,2-dimethyl-1,3-dioxolan-4-yl]ethyl}-N-hydroxyformamide;
N-{1-cyclopentyl-2-[(6,7-dimethoxy-3,4-dihydroisoquinolin-2(1H)-yl)sulfonyl]ethyl}-N-hydroxyformamide;
N-{2-(1,3-dihydro-2H-isoindol-2-ylsulfonyl)-1-[(4S)-2,2-dimethyl-1,3-dioxolan-4-yl]ethyl}-N-hydroxyformamide;
N-(1-{[(6,7-dimethoxy-3,4-dihydroisoquinolin-2(1H)-yl)sulfonyl]methyl}-2-ethylbutyl)-N-hydroxyformamide;
N-{1-[(4S)-2,2-dimethyl-1,3-dioxolan-4-yl]-2-[(6-isopropyl-3,4-dihydroisoquinolin-2(1H)-yl)sulfonyl]ethyl}-N-hydroxyformamide;
N-{2-[(7-chloro-3,4-dihydroisoquinolin-2(1H)-ylsulfonyl]-1-[(4S)-2,2-dimethyl-1,3-dioxolan-4-yl]ethyl}-N-hydroxyformamide;
N-(1-{[(6,7-dimethoxy-3,4-dihydroisoquinolin-2(1H)-yl)sulfonyl]-methyl}-2,2-dimethylpropyl)-N-hydroxyformamide;
N-{2-[(7-chloro-3,4-dihydroisoquinolin-2(1H)-yl)sulfonyl]-1-cyclopentylethyl}-N-hydroxyformamide;
N-{(1R)-2-[(7-chloro-3,4-dihydroisoquinolin-2(1H)-yl)sulfonyl]-1-[(2R)-tetrahydrofuran-2-yl]ethyl}-N-hydroxyformamide,
N-{(1S)-2-[(7-chloro-3,4-dihydroisoquinolin-2(1H)-yl)sulfonyl]-1-[(2R)-tetrahydrofuran-2-yl]ethyl}-N-hydroxyformamide;
N-((1S,2S)-1-{[(6,7-dimethoxy-3,4-dihydroisoquinolin-2(1H)-yl)sulfonyl]methyl}-2,3-dihydroxypropyl)-N-hydroxyformamide;
N-(1-cyclopentyl-2-{[6-(trifluoromethyl)-3,4-dihydroisoquinolin-2(1H)-yl]sulfonyl}ethyl)-N-hydroxyformamide;
N-(1-{[(5-fluoro-1,3-dihydro-2H-isoindol-2-yl)sulfonyl]methyl}-3,3-dimethylbutyl)-N-hydroxyformamide;
N-hydroxy-N-((1S)-1-[(2R)-tetrahydrofuran-2-yl]-2-{[7-(trifluoromethyl)-3,4-dihydroisoquinolin-2(1H)-yl]sulfonyl}ethyl)formamide;
N-(1-[(4S)-2,2-dimethyl-1,3-dioxolan-4-yl]-2-{[7-(trifluoromethyl)-3,4-dihydroisoquinolin-2(1H)-yl]sulfonyl}ethyl)-N-hydroxyformamide;
N-{(1S)-2-[(5-fluoro-1,3-dihydro-2H-isoindol-2-yl)sulfony]-1-[(2R)-tetrahydrofuran-2-yl]ethyl}-N-hydroxyformamide;
N-[2,2-dimethyl-1-({[6-(trifluoromethyl)-3,4-dihydroisoquinolin-2(1H)-yl]sulfonyl}methyl)hept-4-yn-1-yl]-N-hydroxyformamide;
N-[2,2-dimethyl-3-phenyl-1-({[6-(trifluoromethyl)-3,4-dihydroisoquinolin-2(1H)-yl]sulfonyl}methyl)propyl]-N-hydroxyformamide;

N-hydroxy-N-((1R)-1-[(2R)-tetrahydrofuran-2-yl]-2-{[7-(trifluoromethyl)-3,4-dihydroisoquinolin-2(1H)-yl]sulfonyl}ethyl)formamide;

N-hydroxy-N-[1-{[(7-methoxy-3,4-dihydroisoquinolin-2(1H)-yl)sulfonyl]methyl}-3-(tetrahydrofuran-2-yl)propyl]formamide;

N-(1-{[(6,7-dichloro-3,4-dihydroisoquinolin-2(1H)-yl)sulfonyl]methyl}-2-ethylbutyl)-N-hydroxyformamide;

N-(2-ethyl-1-{[(6-isopropyl-3,4-dihydroisoquinolin-2(1H)-yl)sulfonyl]methyl}butyl)-N-hydroxyformamide;

N-(1-{[(7-bromo-3,4-dihydroisoquinolin-2(1H)-yl)sulfonyl]methyl}-2-ethylbutyl)-N-hydroxyformamide;

N-[2-ethyl-1-({[6-(trifluoromethyl)-3,4-dihydroisoquinolin-2(1H)-yl]sulfonyl}methyl)butyl]-N-hydroxyformamide;

N-(2-ethyl-1-{[(7-methoxy-3,4-dihydroisoquinolin-2(1H)-yl)sulfonyl]methyl}butyl)-N-hydroxyformamide;

N-(1-{[(6,7-dichloro-3,4-dihydroisoquinolin-2(1H)-yl)sulfonyl]methyl}-2-methylpropyl)-N-hydroxyformamide;

N-(3,3-dimethyl-1-{[(7-propoxy-3,4-dihydroisoquinolin-2(1H)-yl)sulfonyl]methyl}butyl)-N-hydroxyformamide;

N-(1-{[(7-chloro-3,4-dihydroisoquinolin-2(1H)-yl)sulfonyl]methyl}-3,3-dimethylbutyl)-N-hydroxyformamide;

N-(1-{[(6,7-dichloro-3,4-dihydroisoquinolin-2(1H)-yl)sulfonyl]methyl}-3,3-dimethylbutyl)-N-hydroxyformamide;

N-[3,3-dimethyl-1-({[6-(trifluoromethyl)-3,4-dihydroisoquinolin-2(1H)-yl]sulfonyl}methyl)butyl]-N-hydroxyformamide;

tert-butyl (2RS)-2-{(1SR)-2-[(6,7-dichloro-3,4-dihydroisoquinolin-2(1H)-yl)sul-fon-yl]-1-[formyl(hydroxy)amino]ethyl}pyrrolidine-1-carboxylate N-hydroxy-N-{(1S)-2-[(6-isopropyl-3,4-dihydroisoquinolin-2(1H)-yl)sulfonyl]-1-[(2R)-tetrahydrofuran-2-yl]ethyl}formamide;

tert-butyl (2RS)-2-{(1RS)-2-[(6,7-dichloro-3,4-dihydroisoquinolin-2(1H)-yl)sulfon-yl]-1-[formyl(hydroxy)amino]ethyl}pyrrolidine-1-carboxylate N-hydroxy-N-(1-[(2R)-tetrahydrofuran-2-yl]-2-{[6-(trifluoromethyl)-3,4-dihydroisoquinolin-2(1H)-yl]sulfonyl}ethyl)formamide;

N-(1-{[(7-chloro-3,4-dihydroisoquinolin-2(1H)-yl)sulfonyl]methyl}-3-hydroxypropyl)-N-hydroxyformamide;

N-[2-[(6,7-dichloro-3,4-dihydroisoquinolin-2(1H)-yl)sulfonyl]-1-(hydroxymethyl)ethyl]-N-hydroxyformamide;

N-[1-({[7-(4-fluorophenyl)-3,4-dihydroisoquinolin-2(1H)-yl]sulfonyl}methyl)-2-methylpropyl]-N-hydroxyformamide;

N-hydroxy-N-(1-{[(7-isopropoxy-3,4-dihydroisoquinolin-2(1H)-yl)sulfonyl]methyl}-3-methylbutyl)formamide;

N-[2-[(7-fluoro-3,4-dihydroisoquinolin-2(1H)-yl)sulfonyl]-1-(3-furyl)ethyl]-N-hydroxyformamide;

N-{1-(1-benzylpiperidin-4-yl)-2-[(7-fluoro-3,4-dihydroisoquinolin-2(1H)-yl)sulfonyl]ethyl}-N-hydroxyformamide;

N-[1-{[(7-tert-butyl-3,4-dihydroisoquinolin-2(1H)-yl)sulfonyl]methyl}-3-(methylthio)propyl]-N-hydroxyformamide;

N-(1-{[(7-bromo-3,4-dihydroisoquinolin-2(1H)-yl)sulfonyl]methyl}-3-methylbutyl)-N-hydroxyformamide;

N-{2-[(7-bromo-3,4-dihydroisoquinolin-2(1H)-yl)sulfonyl]-1,1-dimethylethyl}-N-hydroxyformamide;

N-(2-(benzyloxy)-1-{[(7-tert-butyl-3,4-dihydroisoquinolin-2(1H)-yl)sulfonyl]methyl}ethyl)-N-hydroxyformamide;

N-(2-(benzyloxy)-1-{[(7-chloro-3,4-dihydroisoquinolin-2(1H)-yl)sulfonyl]methyl}ethyl)-N-hydroxyformamide;

N-[2-(benzyloxy)-1-({[7-(trifluoromethyl)-3,4-dihydroisoquinolin-2(1H)-yl]sulfonyl}methyl)ethyl]-N-hydroxyformamide;

N-{1-cyclopentyl-2-[(7-fluoro-3,4-dihydroisoquinolin-2(1H)-yl)sulfonyl]ethyl}-N-hydroxyformamide;

N-[2-[(7-chloro-3,4-dihydroisoquinolin-2(1H)-yl)sulfonyl]-1-(phenoxymethyl)ethyl]-N-hydroxyformamide;

N-(1-{[(7-chloro-3,4-dihydroisoquinolin-2(1H)-yl)sulfonyl]methyl}cyclopentyl)-N-hydroxyformamide;

N-[2,2-dimethyl-1-({[6-(trifluoromethyl)-3,4-dihydroisoquinolin-2(1H)-yl]sulfonyl}methyl)heptyl]-N-hydroxyformamide;

N-{2-[(7-bromo-3,4-dihydroisoquinolin-2(1H)-yl)sulfonyl]-1-cyclopentylethyl}-N-hydroxyformamide;

N-(1-{[(7-chloro-3,4-dihydroisoquinolin-2(1H)-yl)sulfonyl]methyl}-2,2-dimethylpropyl)-N-hydroxyformamide;

N-[2-[(7-tert-butyl-3,4-dihydroisoquinolin-2(1H)-yl)sulfonyl]-1-(tetrahydro-2H-pyran-4-yl)ethyl]-N-hydroxyformamide;

ethyl 2-{2-[(6,7-dimethoxy-3,4-dihydroisoquinolin-2(1H)-yl)sulfonyl]-1-[formyl-(hydroxy)amino]ethyl}cyclopropanecarboxylate N-(1-cyclopentyl-2-{[7-(3-thienyl)-3,4-dihydroisoquinolin-2(1H)-yl]sulfonyl}ethyl)-N-hydroxyformamide;

N-{1-cyclopentyl-2-[(7-phenyl-3,4-dihydroisoquinolin-2(1H)-yl)sulfonyl]ethyl}-N-hydroxyformamide;

N-(1-cyclopentyl-2-{[7-(3-hydroxyphenyl)-3,4-dihydroisoquinolin-2(1H)-yl]sulfonyl}ethyl)-N-hydroxyformamide;

2-{2-[(6,7-dimethoxy-3,4-dihydroisoquinolin-2(1H)-yl)sulfonyl]-1-[formyl(hydroxy)amino]ethyl}cyclopropanecarboxylic acid N-[1-cyclopropyl-2-(1,3-dihydro-2H-isoindol-2-ylsulfonyl)ethyl]-N-hydroxyformamide;

N-{2-[(7-chloro-3,4-dihydroisoquinolin-2(1H)-yl)sulfonyl]-1-cyclopropylethyl}-N-hydroxyformamide;

N-(1-cyclopropyl-2-{[6-(trifluoromethyl)-3,4-dihydroisoquinolin-2(1H)-yl]sulfonyl}ethyl)-N-hydroxyformamide;

N-(1-cyclopropyl-2-{[7-(4-fluorophenyl)-3,4-dihydroisoquinolin-2(1H)-yl]sulfonyl}ethyl)-N-hydroxyformamide;

N-(1-{[(7-chloro-3,4-dihydroisoquinolin-2(1H)-yl)sulfonyl]methyl}-4,4,4-trifluorobutyl)-N-hydroxyformamide;

N-{1-cyclopentyl-2-[(6,7-dichloro-3,4-dihydroisoquinolin-2(1H)-yl)sulfonyl]ethyl}-N-hydroxyformamide;

N-{1-cyclopentyl-2-[(7-isopropoxy-3,4-dihydroisoquinolin-2(1H)-yl)sulfonyl]ethyl}-N-hydroxyformamide;

N-{1-cyclopentyl-2-[(7-pyridin-4-yl-3,4-dihydroisoquinolin-2(1H)-yl)sulfonyl]ethyl}-N-hydroxyformamide;

N-{1-cyclopentyl-2-[(5-fluoro-1,3-dihydro-2H-isoindol-2-yl)sulfonyl]ethyl}-N-hydroxyformamide;

N-{1-cyclopentyl-2-[(6-isopropyl-3,4-dihydroisoquinolin-2(1H)-yl)sulfonyl]ethyl}-N-hydroxyformamide;

N-(1-cyclopentyl-2-{[7-(trifluoromethyl)-3,4-dihydroisoquinolin-2(1H)-yl]sulfonyl}ethyl)-N-hydroxyformamide;

N-(1-cyclopropyl-2-{[7-(trifluoromethyl)-3,4-dihydroisoquinolin-2(1H)-yl]sulfonyl}ethyl)-N-hydroxyformamide;

N-{1-cyclopropyl-2-[(6,7-dimethoxy-3,4-dihydroisoquinolin-2(1H)-yl)sulfonyl]ethyl}-N-hydroxyformamide;

N-{1-cyclopropyl-2-[(6-isopropyl-3,4-dihydroisoquinolin-2(1H)-yl)sulfonyl]ethyl}-N-hydroxyformamide;

N-(1-{[(7-chloro-3,4-dihydroisoquinolin-2(1H)-yl)sulfonyl]methyl}-3-pyridin-3-ylpropyl)-N-hydroxyformamide.

14. A compound according to claim 1 for use as medicament for the modulation of metalloproteinases MMP1, MMP2, MMP9, MMP12, MMP13, and MMP14 and/or TACE.

15. A pharmaceutical composition comprising at least one compound according to claim 1 and a pharmaceutically acceptable carrier, diluent or excipient thereof.

16. A process for the preparation of a compound, according to claim 1, comprising the step of reacting a compound of Formula (II) with a formylating agent of formula (FA):

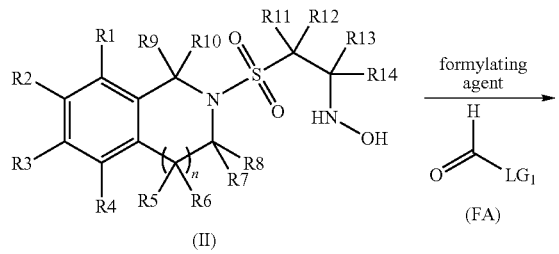

-continued

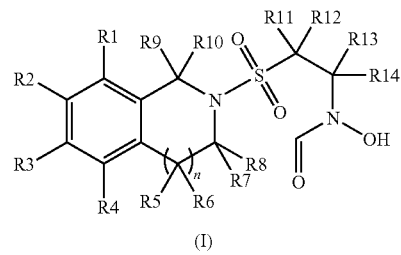

wherein $R^1$, $R^4$, $R^5$, $R^6$, $R^7$, $R^8$, $R^9$, $R^{10}$, $R^{11}$, $R^{12}$, are hydrogen, $R^2$, $R^3$, $R^{13}$, $R^{14}$ and n are as defined in the preceding claims and $LG_1$ is a leaving group selected from selected from —OH, —OAc, —OPiv, —OCH$_2$CN, —OCH$_2$CF$_3$, —OPh and —OPfp.

17. A compound according to claim 1 for use in the treatment of a disease selected from pulmonary fibrosis, pancreatic fibrosis, psoriasis, skin fibrosis and liver fibrosis.

* * * * *